(12) United States Patent
Iwamoto et al.

(10) Patent No.: US 7,011,701 B2
(45) Date of Patent: *Mar. 14, 2006

(54) DYE AND INK JET PRINTING INK

(75) Inventors: Kyoko Iwamoto, Tokyo (JP); Hidetaka Ninomiya, Mitaka (JP); Satoru Ikesu, Fuchu (JP); Takatugu Suzuki, Hachioji (JP); Mari Takahashi, Asaka (JP)

(73) Assignee: Konica Minolta Holdings, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/717,141

(22) Filed: Nov. 19, 2003

(65) Prior Publication Data

US 2004/0106782 A1    Jun. 3, 2004

(30) Foreign Application Priority Data

Nov. 27, 2002 (JP) .............................. 2002-343792
Oct. 7, 2003 (JP) .............................. 2003-348021

(51) Int. Cl.
*C09D 11/02* (2006.01)
*C07D 221/18* (2006.01)
*C07D 237/26* (2006.01)
*C07D 239/70* (2006.01)

(52) U.S. Cl. ................. 106/31.47; 546/61; 546/75; 544/233; 544/248

(58) Field of Classification Search ............ 106/31.47; 546/61, 75; 544/233, 248
See application file for complete search history.

(56) References Cited

U.S. PATENT DOCUMENTS

| | | | | |
|---|---|---|---|---|
| 1,980,549 A * | 11/1934 | Raeder | ............ | 544/245 |
| 2,040,859 A * | 5/1936 | Kunz et al. | ............ | 544/248 |
| 2,068,989 A * | 1/1937 | Koeberle et al. | ............ | 544/248 |
| 2,557,328 A * | 6/1951 | Wardleworth | ............ | 8/636 |
| 2,778,831 A * | 1/1957 | Lodge et al. | ............ | 544/248 |
| 2,962,497 A * | 11/1960 | Guenthard | ............ | 544/188 |
| 3,203,956 A * | 8/1965 | Orelup | ............ | 546/75 |
| 3,862,944 A * | 1/1975 | Eilingsfeld et al. | ............ | 544/248 |
| 3,939,162 A * | 2/1976 | Elser et al. | ............ | 544/248 |
| 4,001,170 A * | 1/1977 | Wick | ............ | 524/89 |
| 4,088,572 A * | 5/1978 | Cooper et al. | ............ | 546/74 |
| 5,959,110 A * | 9/1999 | Nichols et al. | ............ | 546/75 |
| 6,846,351 B1 * | 1/2005 | Iwamoto et al. | ............ | 106/31.47 |
| 6,916,364 B1 * | 7/2005 | Iwamoto et al. | ............ | 106/31.47 |
| 2003/0230216 A1 * | 12/2003 | Iwamoto et al. | ............ | 106/31.47 |

FOREIGN PATENT DOCUMENTS

| | | |
|---|---|---|
| JP | 10-306221 A | 11/1998 |
| JP | 2001-311016 A | 11/2001 |
| JP | 2002-371079 A | 12/2002 |

* cited by examiner

*Primary Examiner*—Helene Klemanski
(74) *Attorney, Agent, or Firm*—Frishauf, Holtz, Goodman & Chick, P.C.

(57) ABSTRACT

A dye is disclosed, which is represented by the following formula:

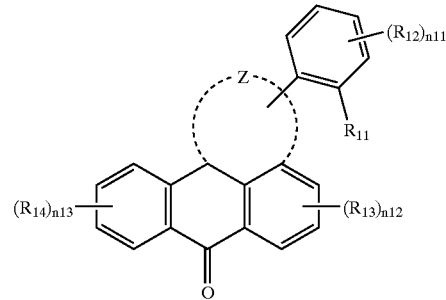

wherein Z is an atomic group necessary to form a 6-membered nitrogen containing aromatic ring; $R_{11}$ is a hydrogen bonding group; $R_{12}$, $R_{13}$ and $R_{14}$ are independently a hydrogen atom or a substituent; n11 and n13 are each an integer of 1 to 4; n12 is an integer of 1 to 3. There is also disclosed an ink for ink jet printing which contains the foregoing dye.

13 Claims, No Drawings

DYE AND INK JET PRINTING INK

FIELD OF THE INVENTION

The present invention relates to a specific dye and an ink jet printing ink which contains the dye and in particular to an ink jet printing ink which exhibits superior color image fastness.

BACKGROUND OF THE INVENTION

Recently, the major trend in image recording material has been directed to material for color imaging. Specifically, there are employed ink jet printing material, thermal transfer type recording material, recording material using an electrophotography system, transfer type silver halide photographic material, printing inks and recording pens. Color filters are also used in displays such as LCD (liquid crystal display) and PDP (plasma display panel) and in electronic parts such as CCD for use in picture-taking instruments. In these color imaging materials and color filters, dyes and pigments of the three primary colors of a so-called additive mixture system or subtractive mixture system are employed to reproduce or record full color images. However, there is actually no dye which is durable under various conditions for use and an improvement thereof has been desired.

Specifically in inks for use in ink jet printing are desired compatibility with a recording system used, having a relatively high image recording density and superior color tone, superior color image durability such as light fastness, heat fastness and water resistance, rapid fixability onto a recording medium without bleeding, superior storage stability as ink, no problem in safety such as toxicity or inflammability, and low cost.

In light of the foregoing, there have been proposed or studied various inks for ink jet printing but inks meeting many requirements are limited.

In color image recording with yellow, magenta, cyan and black, for example, there have been studied commonly known dyes and pigments having a C.I. number described in the C.I. index. In yellow inks using water-soluble dyes, for example, the use of azo-type water-soluble dyes such as Direct Yellow 96 and C.I. Direct Yellow 132 are known; however, such dyes cause problems that the dyes fall within a short wavelength region and do not easily raise print density, and in addition still have problems in fastness such as light fastness, while being at a higher level than magenta. Magenta inks using xanthene dyes such as C.I. Acid Red 52 or water-soluble azo dyes such as C.I. Direct Red 20 have been known, which exhibit high reliability with respect to clogging caused in a printer, while having problems in fastness such as light fastness and water resistance. There is also known the use of quinacridone pigments such as C.I. Pigment Red 122, which exhibits relatively high color fastness, while producing problems in color reproduction, such as low printing density or bronzing. Color and fastness required for ink jet ink are inconsistent in conventional dyes and pigments.

To overcome the foregoing problems, an azo dye, anthrapyridone compounds and a water-based ink composition containing the same were proposed to improve both color and light fastness, such as yellow inks described in JP-A Nos. 2002-371079 and 2001-311016 (hereinafter, the term, JP-A refers to Japanese Patent Application Publication) and a magenta ink described in JP-A No. 10-306221. However, they are still insufficient in light fastness and an improvement thereof is still desired.

SUMMARY OF THE INVENTION

It is an object of the present invention to provide a dye exhibiting superior fastness and an ink jet printing ink which forms images of superior light fastness, specifically, yellow and magenta ink jet printing inks. It is an object of the invention to provide a water-based ink jet printing ink of superior light fastness and guaranteed long runs.

The foregoing object of the invention can be achieved by the following constitution. Thus, one aspect of the invention concerns a dye represented by the following formula (1):

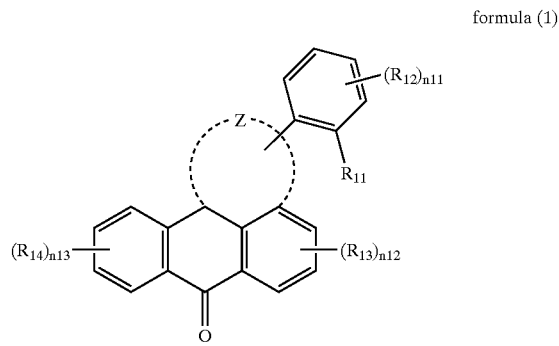

formula (1)

wherein Z is an atomic group necessary to form a 6-membered nitrogen containing aromatic ring; $R_{11}$ is a hydrogen bonding group; $R_{12}$, $R_{13}$ and $R_{14}$ are independently a hydrogen atom or a substituent; n12 is an integer of 1 to 3, n11 and n13 are each an integer of 1 to 4.

Another aspect of the invention concerns an ink composition for ink jet printing, comprising a dye described above.

DETAILED DESCRIPTION OF THE INVENTION

The compound represented by the foregoing formula (1) will be further detailed. In the foregoing formula (1), Z represents an atomic group necessary to form a 6-membered nitrogen containing aromatic ring. Specific examples of the 6-membered nitrogen containing aromatic ring formed by Z include a pyridine ring, pyrimidine ring, and pyridazine ring. Such aromatic rings may further be substituted.

In the formula (1), $R_{11}$ represents a hydrogen bonding group. The hydrogen bonding group refers to a group having an active hydrogen atom capable of forming a hydrogen bond with a nitrogen atom included in the foregoing 6-membered nitrogen containing aromatic ring formed by Z. Specific examples of the hydrogen bonding group represented by $R_{11}$ include —OH, —NHCOR$_4$, —NHCOOR$_4$, —NHSO$_2$R$_4$ and —NHSO$_2$NHR$_4$, in which R$_4$ is a substituent (preferably an alkyl group, an aryl group, or a heterocyclic group) and $R_{11}$ is preferably —OH or —NHSO$_2$R$_4$.

$R_{12}$, $R_{13}$ and $R_{14}$ are independently a hydrogen atom or a substituent. The substituent is not specifically limited. Specific examples of the substituent include alkyl, aryl, anilino, acylamino, sulfonamido, alkylthio, arylthio, alkenyl, cycloalkyl, halogen atom, cycloalkenyl, alkynyl, heterocyclic group, sulfonyl, sulfinyl, phosphonyl, acyl, carbamoyl, sulfamoyl, cyano, alkoxy, aryloxy, heterocyclic-oxy, siloxy, acyloxy, sulfonyloxy, carbamoyloxy, amino, alkylamino, imido, ureido, sulfamoylamino, alkoxycarbonylamino, aryloxycarbonylamino, alkoxycarbonyl, aryloxycarbonyl, heterocyclic-thio, thioureido, carboxyl, hydroxyl, mercapto, nitro and sulfo (or sulfonic acid) groups, and a spiro-compound residue and bridged hydrocarbon compound residue are also included.

In formula (1), n11 and n13 are each an integer of 1 to 4, and n12 is an integer of 1 to 3, provided that when n11, n12 or n13 is 2 or more, the respective $R_{12}$, $R_{13}$ and $R_{14}$ may be the same or different, and when n11, n12 or n13 is 2 or more, two $R_{12}$s, two $R_{13}$s or two $R_{14}$s may combine with each other to form a ring.

The dye represented by foregoing formula (1) is preferably a dye represented by the following formula (2), (3), (4), (5), (6) or (7):

formula (2)

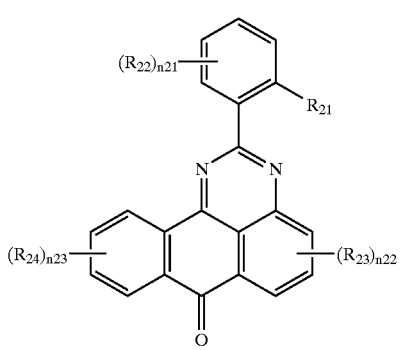

formula (3)

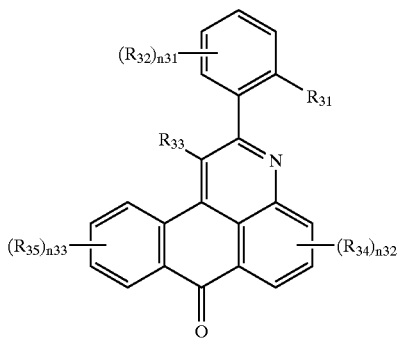

formula (4)

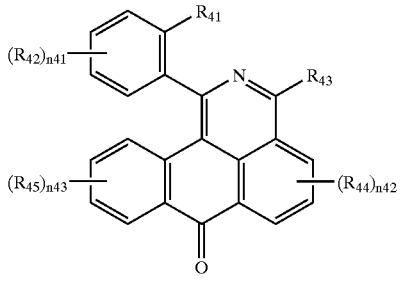

formula (5)

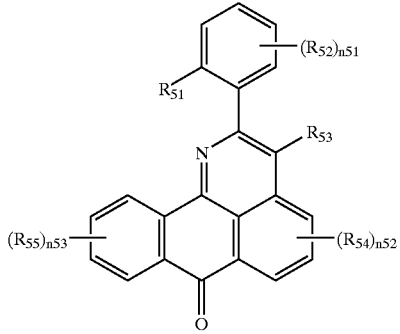

formula (6)

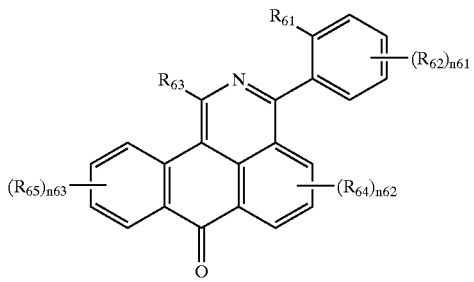

formula (7)

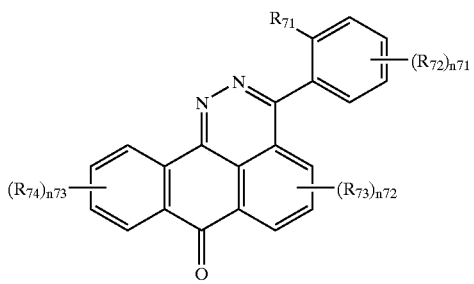

wherein $R_{21}$, $R_{31}$, $R_{41}$, $R_{51}$, $R_{61}$, and $R_{71}$, are each a hydrogen bonding atom; $R_{22}$, $R_{23}$, $R_{24}$, $R_{32}$, $R_{33}$, $R_{34}$, $R_{35}$, $R_{42}$, $R_{43}$, $R_{44}$, $R_{45}$, $R_{52}$, $R_{53}$, $R_{54}$, $R_{55}$, $R_{62}$, $R_{63}$, $R_{64}$, $R_{65}$, $R_{72}$, $R_{73}$, and $R_{74}$ are independently a hydrogen atom or a substituent; n21, n23, n31, n33, n41, n43, n51, n53, n61, n63, n71 and n73 are each an integer of 1 to 4; n22, n32, n42, n52, n62 and n72 are each an integer of 1 to 3;

In the formula (2), $R_{21}$ represents a hydrogen bonding group. Specific examples of the hydrogen bonding group are the same as those cited in the foregoing $R_{11}$ of formula (1) and preferred ones are the same as cited in the foregoing formula (1). $R_{22}$, $R_{23}$ and $R_{24}$ represents a hydrogen atom or a substituent and specific examples of the substituent are the same as cited in the foregoing $R_{12}$, $R_{13}$ and $R_{14}$ of the formula (1).

In formula (2), n21 and n23 are each an integer of 1 to 4, and n22 is an integer of 1 to 3, provided that when n21, n22 or n23 is 2 or more, the respective $R_{22}$, $R_{23}$ and $R_{24}$ may be the same or different, and when n21, n22 or n23 is 2 or more, two $R_{22}$s, two $R_{23}$s or two $R_{24}$s may combine with each other to form a ring.

In formula (3), $R_{31}$, represents a hydrogen bonding group. Specific examples of the hydrogen bonding group are the same as those cited in $R_{11}$ of the foregoing formula (1) and preferred ones are the same as defined in the foregoing formula (1). $R_{32}$, $R_{33}$, $R_{34}$ and $R_{35}$each represents a hydrogen atom or a substituent and specific examples of the substituent are the same as cited in the foregoing $R_{12}$, $R_{13}$ and $R_{14}$ of the formula (1).

In formula (3), n31 and n33 are each an integer of 1 to 4, and n32 is an integer of 1 to 3, provided that when n31, n32 or n33 is 2 or more, the respective $R_{32}$, $R_{34}$ and $R_{35}$ may be the same or different, and when n31, n32 or n33 is 2 or more, two $R_{32}$s, two $R_{34}$s or two $R_{35}$s may combine with each other to form a ring.

In formula (4), $R_{41}$ represents a hydrogen bonding group. Specific examples of the hydrogen bonding group are the same as those cited in $R_{11}$ of the foregoing formula (1) and preferred ones are the same as cited in the foregoing formula (1). $R_{42}$, $R_{43}$, $R_{44}$ and $R_{45}$ represents a hydrogen atom or a substituent and specific examples of the substituent are the same as cited in the foregoing $R_{12}$, $R_{13}$ and $R_{14}$ of the formula (1).

In formula (4), n41 and n43 are each an integer of 1 to 4, and n42 is an integer of 1 to 3, provided that when n41, n42 or n43 is 2 or more, the respective $R_{42}$, $R_{44}$ and $R_{45}$ may be the same or different, and when n41, n42 or n43 is 2 or more, two $R_{42}$s, two $R_{44}$s or two $R_{45}$s may combine with each other to form a ring.

In formula (5), $R_{51}$ represents a hydrogen bonding group. Specific examples of the hydrogen bonding group are the same as those defined in $R_{11}$ of the foregoing formula (1) and preferred ones are the same as defined in the foregoing formula (1). $R_{52}$, $R_{53}$, $R_{54}$ and $R_{55}$ represents a hydrogen atom or a substituent and specific examples of the substituent are the same as cited in the foregoing $R_{12}$, $R_{13}$ and $R_{14}$ of the formula (1).

In formula (5), n51 and n53 are each an integer of 1 to 4, and n52 is an integer of 1 to 3, provided that when n51, n52 or n53 is 2 or more, the respective $R_{52}$, $R_{54}$ and $R_{55}$ may be the same or different, and when n51, n52 or n53 is 2 or more, two $R_{52}$s, two $R_{54}$s or two $R_{55}$s may combine with each other to form a ring.

In formula (6), $R_{61}$ represents a hydrogen bonding group. Specific examples of the hydrogen bonding group are the same as those defined in $R_{11}$ of the foregoing formula (1) and preferred ones are the same as defined in the foregoing formula (1). $R_{62}$, $R_{63}$, $R_{64}$ and $R_{65}$ represents a hydrogen atom or a substituent and specific examples of the substituent are the same as cited in the foregoing $R_{12}$, $R_{13}$ and $R_{14}$ of the formula (1).

In formula (6), n61 and n63 are each an integer of 1 to 4, and n62 is an integer of 1 to 3, provided that when n61, n62 or n63 is 2 or more, the respective $R_{62}$, $R_{64}$ and $R_{65}$ may be the same or different, and when n61, n62 or n63 is 2 or more, two $R_{62}$s, two $R_{64}$s or two $R_{65}$s may combine with each other to form a ring.

In formula (7), $R_{71}$ represents a hydrogen bonding group. Specific examples of the hydrogen bonding group are the same as those defined in $R_{11}$ of the foregoing formula (1) and preferred ones are the same as defined in the foregoing formula (1). $R_{72}$, $R_{73}$, and $R_{74}$ represents a hydrogen atom or a substituent and specific examples of the substituent are the same as cited in the $R_{12}$, $R_{13}$ and $R_{14}$ of the formula (1).

In formula (7), n71 and n73 are each an integer of 1 to 4, and n72 is an integer of 1 to 3, provided that when n71, n72 or n73 is 2 or more, the respective $R_{72}$, $R_{73}$ and $R_{74}$ may be the same or different, and when n31, n32 or n33 is 2 or more, two $R_{72}$s, two $R_{73}$s or two $R_{74}$s may combine with each other to form a ring.

The dye represented by foregoing formula (2) preferably is a dye represented by the following formulas (8) or (9), and the dye represented by formula (3) preferably is a dye represented by the following formulas (10) or (11):

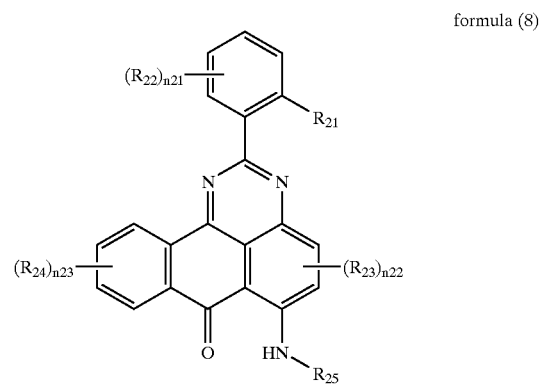

formula (8)

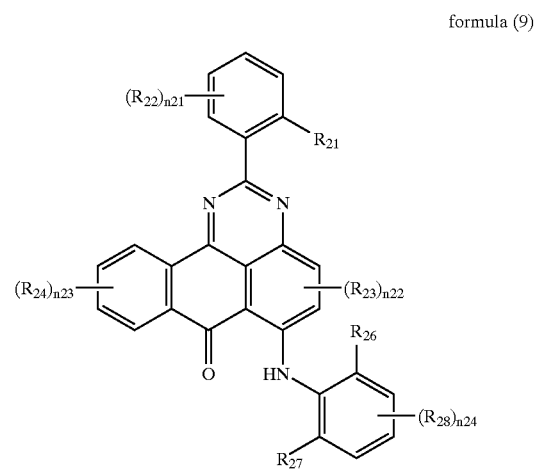

formula (9)

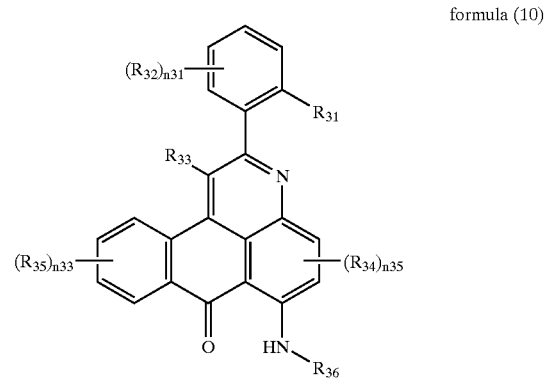

formula (10)

formula (11)

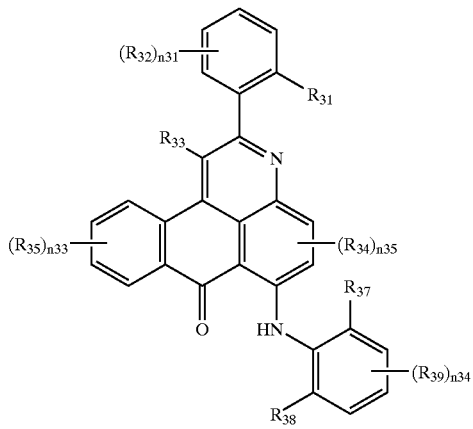

wherein $R_{21}$ and $R_{31}$ are independently a hydrogen bonding group; $R_{22}$, $R_{23}$, $R_{24}$, $R_{28}$, $R_{32}$, $R_{33}$, $R_{34}$, $R_{35}$ and $R_{39}$ are independently a hydrogen atom or a substituent; $R_{26}$, $R_{27}$, $R_{37}$ and $R_{38}$ are independently a substituent; n21, n23, n31, and n33 are each an integer of 1 to 4; n24 and n34 are each an integer of 1 to 3; n25 and n35 are each an integer of 1 or 2; $R_{25}$ and $R_{36}$ are independently a group having a Hammett substituent constant (σp value) of 0.3 to 1.0.

In the formula (8), $R_{21}$, represents a hydrogen bonding group. Specific examples of the hydrogen bonding group are the same as those cited in the foregoing $R_{11}$ of the formula (1) and preferred ones are the same as cited in the foregoing formula (1). $R_{22}$, $R_{23}$, and $R_{24}$ represents a hydrogen atom or a substituent and specific examples of the substituent are the same as defined in the foregoing $R_{12}$, $R_{13}$ and $R_{14}$ of the formula (1).

$R_{25}$ represents a group having a Hammett substituent constant (σp) of 0.3 to 1.0. The Hammett substituent constant (σp) is a substituent constant defined by Hammett, for example, as described in "Drug Structure-Activity Relationship [1]" page 96–103 (Kagaku-no-Ryoiki, Zokan No. 136, published by Nankodo). Examples of a group having a τp value of 0.3 to 1.0 include a carbonyl group (e.g., acetyl, pivaloyl, arylcarbonyl), alkoxy group, aryoxy group, cyano group, nitro group, carbamoyl group (e.g., acetocarbomoyl), sulfamoyl group (e.g., acetosulfamoyl), sulfonyl group (e.g., alkylsulfonyl, arylsulfonyl), imido group (e.g., phthalimido), perfluoroalkyl group, and trichloromethyl group.

In the formula (8), n21 and n23 are each an integer of 1 to 4, and n25 is an integer of 1 to 3, provided that when n21, n23 or n25 is 2 or more, the respective $R_{22}$, $R_{24}$ and $R_{23}$ may be the same or different, and when n21, n23 or n25 is 2 or more, two $R_{22}$s, two $R_{24}$s or two $R_{23}$s may combine with each other to form a ring.

In foregoing formula (9), $R_{21}$ represents a hydrogen bonding group. Specific examples of the hydrogen bonding group are the same as those cited in the foregoing $R_{11}$ of the formula (1) and preferred ones are the same as cited in the foregoing formula (1). $R_{22}$, $R_{23}$, $R_{24}$ and $R_{28}$ represents a hydrogen atom or a substituent and specific examples of the substituent are the same as defined in the foregoing $R_{12}$, $R_{13}$ and $R_{14}$ of the formula (1).

In the formula (9), n21 and n23 are each an integer of 1 to 4, n24 is an integer of 1 to 3 and n25 is an integer of 1 or 2, provided that when n21, n23, n24 or n25 is 2 or more, the respective $R_{22}$, $R_{24}$, $R_{28}$ and $R_{23}$ may be the same or different, and when n21, n23, n24 or n25 is 2 or more, two $R_{22}$s, two $R_{24}$s, two $R_{28}$s or two $R_{23}$s may combine with each other to form a ring.

In foregoing formula (10), $R_{31}$ represents a hydrogen bonding group. Specific examples of the hydrogen bonding group are the same as those cited in the foregoing $R_{11}$ of the formula (1) and preferred ones are the same as cited in the foregoing formula (1).

$R_{25}$ represents a group having a Hammett substituent constant (σp) of 0.3 to 1.0. Specific examples of a group having a Hammett substituent constant (σp) of 0.3 to 1.0 are the same as cited in the foregoing $R_{25}$ of formula (8).

In the formula (10), n31 and n33 are each an integer of 1 to 4, and n35 is an integer of 1 or 2, provided that when n31, n33 or n35 is 2 or more, the respective $R_{32}$, $R_{35}$ and $R_{34}$ may be the same or different, and when n31, n33 or n35 is 2 or more, two $R_{32}$s, two $R_{35}$s or two $R_{34}$s may combine with each other to form a ring.

In foregoing formula (11), $R_{31}$, represents a hydrogen bonding group. Specific examples of the hydrogen bonding group are the same as those defined in $R_{11}$ of the foregoing formula (1) and preferred ones are also the same as cited in the foregoing formula (1). $R_{32}$, $R_{33}$, $R_{34}$, $R_{35}$ and $R_{39}$ represent a hydrogen atom or a substituent and specific examples of the substituent are the same as defined in the foregoing $R_{12}$, $R_{13}$ and $R_{14}$ of the formula (1).

In the formula (11), n31 and n33 are each an integer of 1 to 4, n34 is an integer of 1 to 3 and n35 is 1 or 2, provided that when n31, n33, n34 or n35 is 2 or more, the respective $R_{32}$, $R_{35}$, $R_{39}$ and $R_{34}$ may be the same or different, and when n31, n33, n34 or n35 is 2 or more, two $R_{32}$s, two $R_{35}$s, two $R_{39}$s or two $R_{34}$s may combine with each other to form a ring.

The dye represented by formula (2) is also preferably a dye represented by the following formula (12), and the dye represented by formula (3) is also preferably a dye represented by the following formula (13):

formula (12)

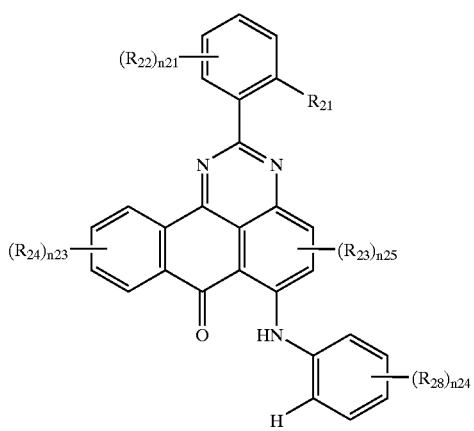

formula (13)

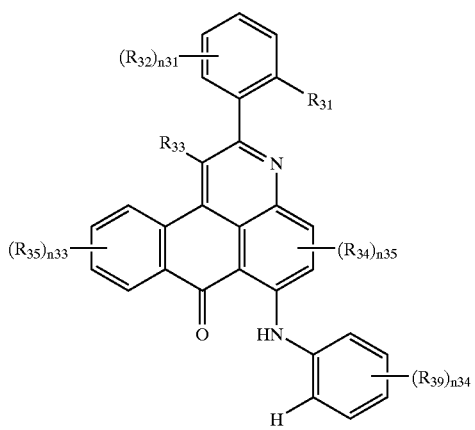

wherein $R_{21}$, and $R_{31}$ are independently a hydrogen bonding group; $R_{22}$, $R_{23}$, $R_{24}$, $R_{28}$, $R_{32}$, $R_{33}$, $R_{34}$, $R_{35}$ and $R_{39}$ are independently a hydrogen atom or a substituent; n21, n23, n24, n31, n33, and n34 are each an integer of 1 to 4; n25 and n35 is an integer of 1 or 2.

In foregoing formula (12), $R_{21}$ is a hydrogen bonding group, as cited in the foregoing $R_{21}$ of formula (8); $R_{22}$, $R_{23}$, $R_{24}$ and $R_{28}$ represent a hydrogen atom or a substituent, as defined in the foregoing $R_{22}$, $R_{23}$, $R_{24}$ and $R_{28}$ of formula (8). In formula (12), n21 and n23 are each an integer of 1 to 4, n24 is an integer of 1 to 3 and n25 is 1 or 2, provided that when n21, n23, n24 or n25 is 2 or more, the respective $R_{22}$, $R_{24}$, $R_{28}$ and $R_{23}$ may be the same or different, and when n21, n23, n24 or n25 is 2 or more, two $R_{22}$s, two $R_{24}$s, two $R_{28}$s or two $R_{23}$s may combine with each other to form a ring.

In foregoing formula (13), $R_{31}$, is a hydrogen bonding group, as defined in the foregoing $R_{31}$ of formula (11); $R_{32}$, $R_{33}$, $R_{34}$, $R_{35}$ and $R_{39}$ represent a hydrogen atom or a substituent, as defined in $R_{32}$, $R_{33}$, $R_{34}$, $R_{35}$ and $R_{39}$ of formula (11). In formula (13), n31 and n33 are each an integer of 1 to 4, n34 is an integer of 1 to 3 and n35 is 1 or 2, provided that when n31, n33, n34 or n35 is 2 or more, the respective $R_{32}$, $R_{35}$, $R_{39}$ and $R_{34}$ may be the same or different, and when n31, n33, n34 or n35 is 2 or more, two $R_{32}$s, two $R_{35}$s, two $R_{39}$s or two $R_{34}$s may combine with each other to form a ring.

Specific examples of the foregoing dyes of this invention are shown below but the invention is by no means limited to these.

In the following formulas, M represents a cation, such as alkali metal salts (e.g., sodium, potassium and lithium salts), alkaline earth metal salts (e.g., ½ calcium salt), ammonium salt, and salts of various amines; n is an integer of 1 to 5.

Specific examples of various amines include alkanolamines having 1 to 4 carbon atoms, such as monoethanolamine, diethanolamine, triethanolamine, monopropanolamine, dipropanolamine, and tripropanolamine. To obtain salts of sulfonic acid derivatives of the dyes represented by the foregoing formulas (1) through (13), for example, an obtained crystalline sodium salt is dissolved in water, acidified by adding an acid, if necessary, is filtered and obtained cakes are again dissolved in water. Further thereto, potassium hydroxide, lithium hydroxide, ammonia water or an alkanolamine such as diethanolamine or triethanolamine is added to obtain potassium salt, lithium salt, ammonium salt, diethanolamine or triethanolamine salt.

(A-1)

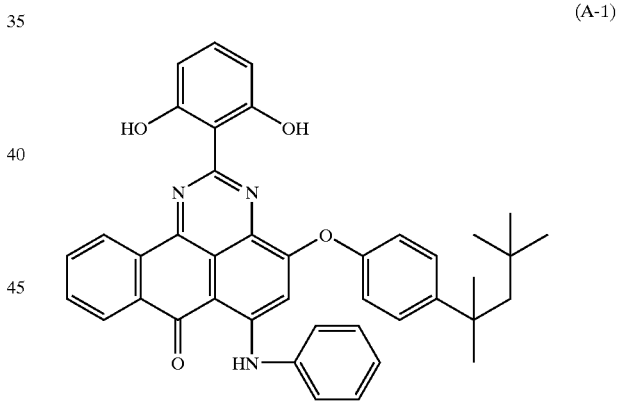

(A-2)

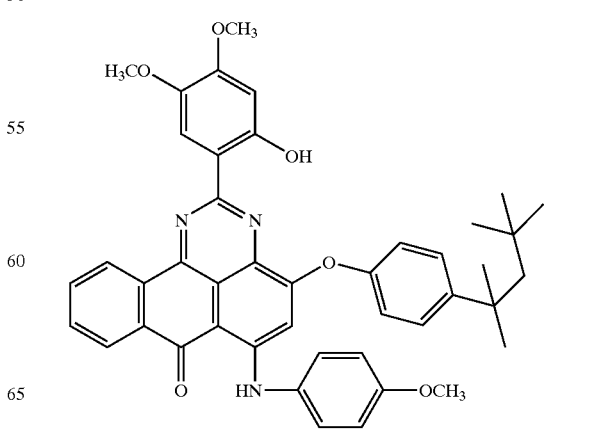

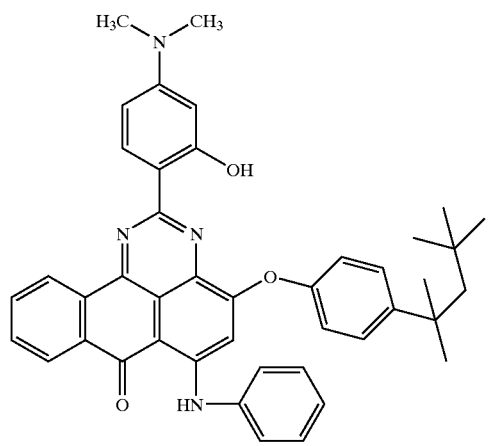
(A-3)
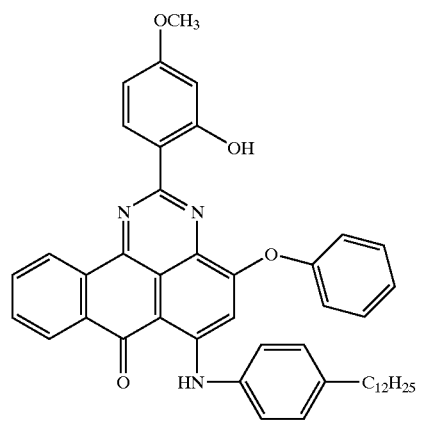
(A-6)
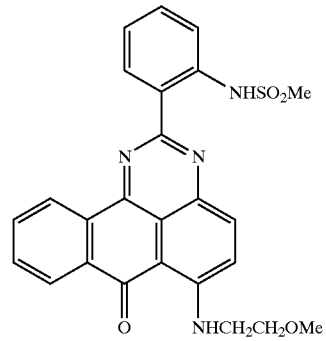
(A-4)
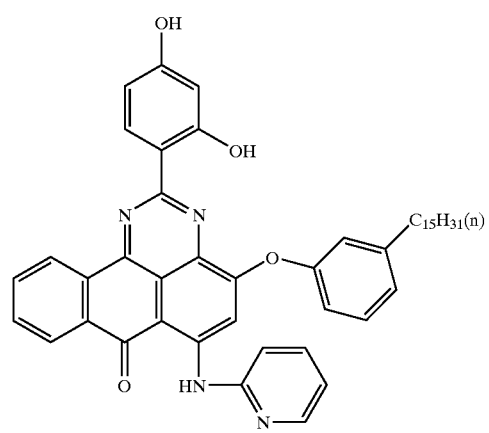
(A-7)
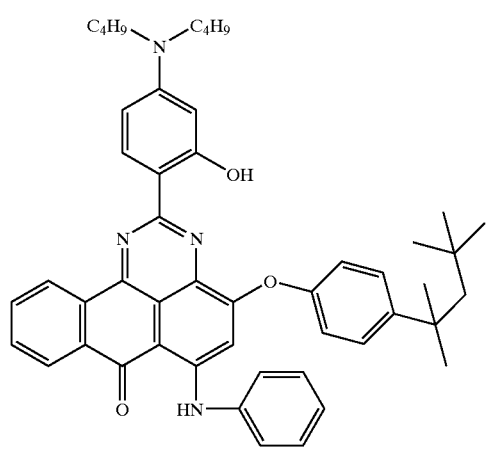
(A-5)
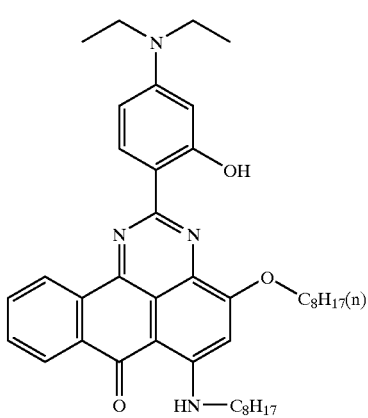
(A-8)

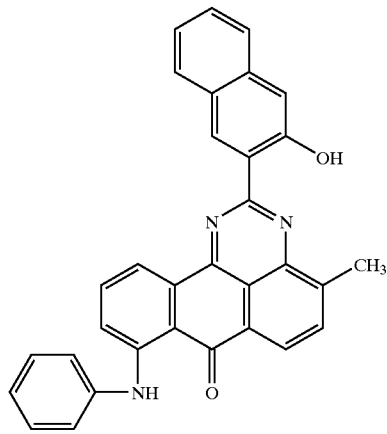
(A-9)
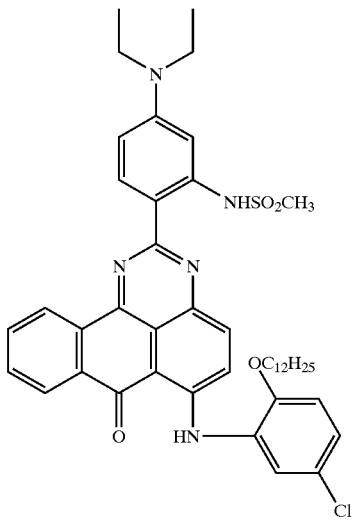
(A-12)
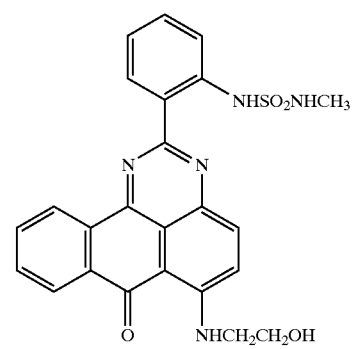
(A-10)
(A-13)
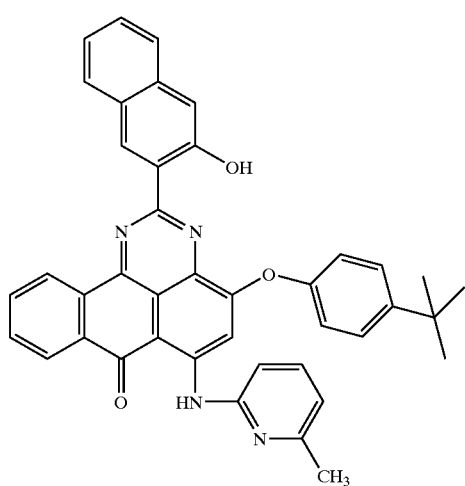
(A-11)
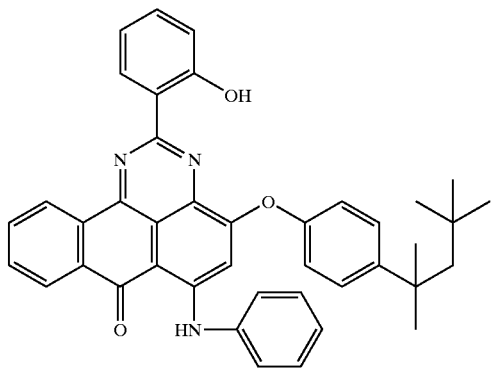
(A-14)

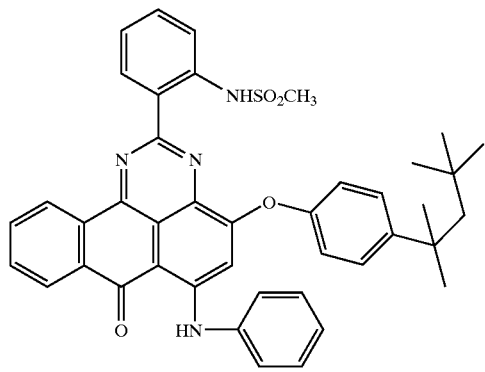
(A-15)
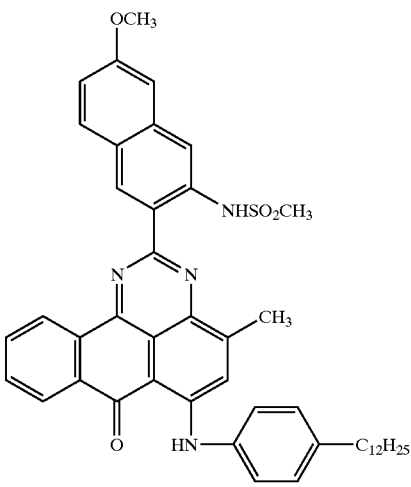
(A-18)
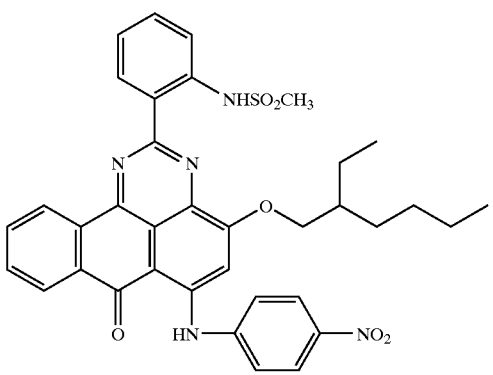
(A-16)
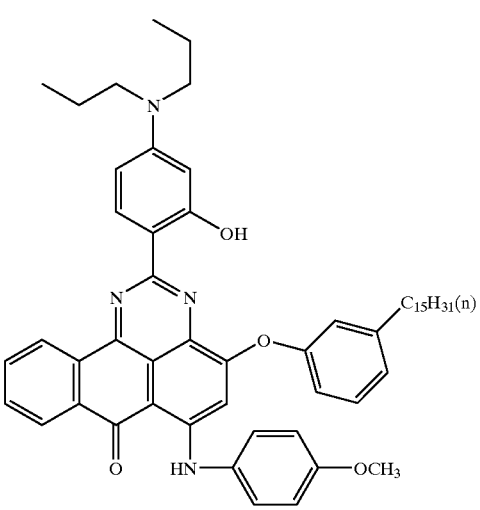
(A-19)
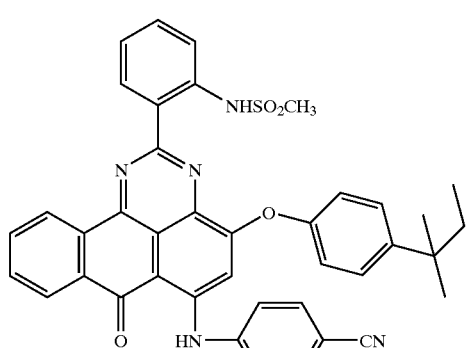
(A-17)
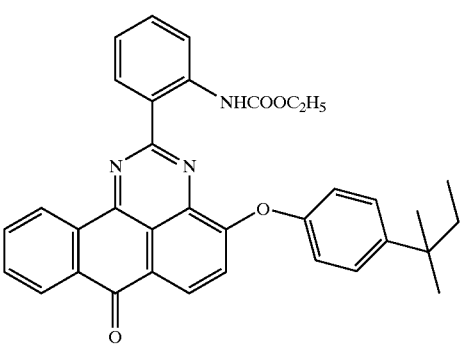
(A-20)

-continued
(A-21)
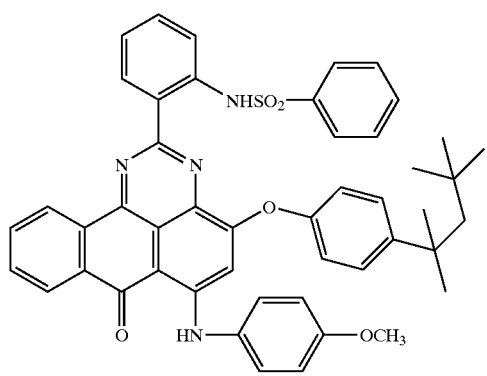
(A-22)
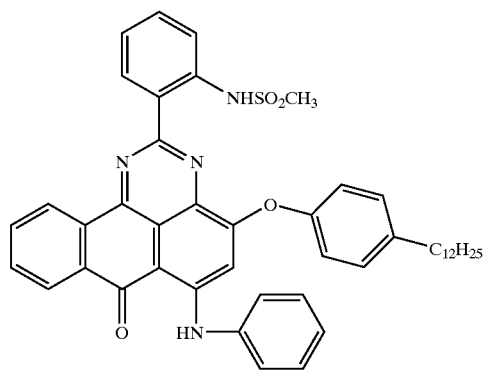
(A-23)
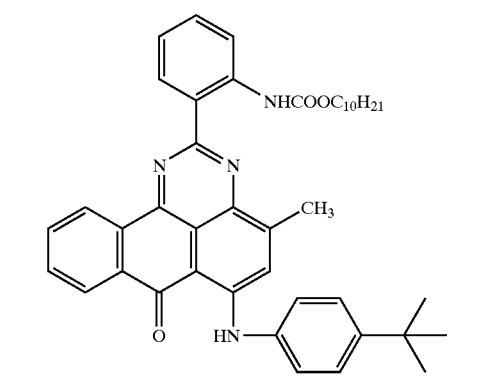
(A-24)
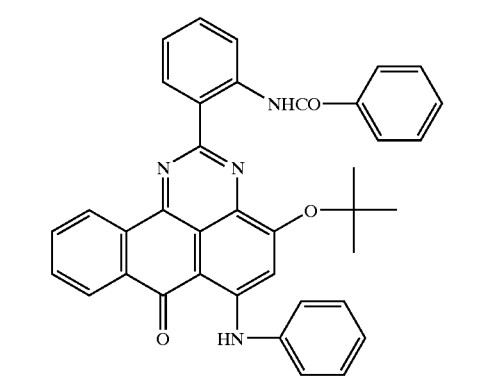
-continued
(A-25)
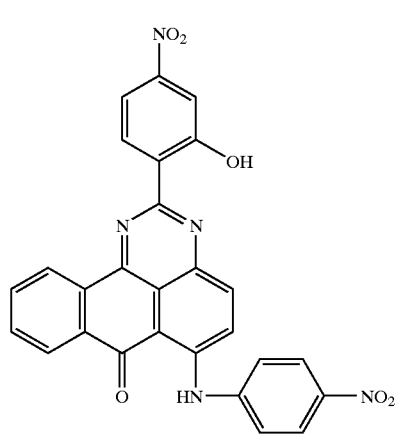
(A-26)
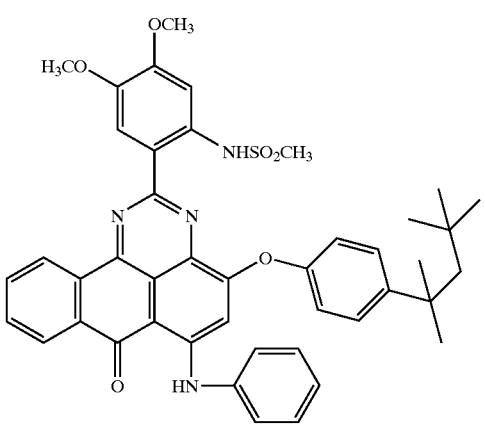
(A-27)

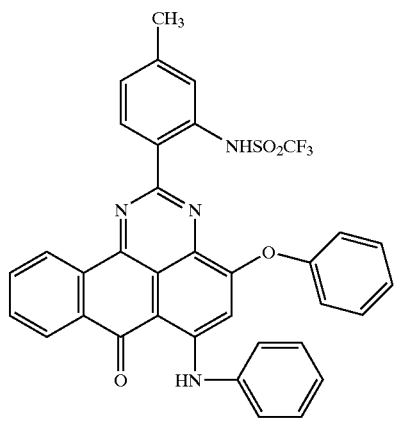
(A-28)
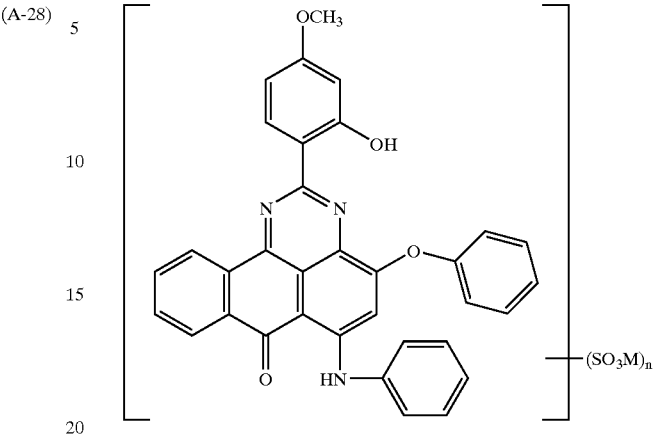
(A-31)
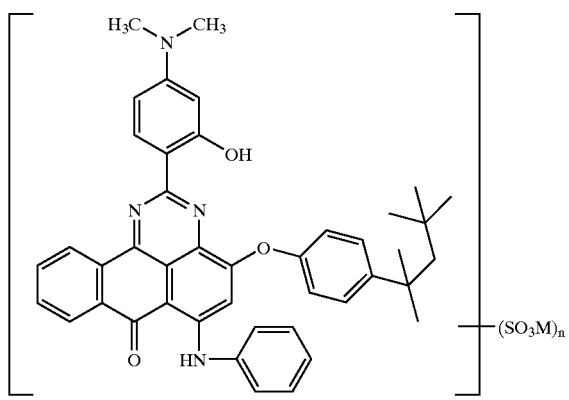
(A-29)
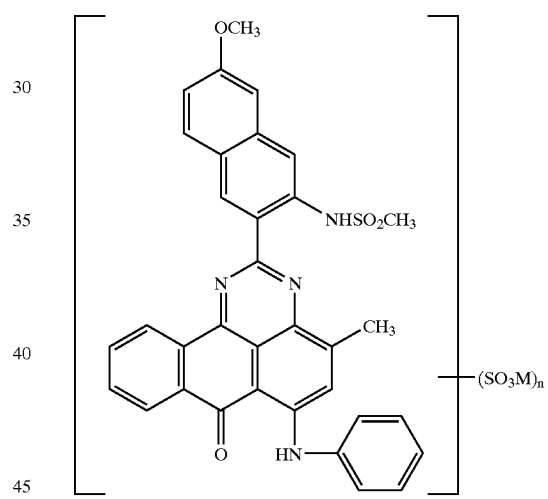
(A-32)
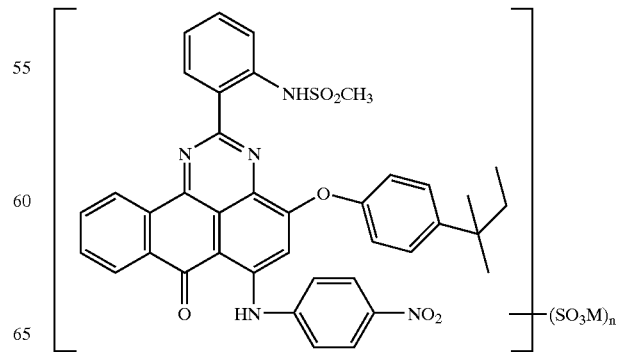
(A-30)
(A-33)

-continued
(A-34)
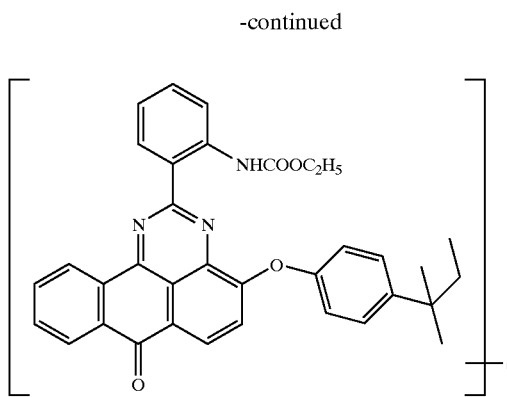
(A-35)
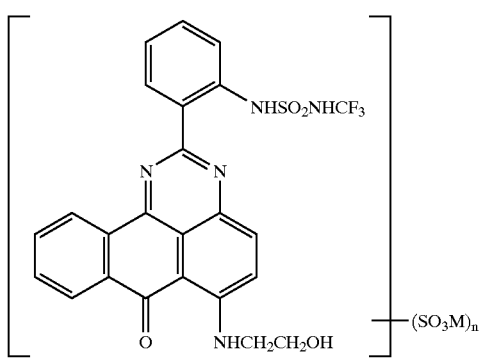
(A-36)
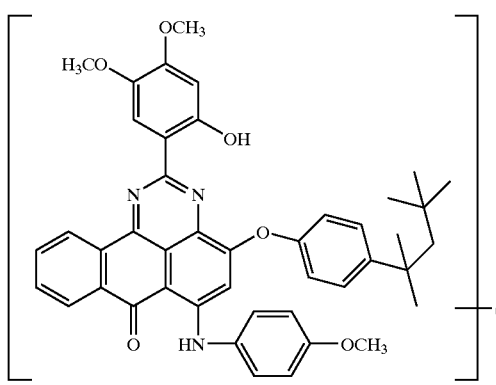
(A-37)
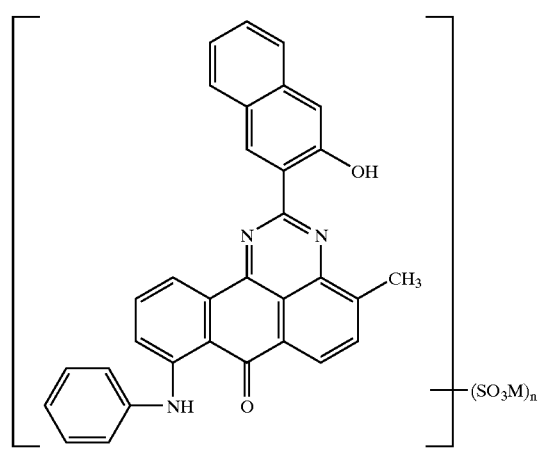
-continued
(A-38)
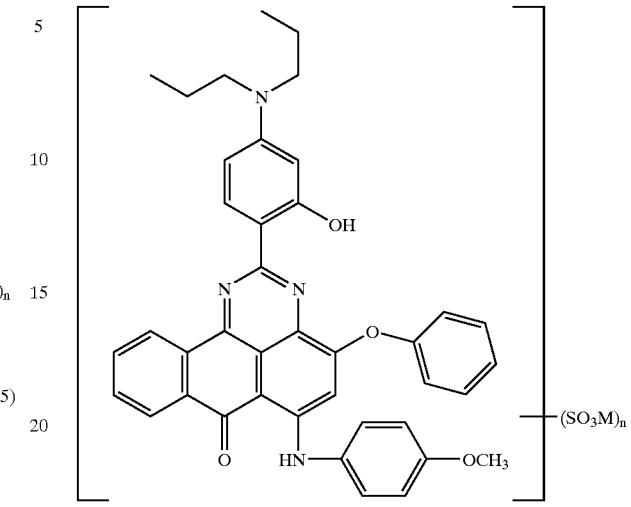
(A-39)
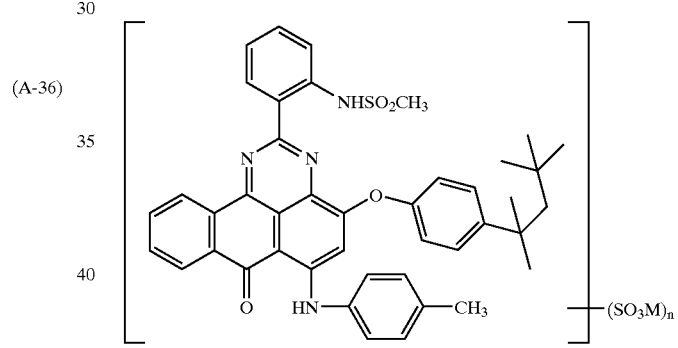
(A-40)
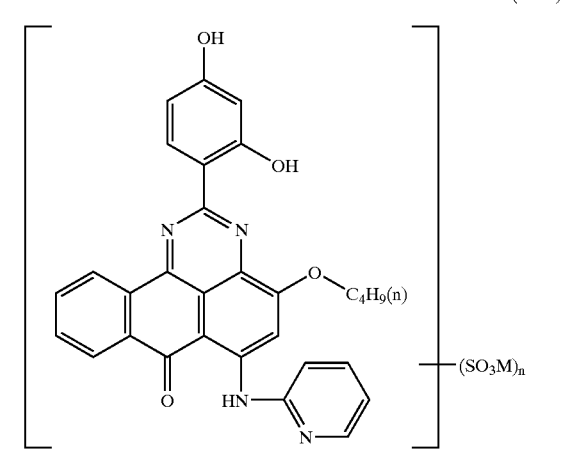

(A-41)
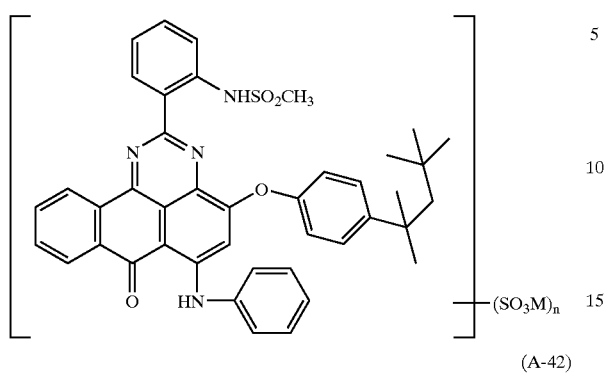
(A-42)
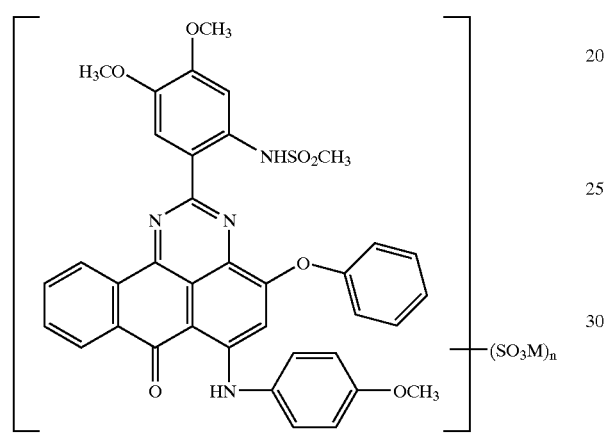
(A-43)
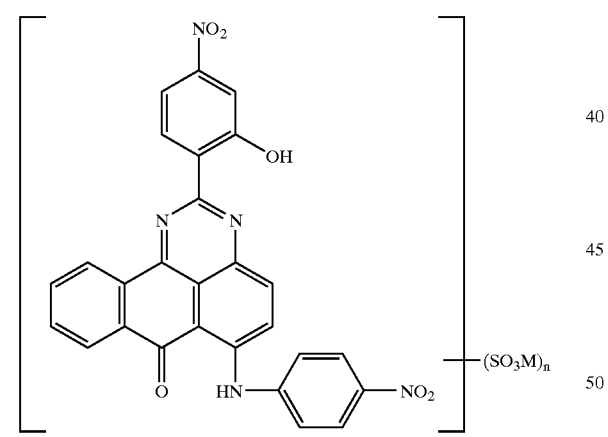
(A-44)
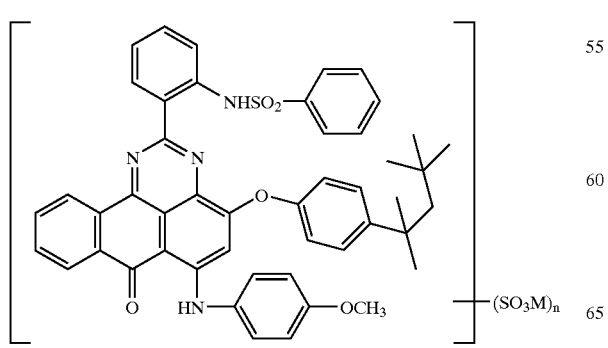
(A-45)
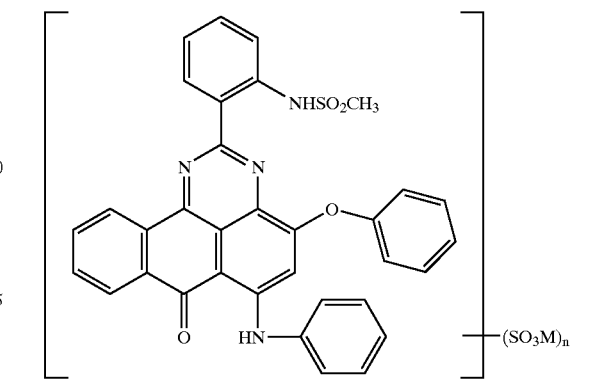
(A-46)
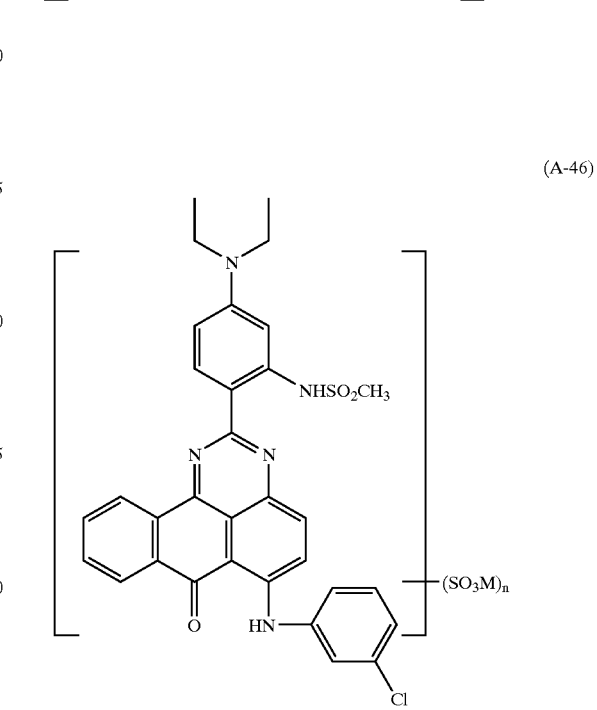
(A-47)
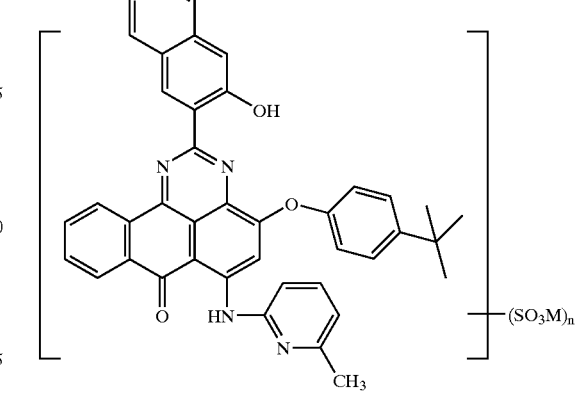

-continued
(A-48)
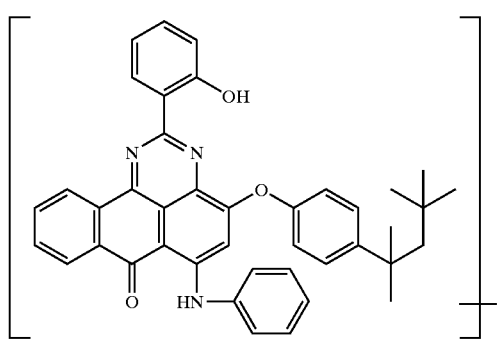
(A-49)
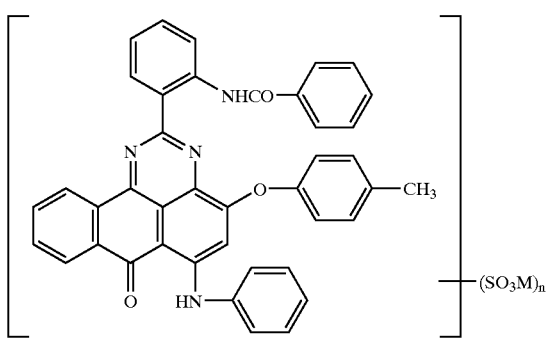
(A-50)
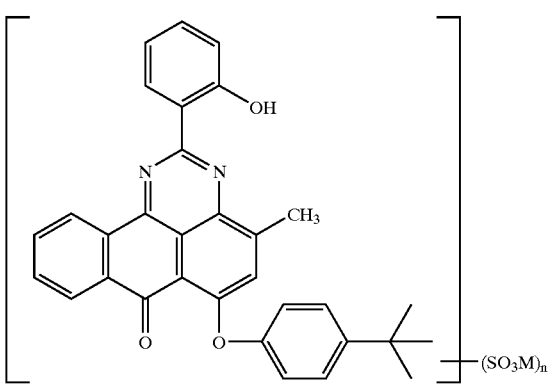
(A-51)
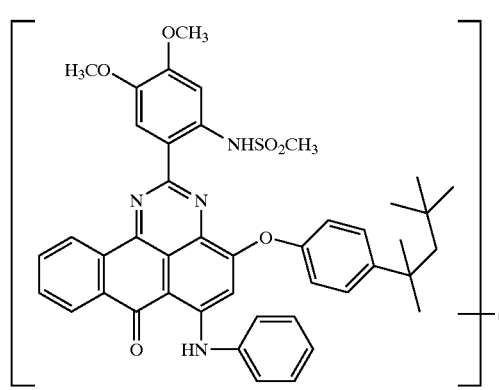
-continued
(A-52)
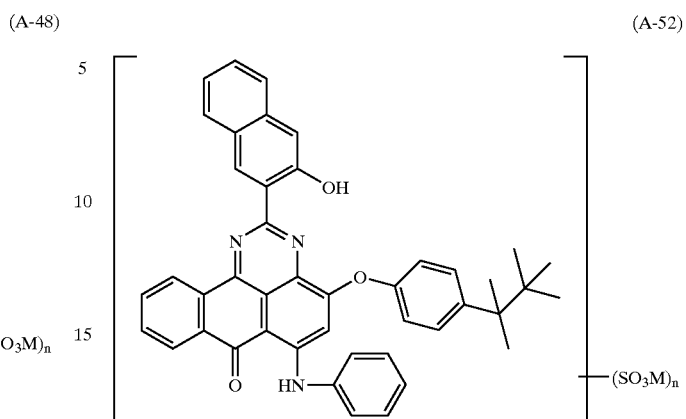
(A-53)
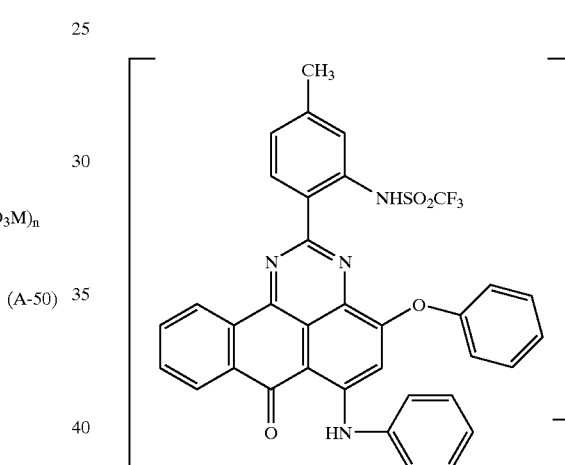
(A-54)
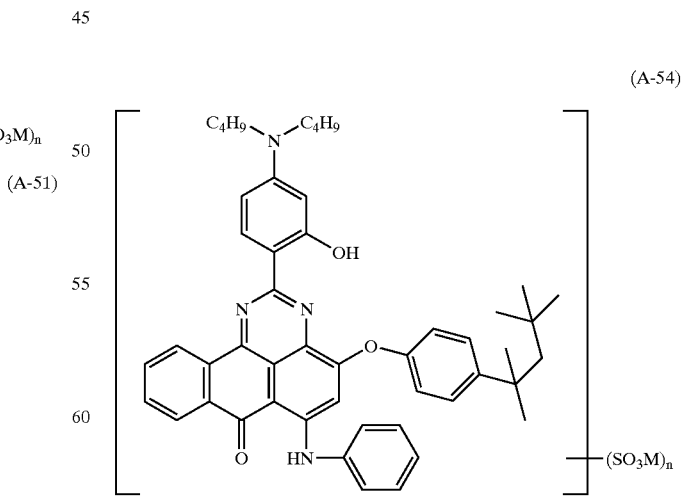

-continued
(A-55)
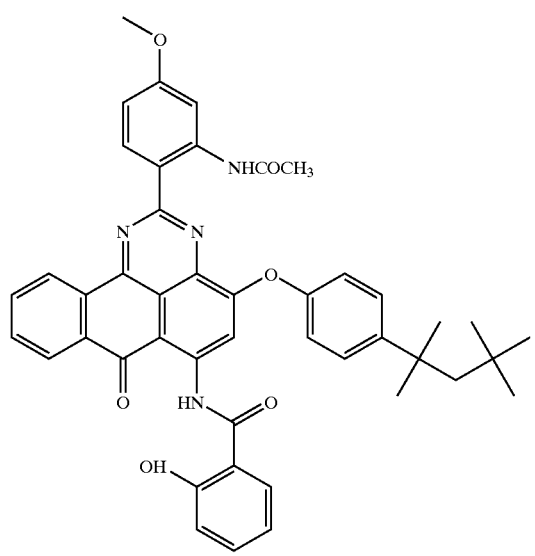
(A-56)
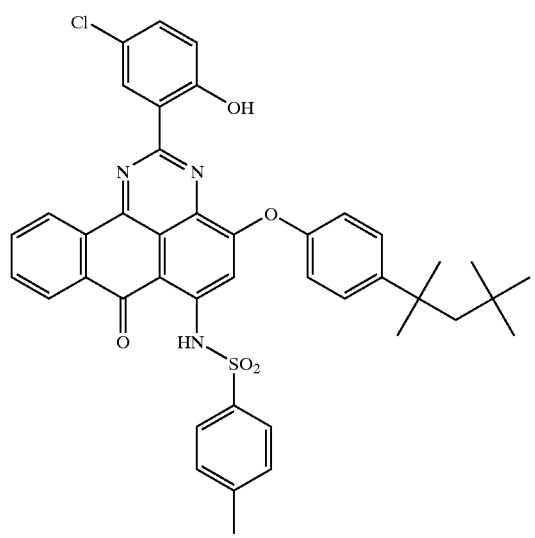
(A-57)
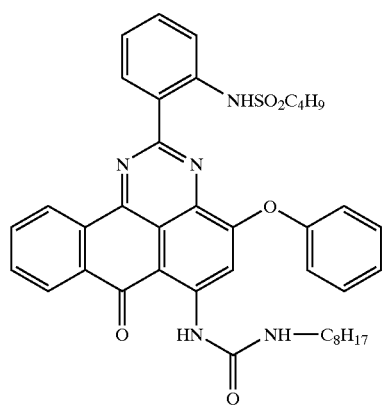
-continued
(A-58)
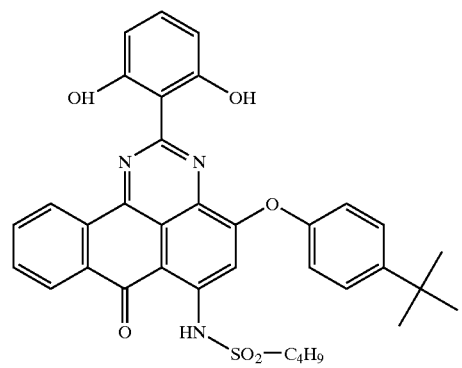
(A-59)
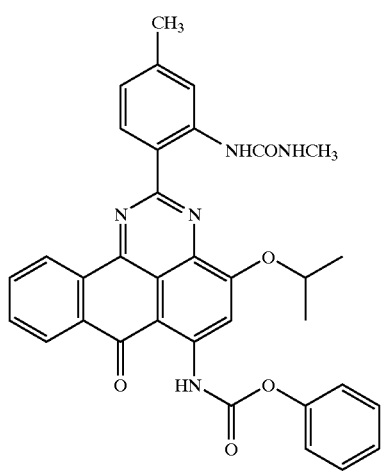
(A-60)
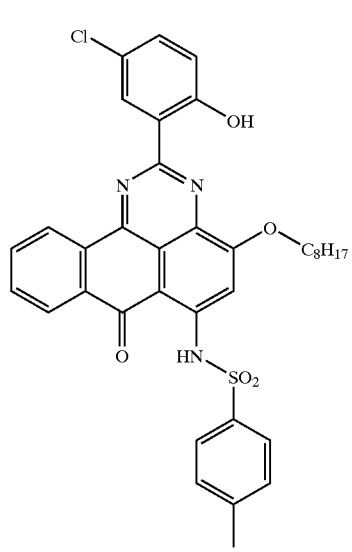

-continued
(A-61)
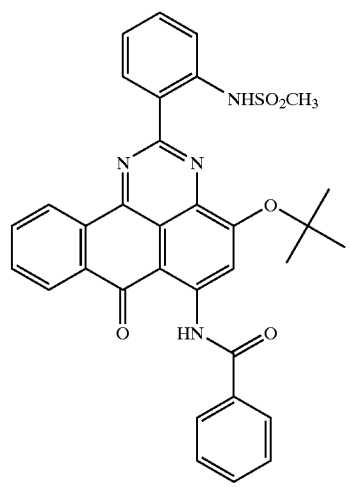
(A-62)
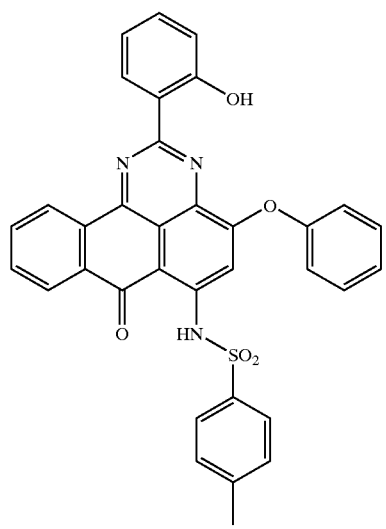
(A-63)
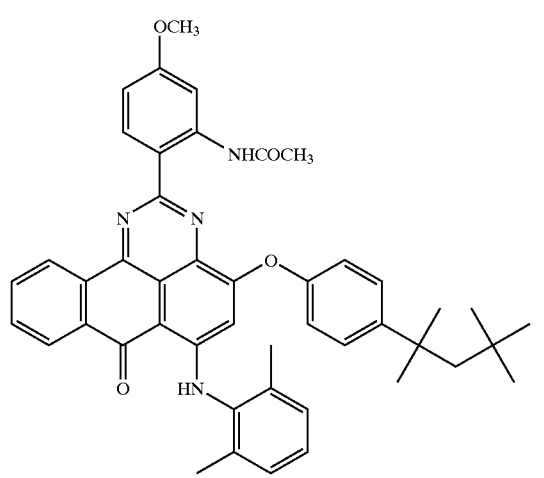
(A-64)
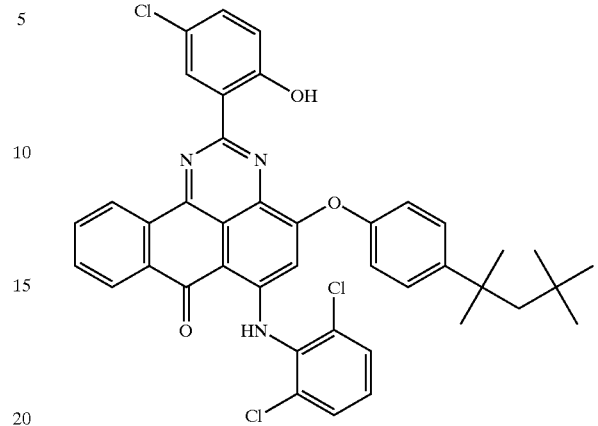
(A-65)
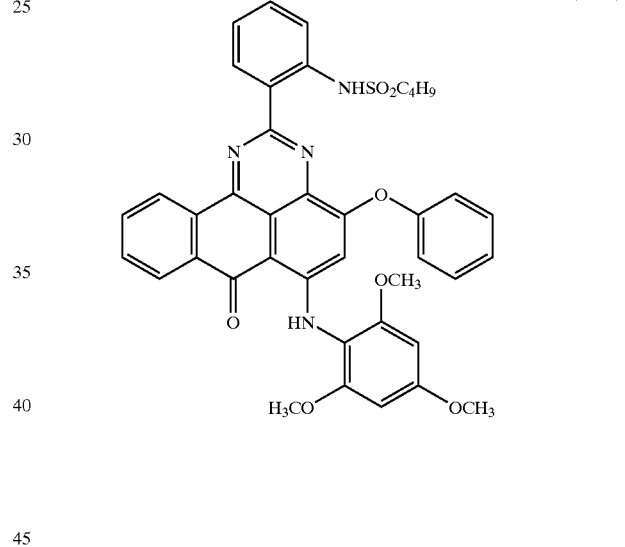
(A-66)
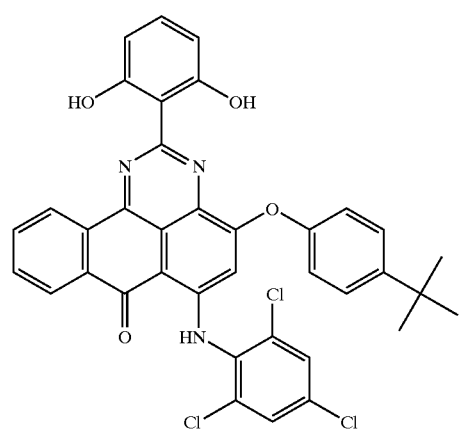

(A-67)
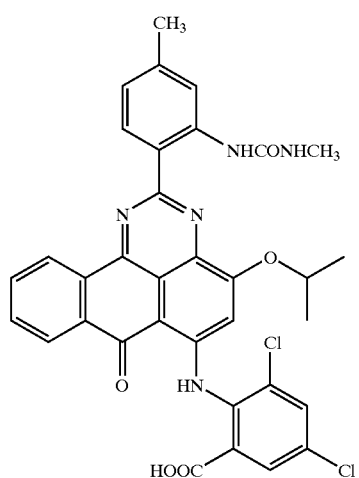
(A-68)
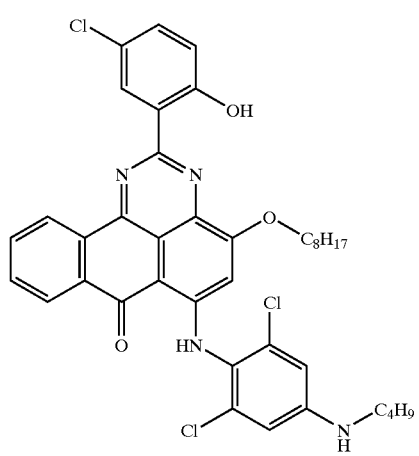
(A-69)
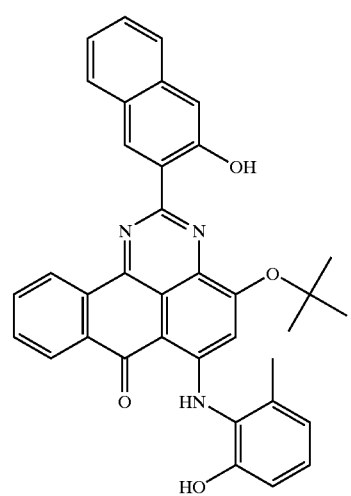
(A-70)
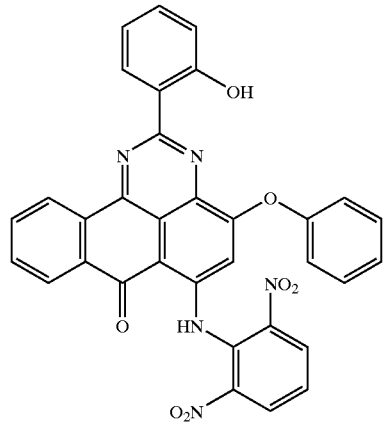
(A-71)
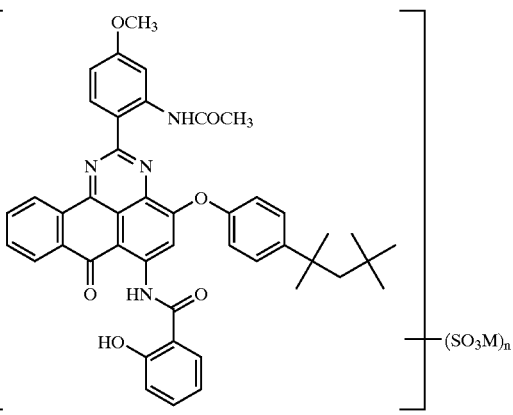
(A-72)
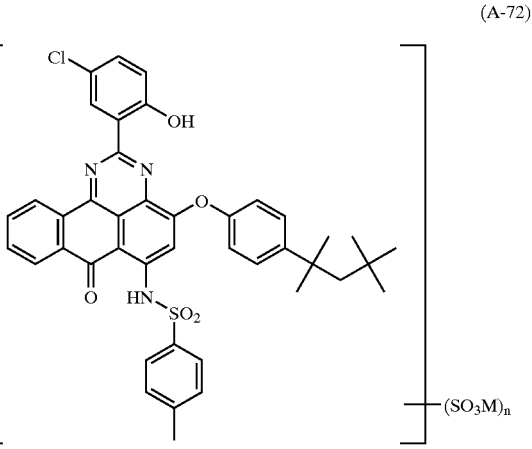

(A-73)
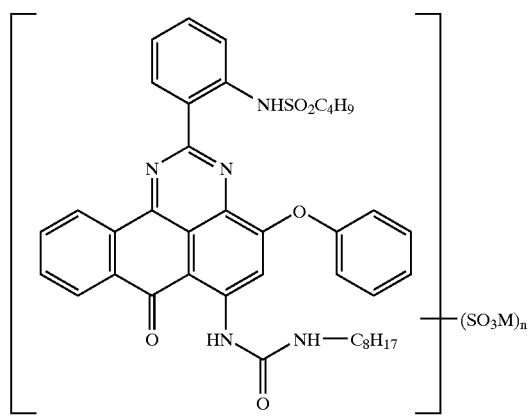
(A-74)
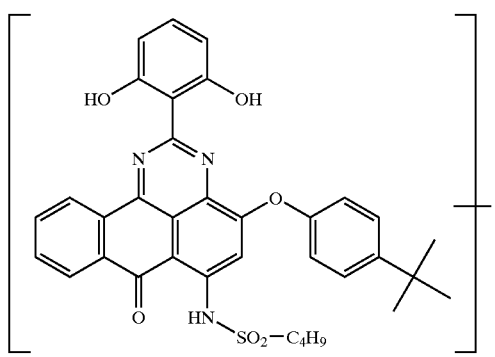
(A-75)
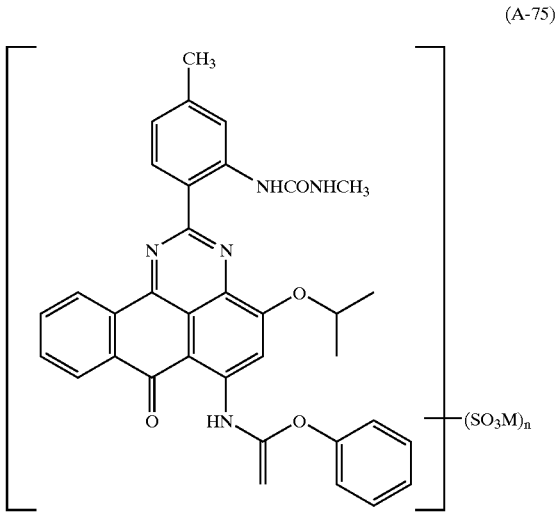
(A-76)
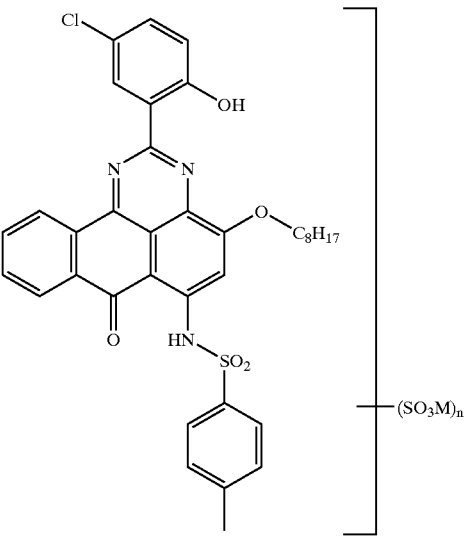
(A-77)
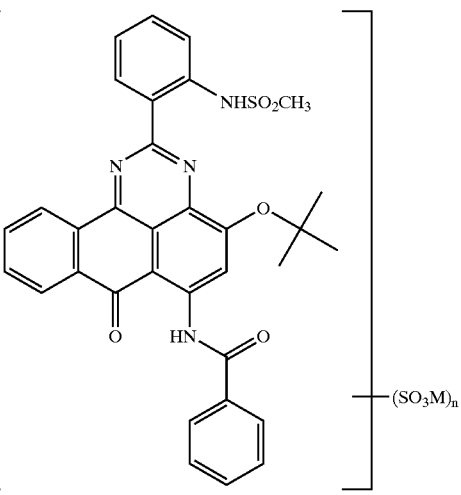
(A-78)
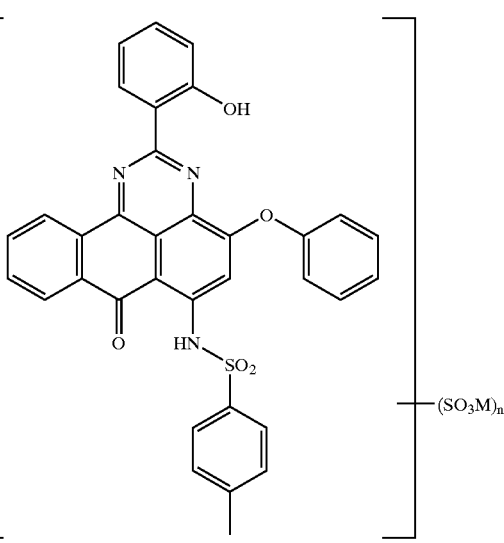

-continued
(A-79)
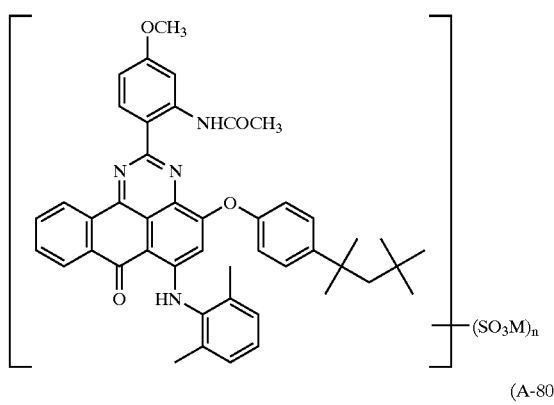
(A-80)
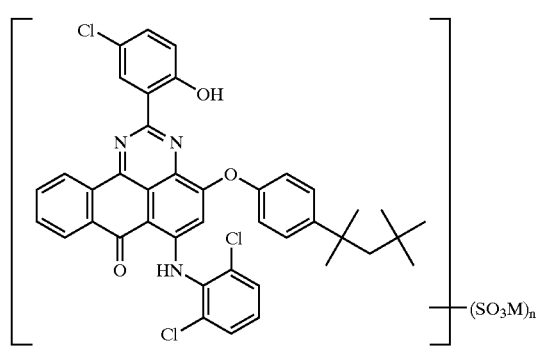
(A-81)
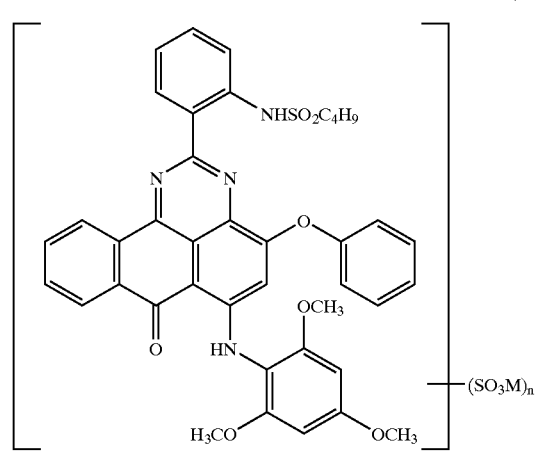
(A-82)
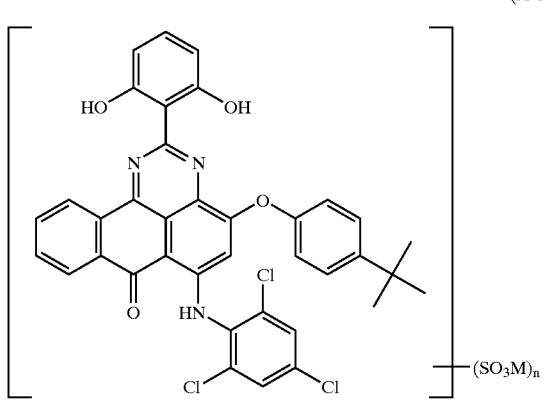
-continued
(A-83)
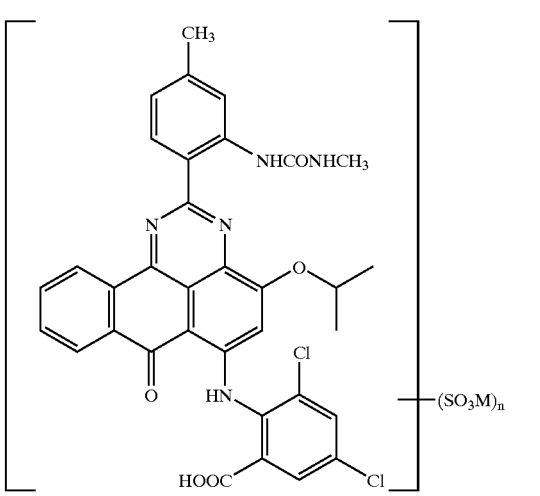
(A-84)
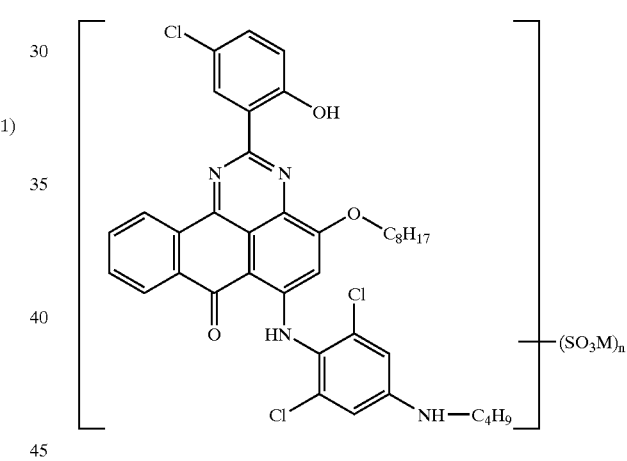
(A-85)
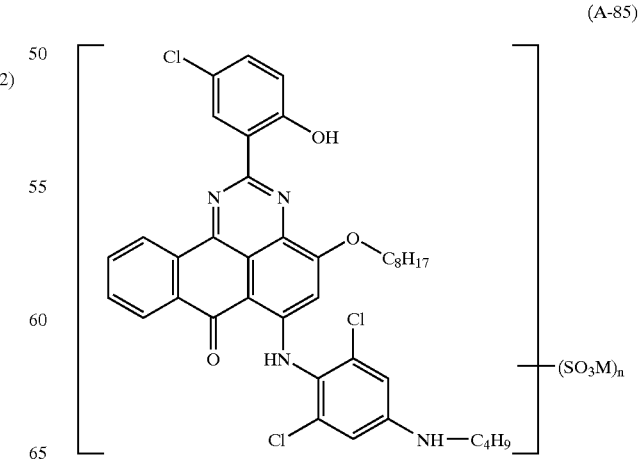

-continued
(A-86)
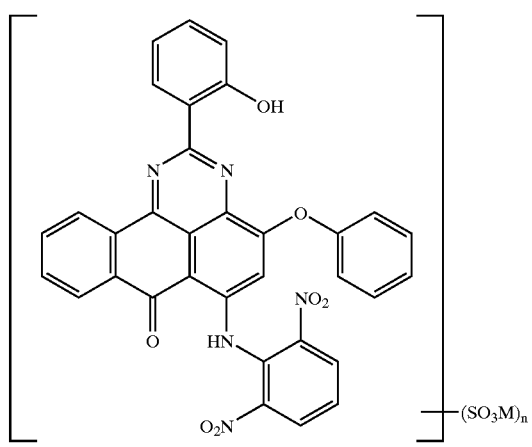
(A-89)
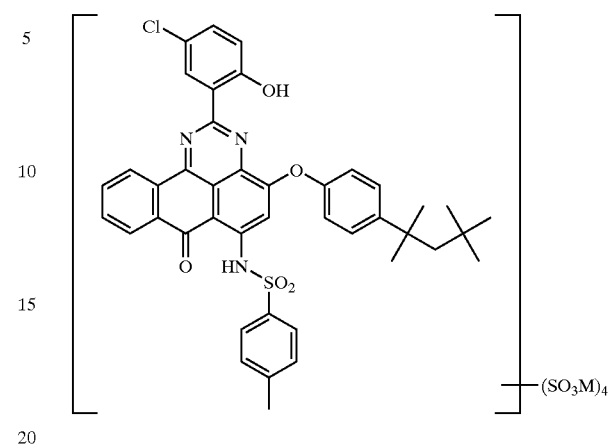
(A-87)
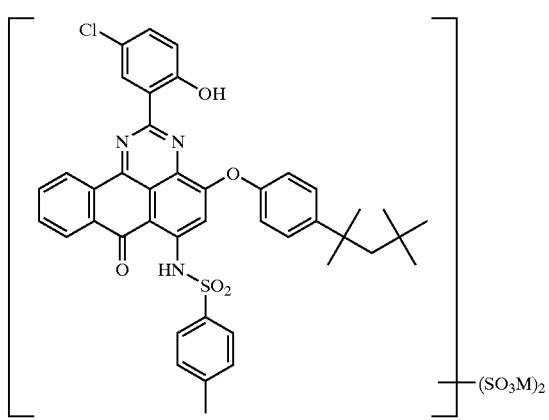
(A-90)
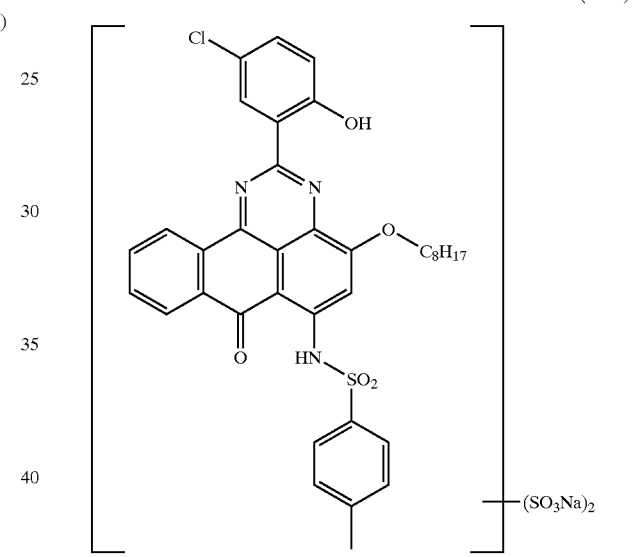
(A-88)
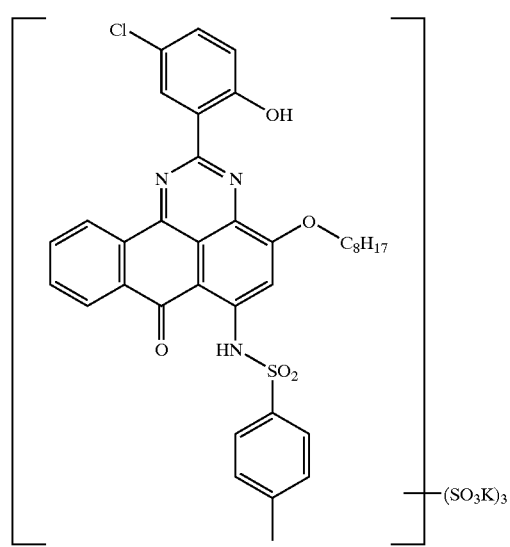
(A-91)
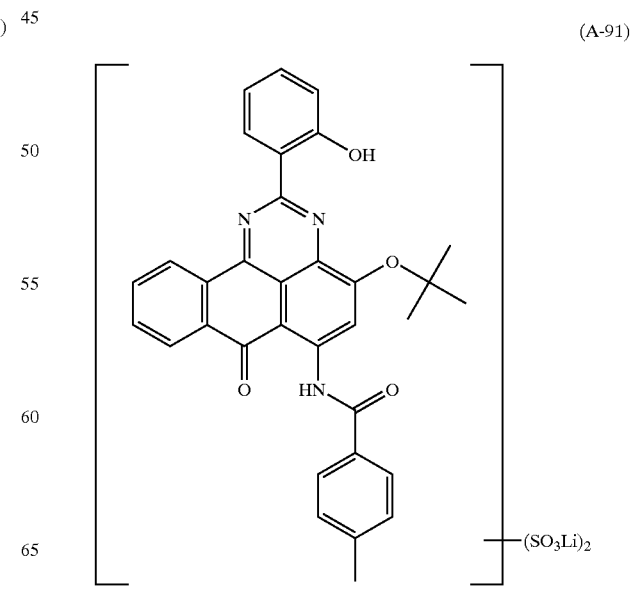

-continued
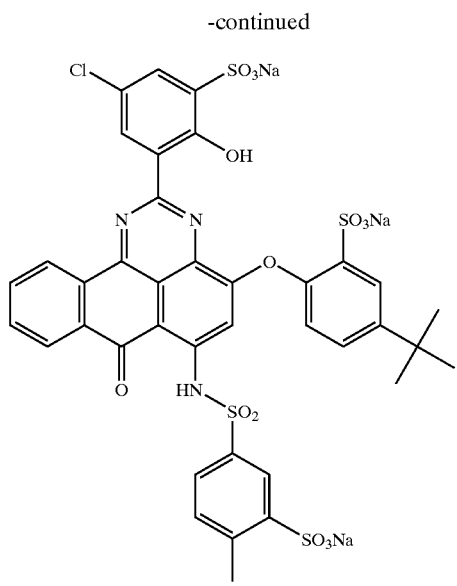
(A-92)
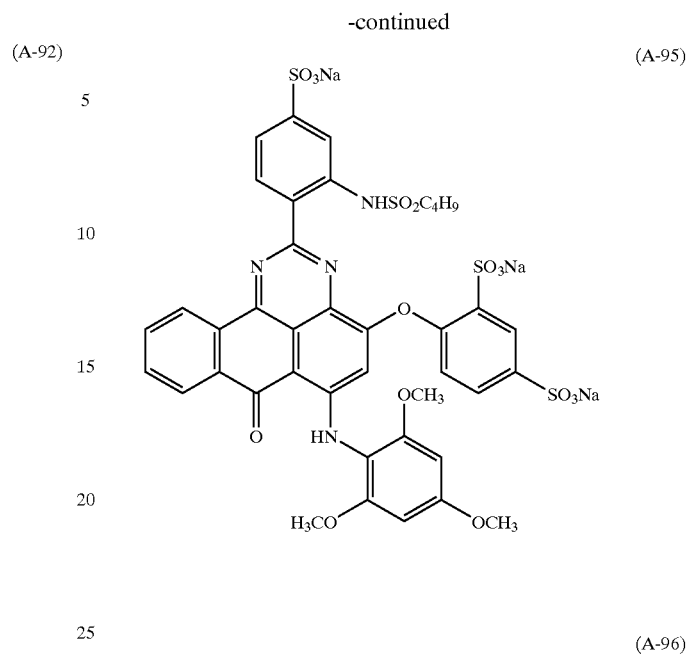
(A-95)
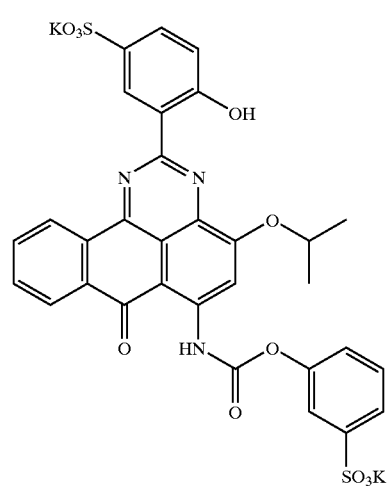
(A-93)
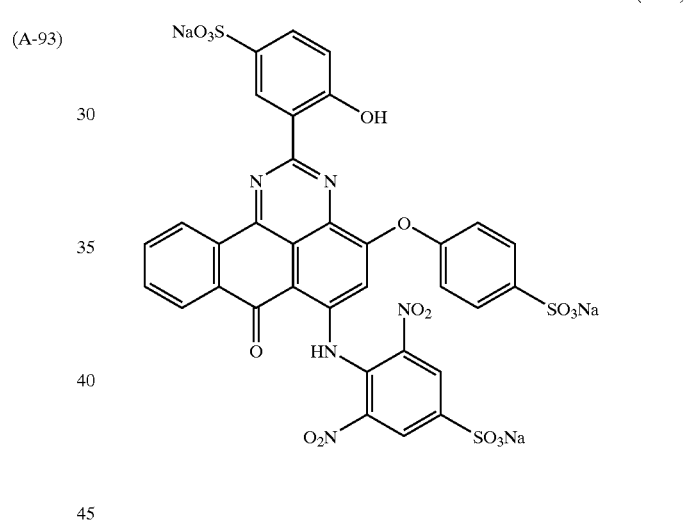
(A-96)
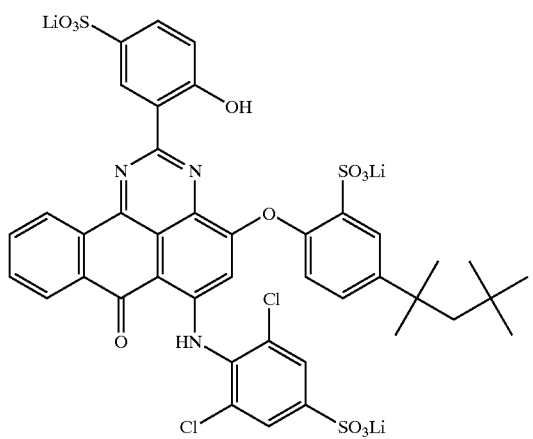
(A-94)
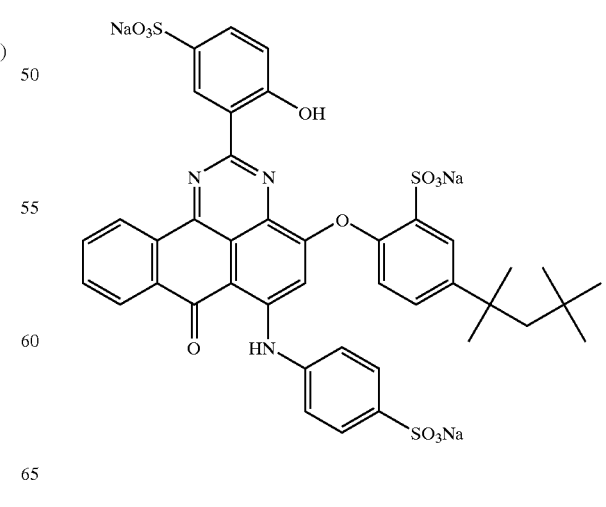
(A-97)

-continued
(A-98)
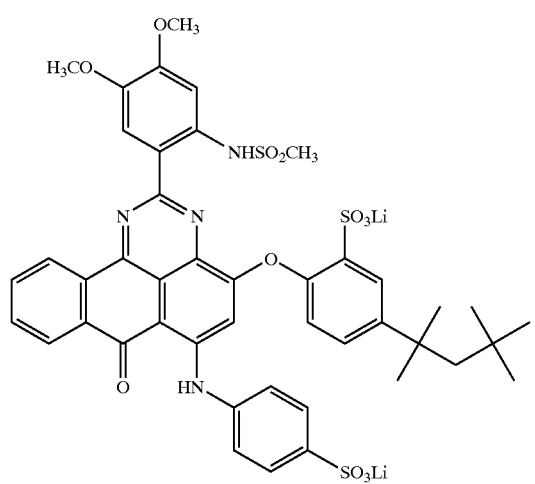
(B-1)
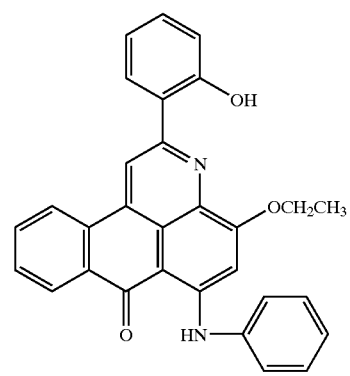
(B-2)
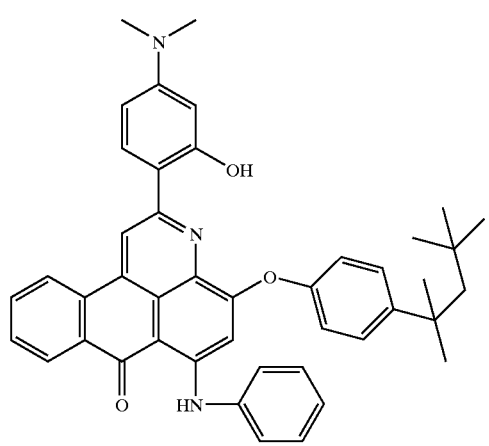
-continued
(B-3)
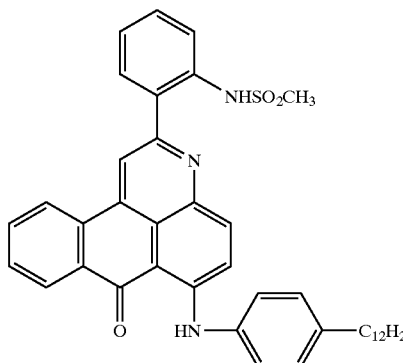
(B-4)
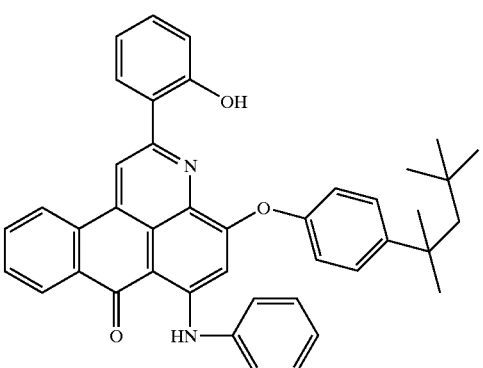
(B-5)
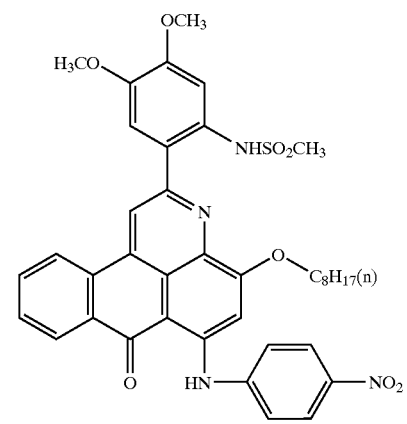
(B-6)
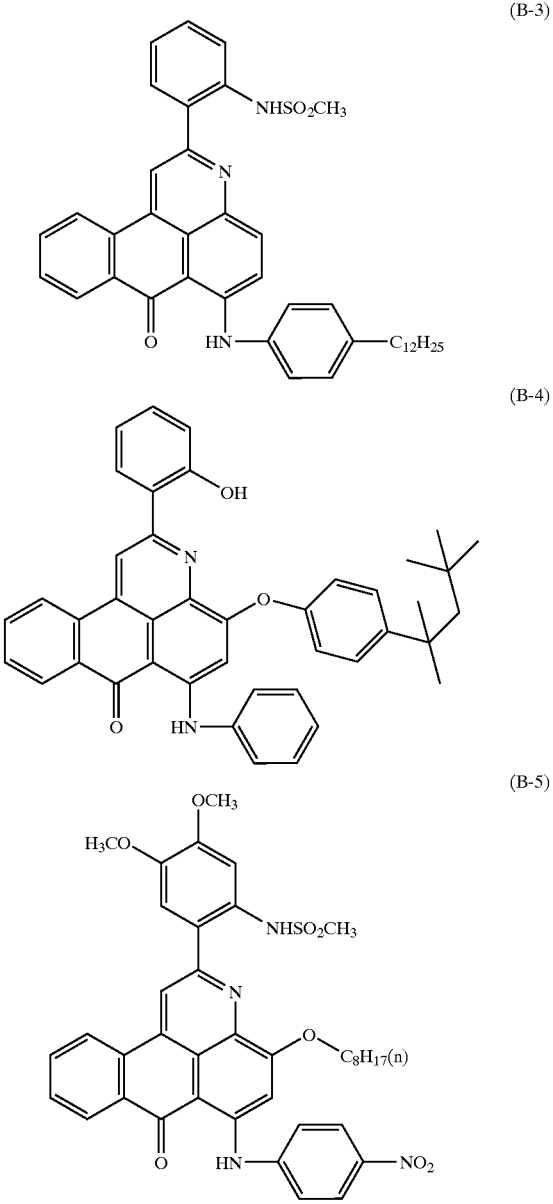

-continued
(B-7)
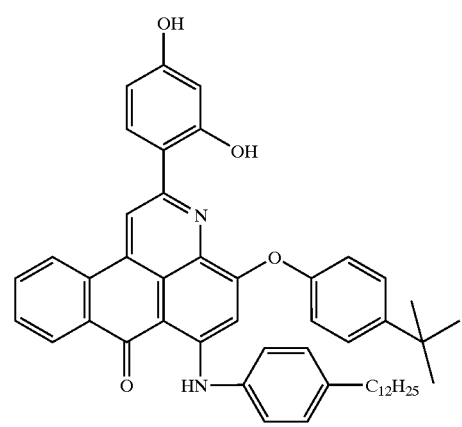
(B-8)
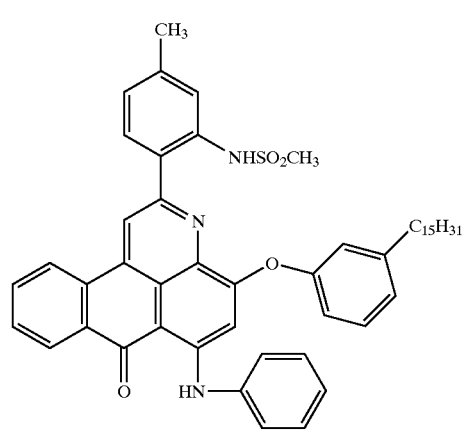
(B-9)
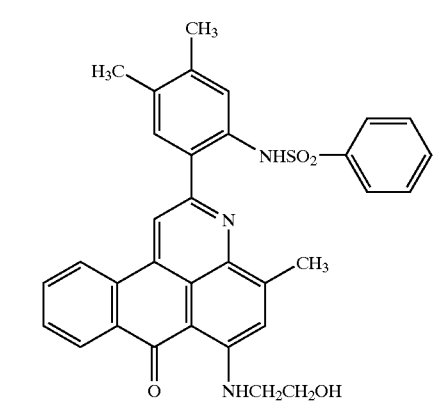
(B-10)
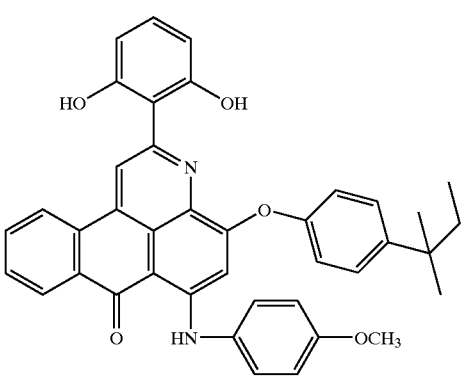
-continued
(B-11)
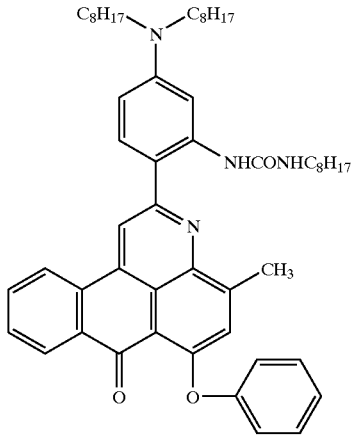
(B-12)
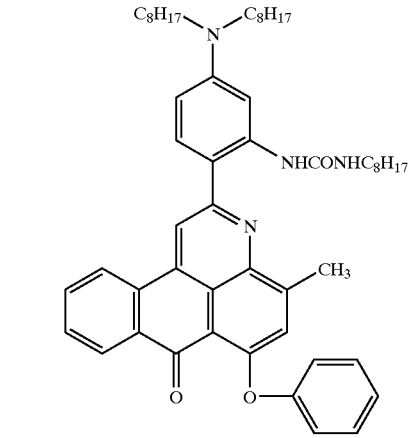
(B-13)
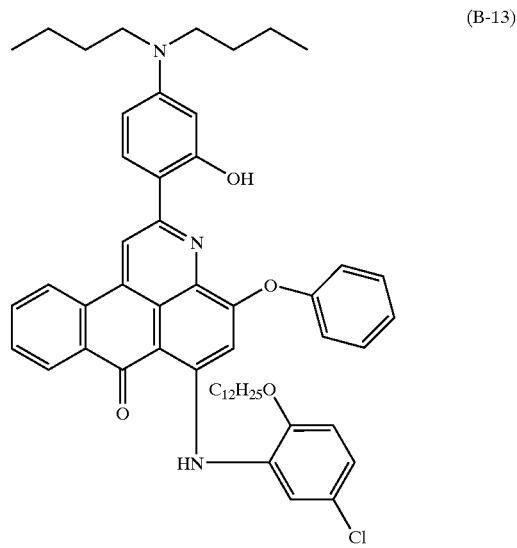

-continued
(B-14)
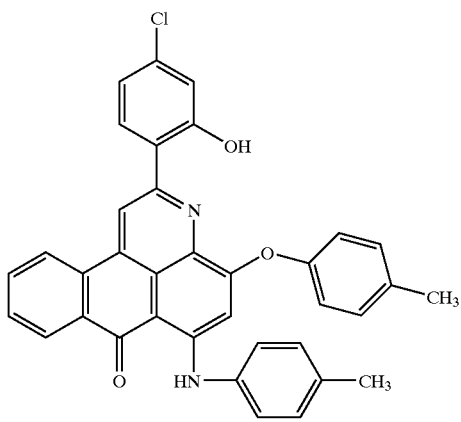
(B-15)
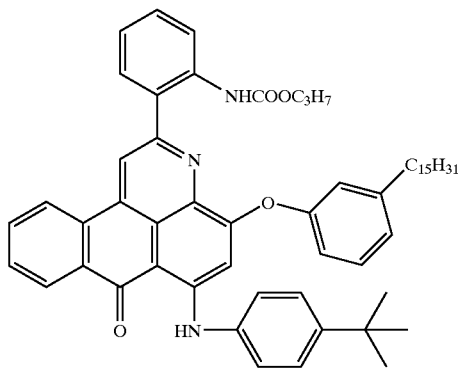
(B-16)
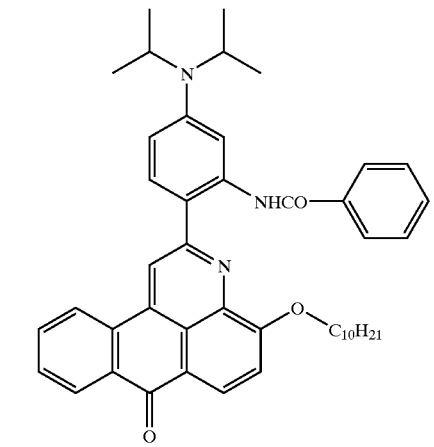
(B-17)
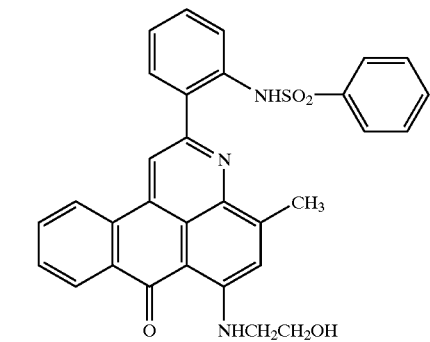
-continued
(B-18)
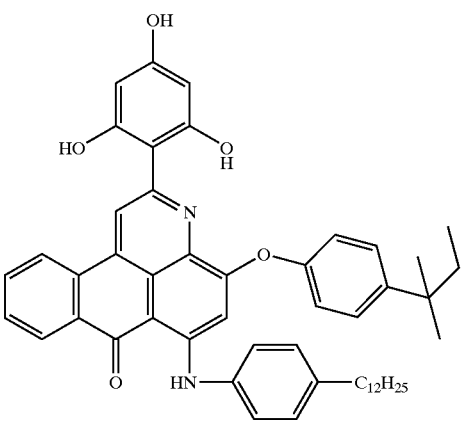
(B-19)
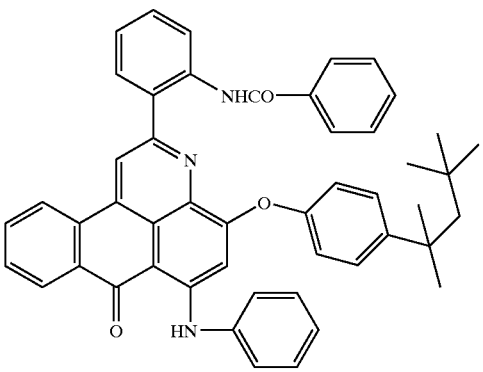
(B-20)
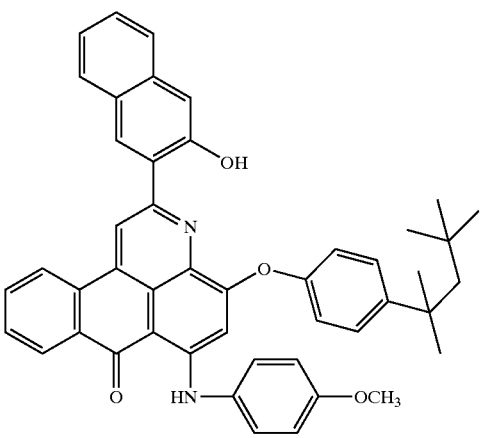

-continued
(B-21)
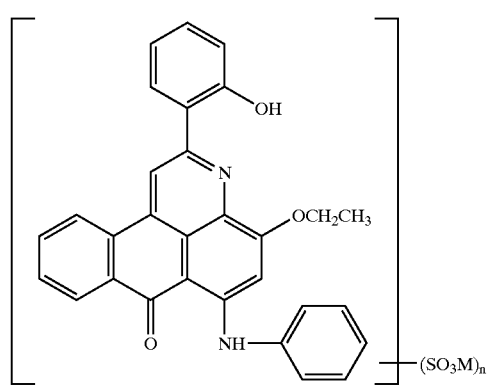
(B-22)
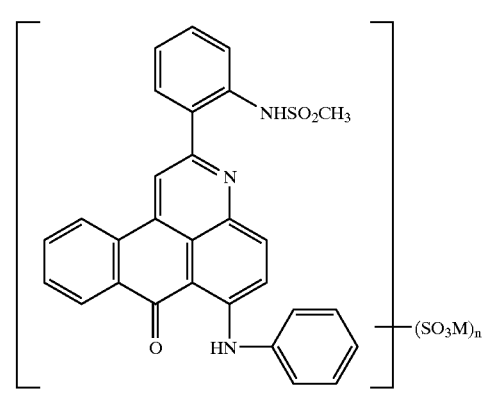
(B-23)
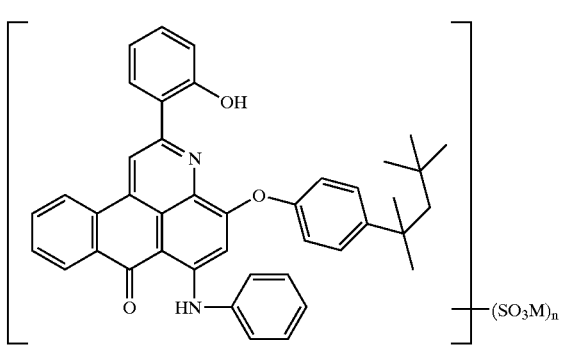
(B-24)
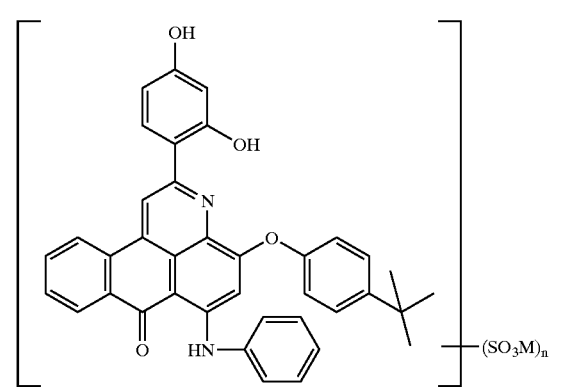
(B-25)
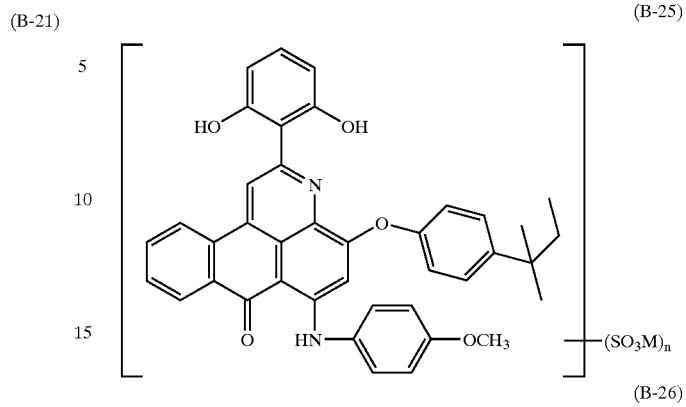
(B-26)
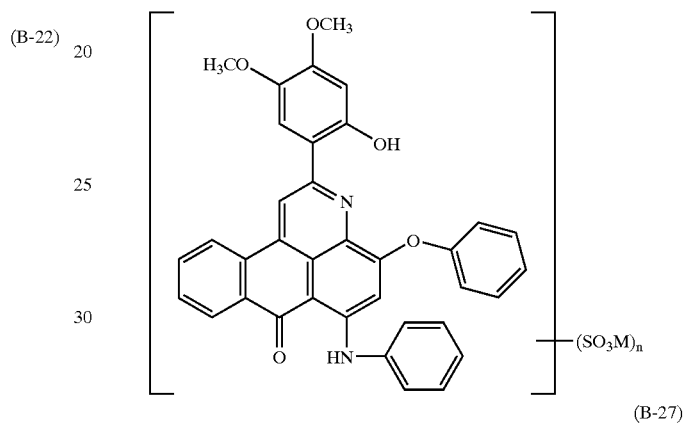
(B-27)
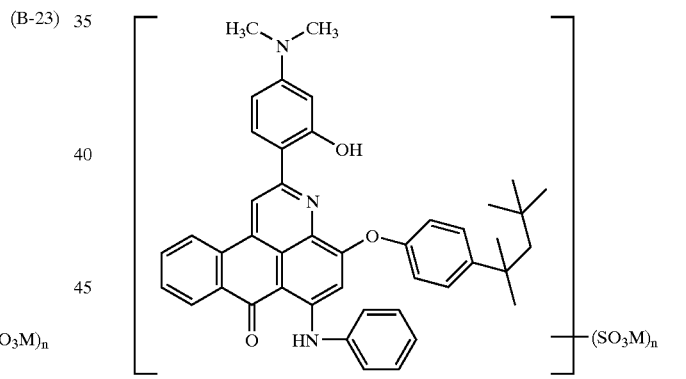
(B-28)
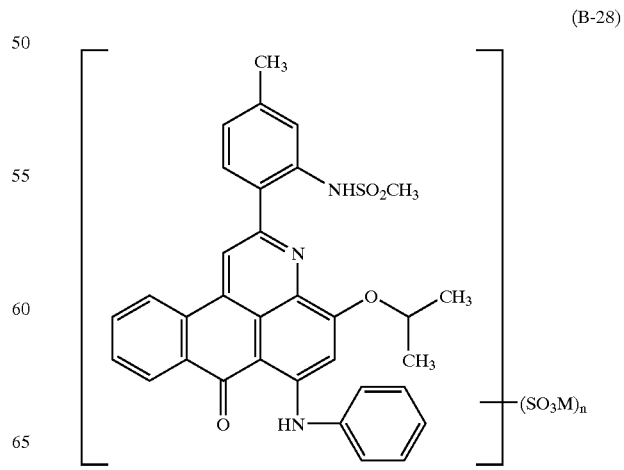

-continued
(B-29)
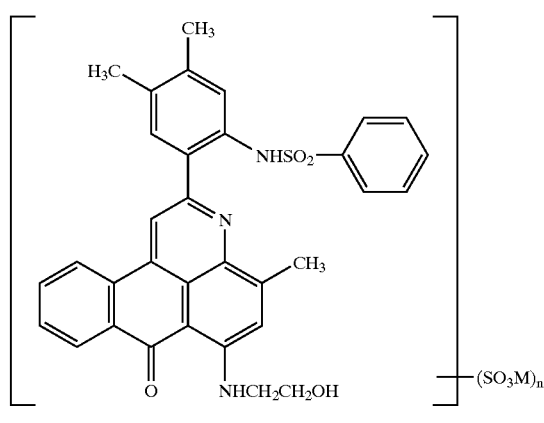
(B-32)
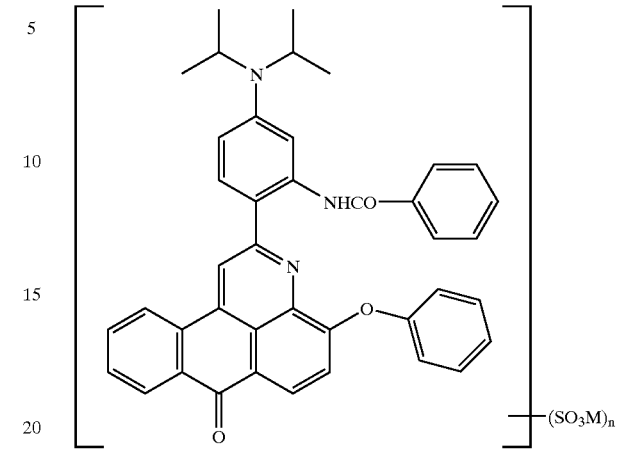
(B-30)
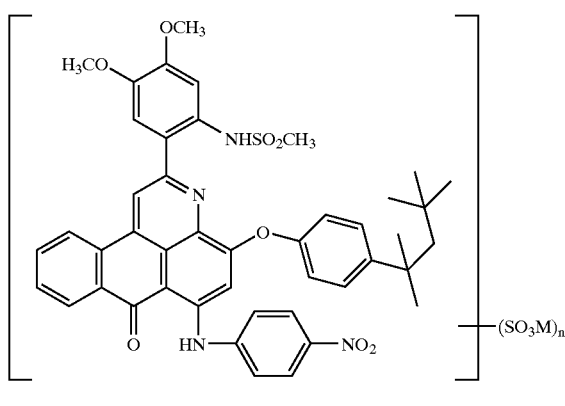
(B-33)
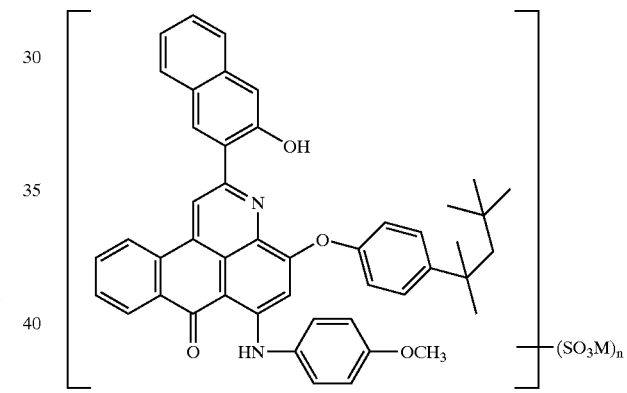
(B-31)
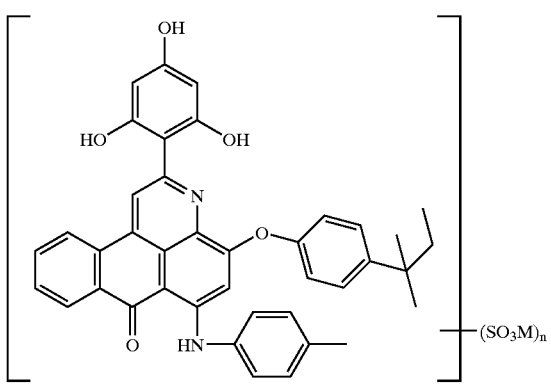
(B-34)
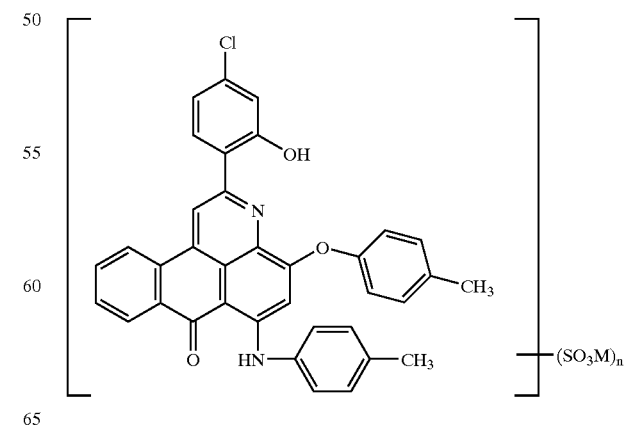

-continued
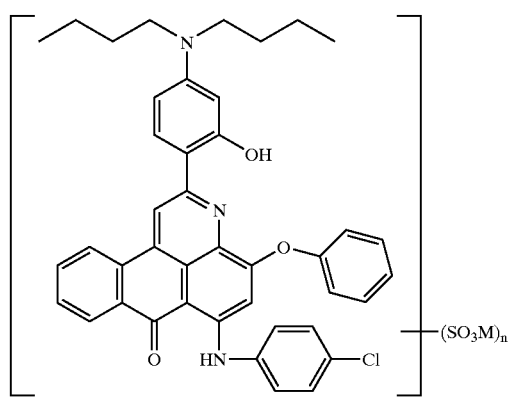
(B-35)
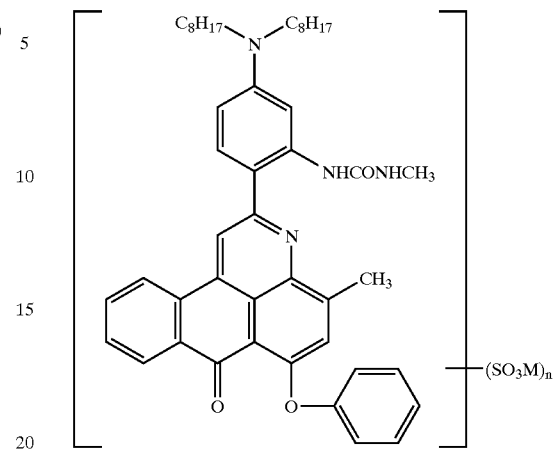
(B-38)
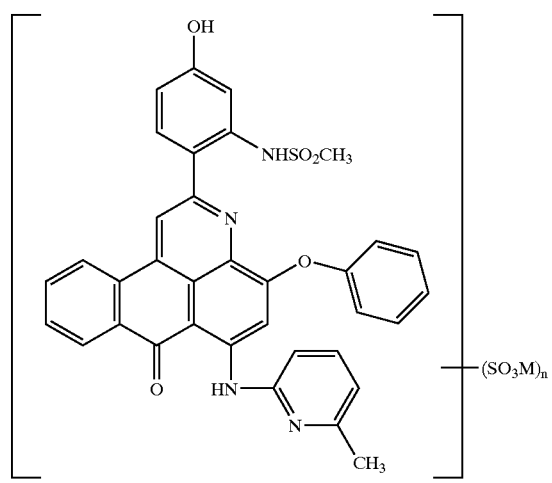
(B-36)
(B-39)
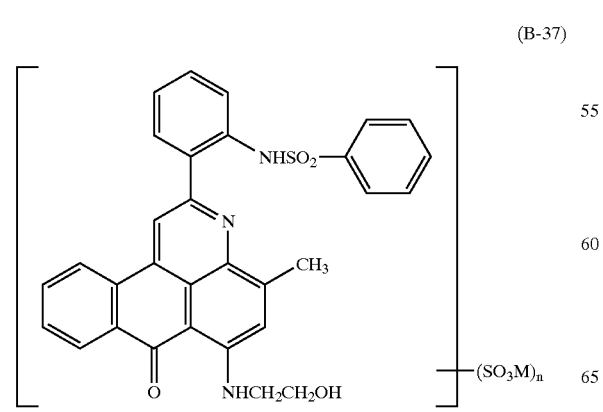
(B-37)
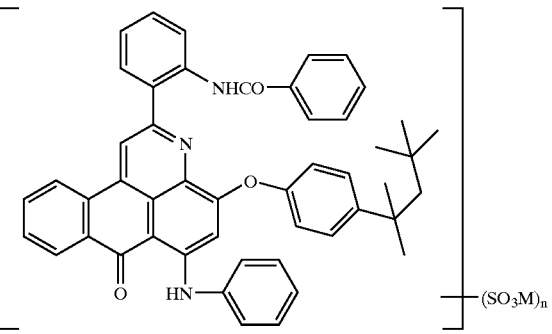
(B-40)

-continued
(B-41)
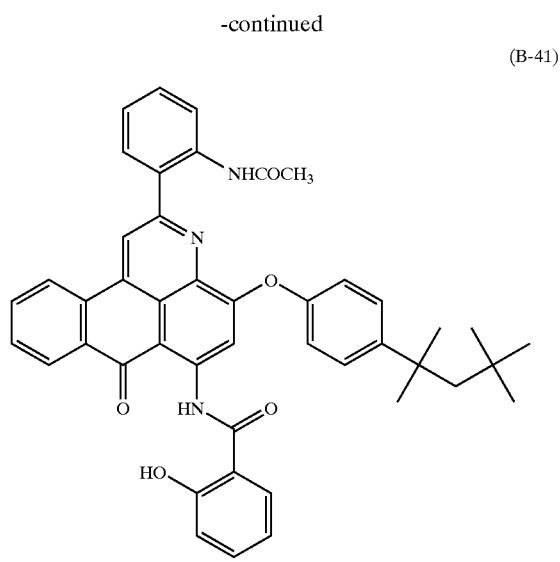
(B-42)
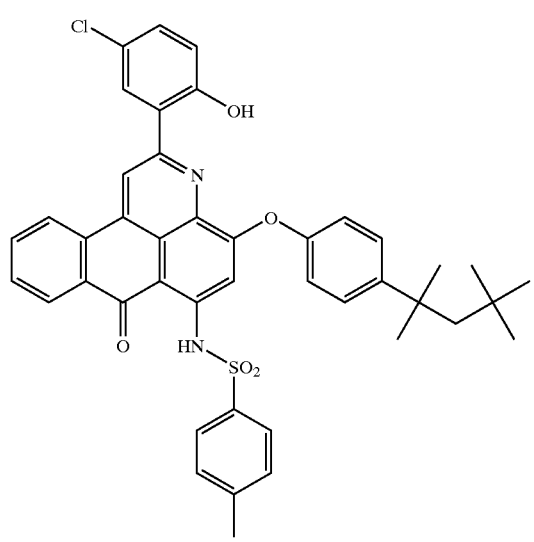
(B-43)
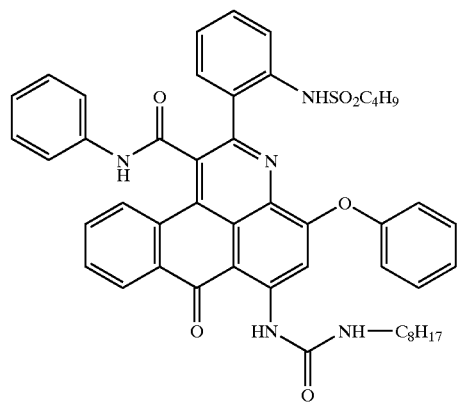
-continued
(B-44)
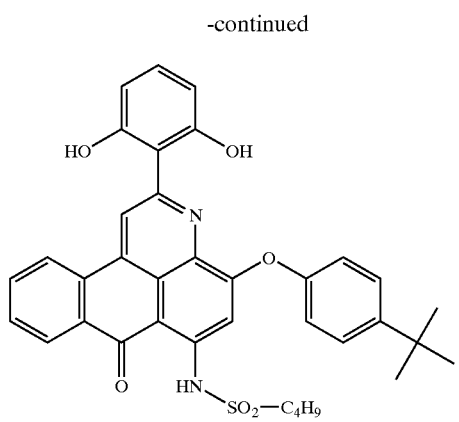
(B-45)
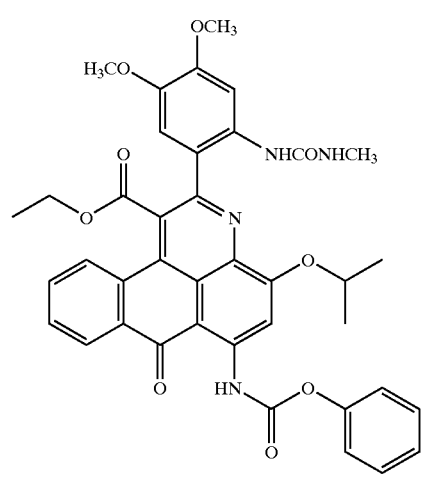
(B-46)
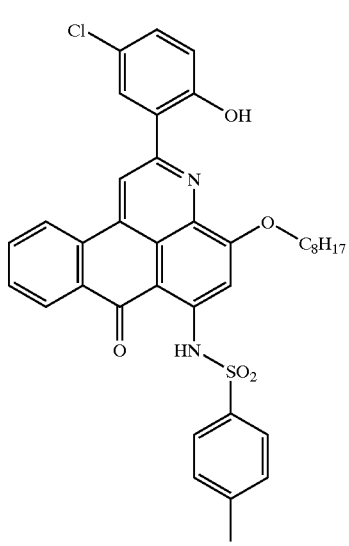

-continued
(B-47)
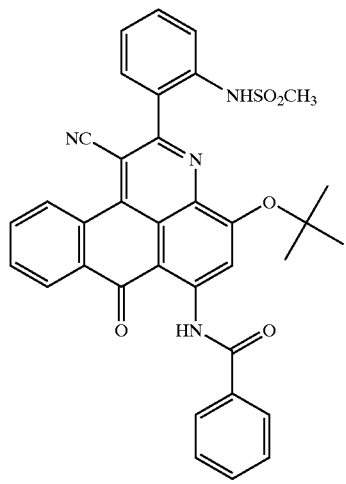
(B-50)
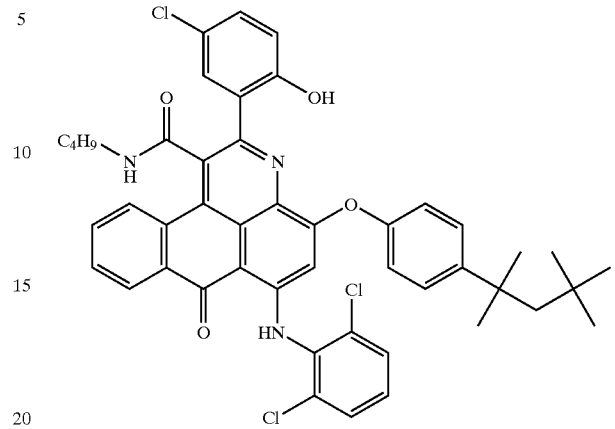
(B-48)
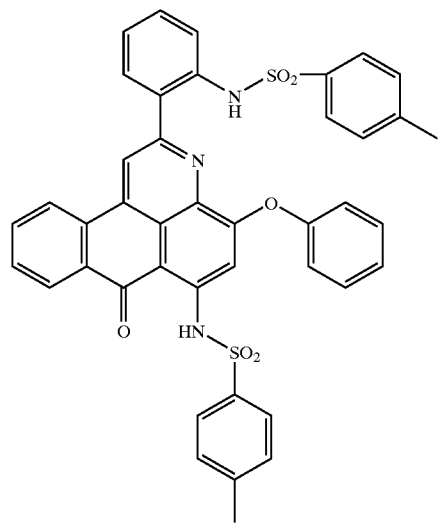
(B-51)
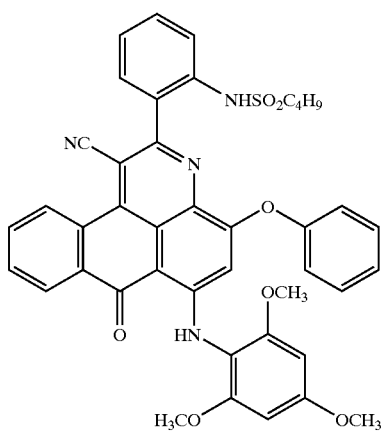
(B-49)
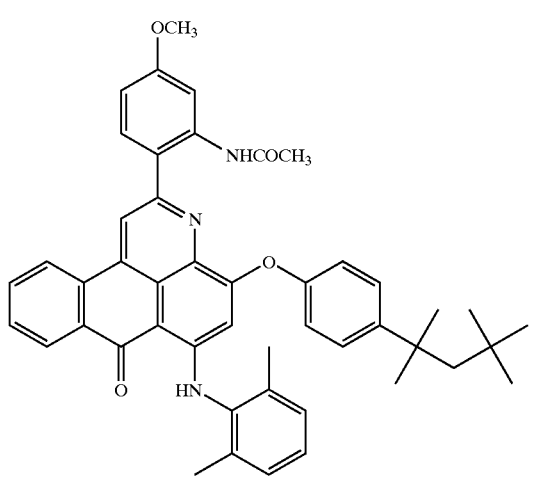
(B-52)
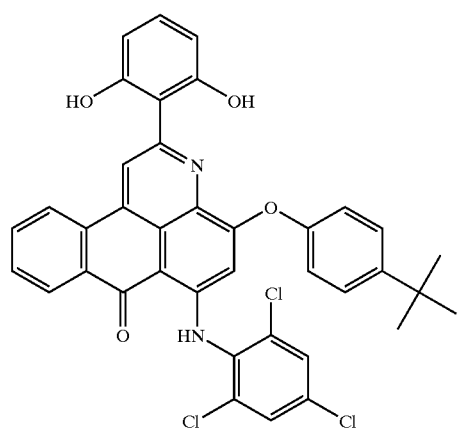

-continued
(B-53)
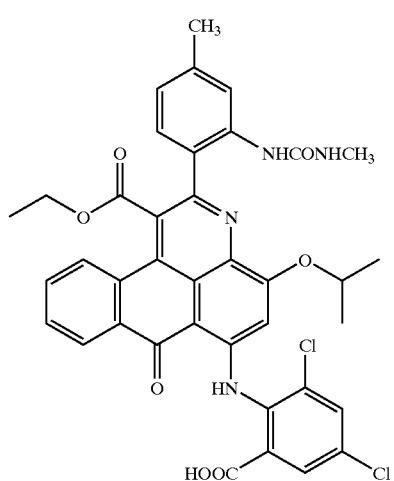
(B-56)
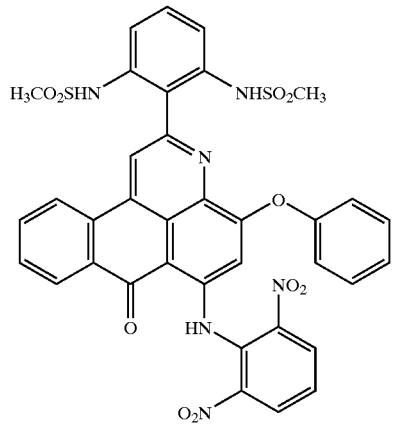
(B-54)
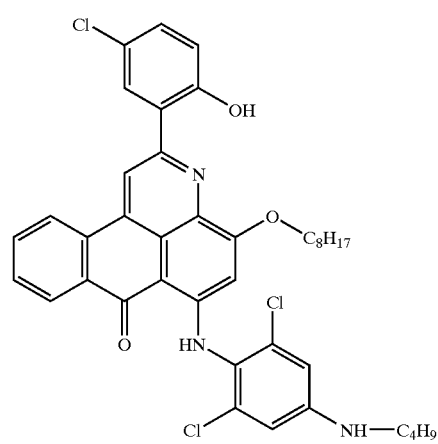
(B-57)
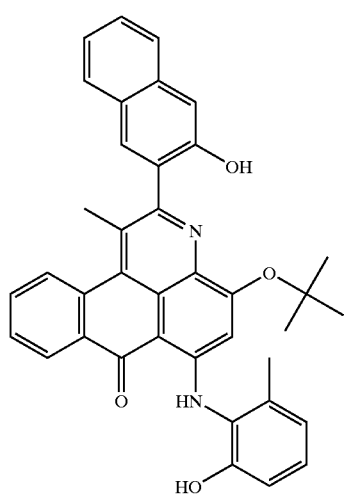
(B-55)
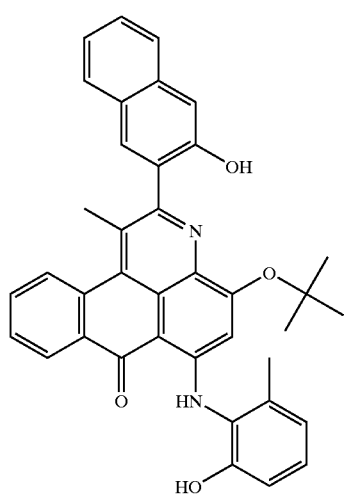
(B-58)
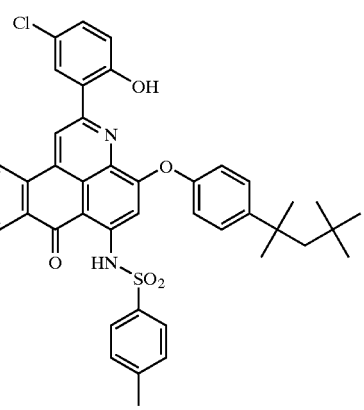

-continued
(B-59)
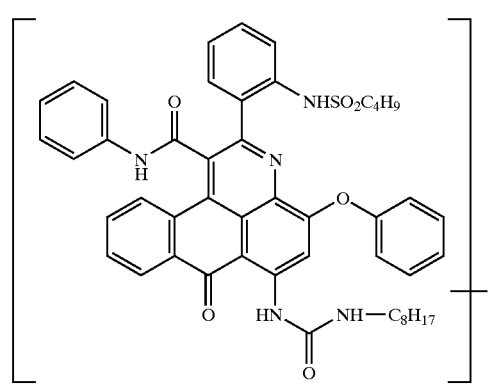
(B-62)
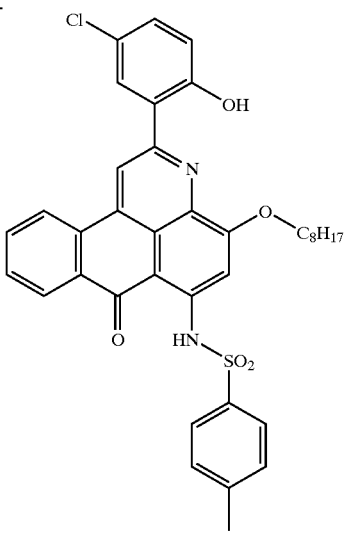
(B-60)
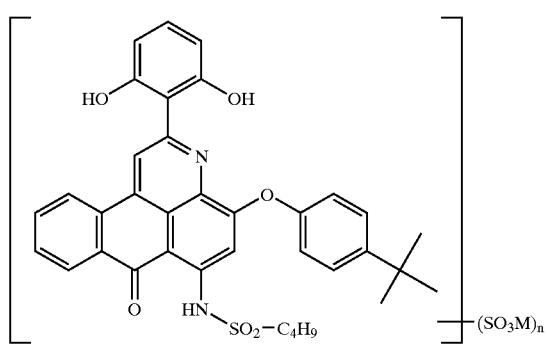
(B-63)
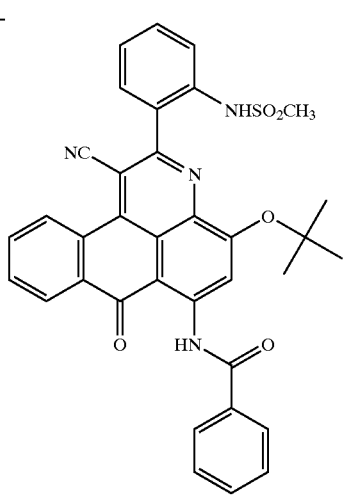
(B-61)
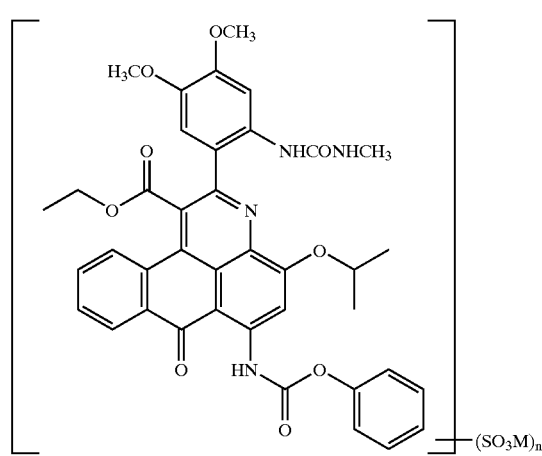
(B-64)
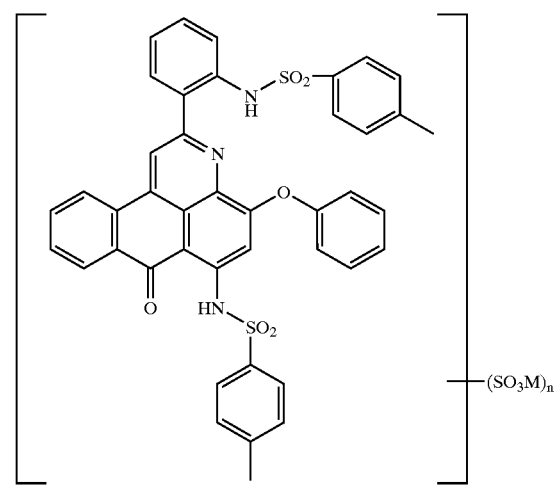

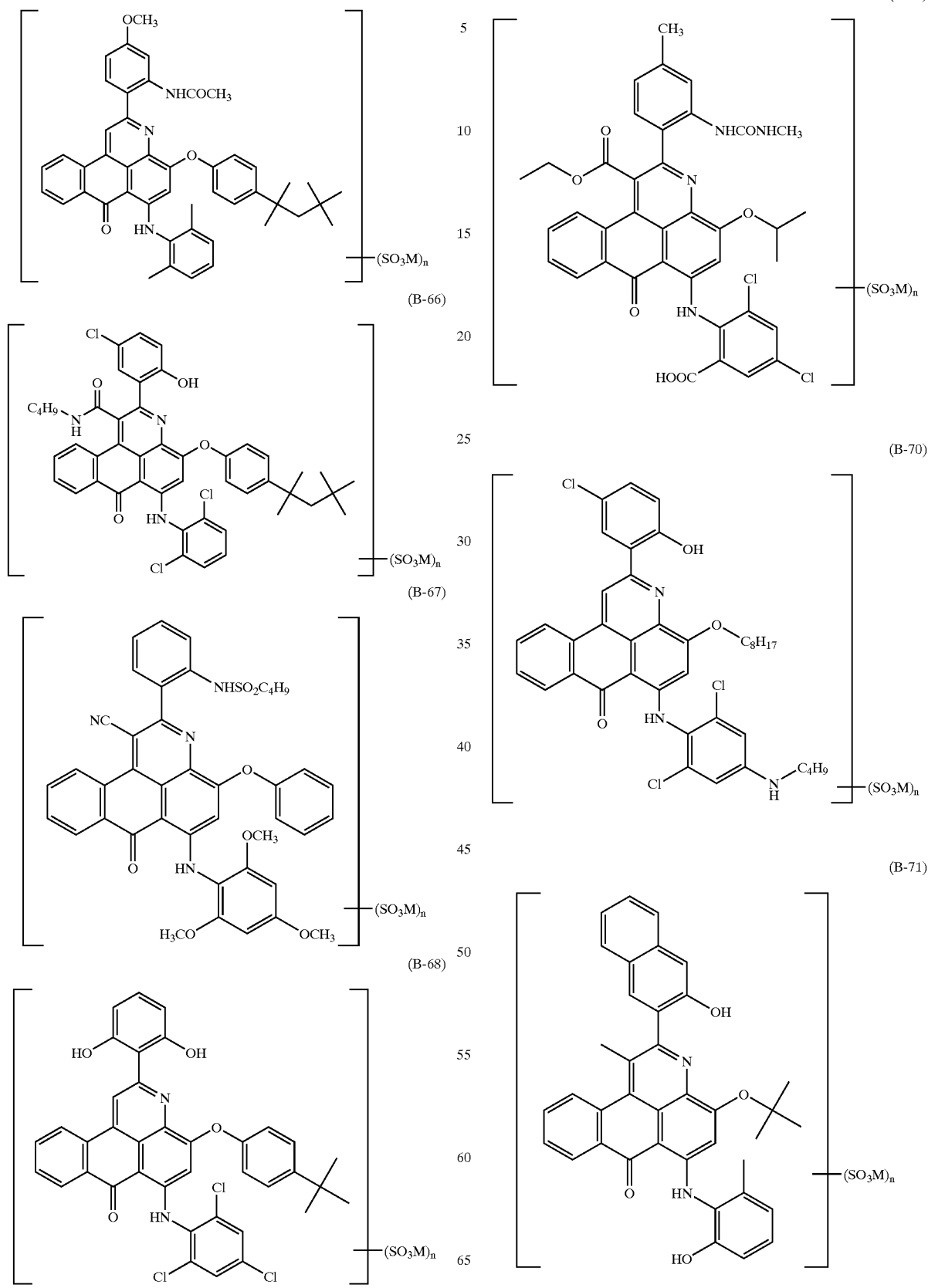

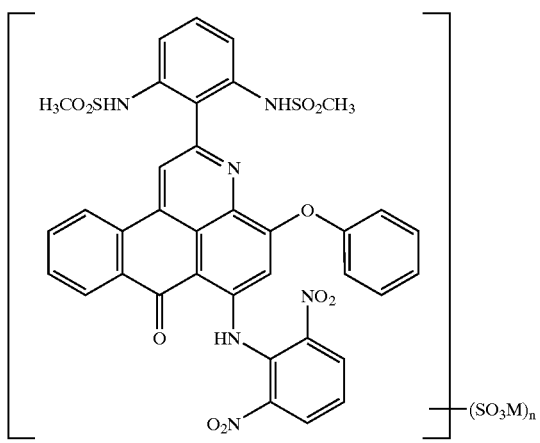
(B-72)
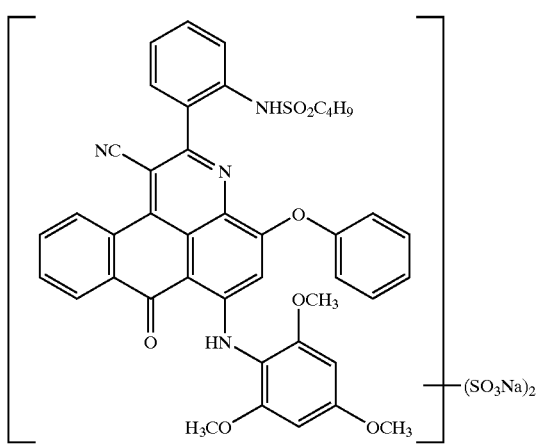
(B-73)
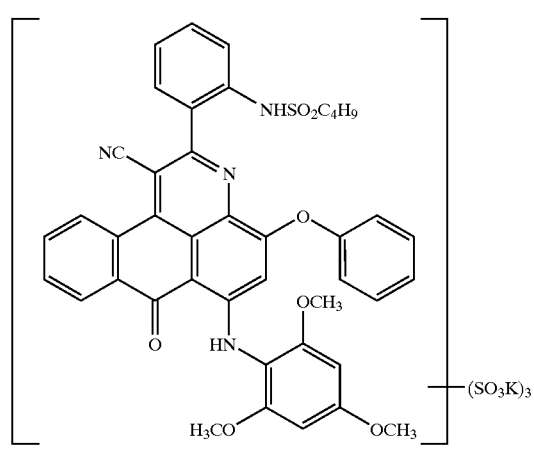
(B-74)
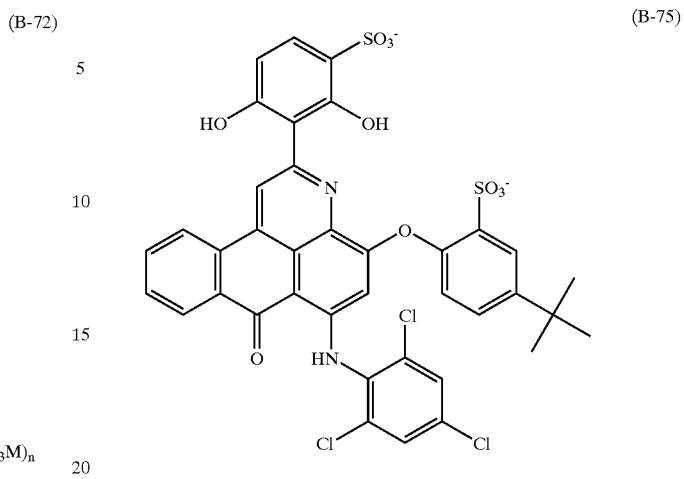
(B-75)
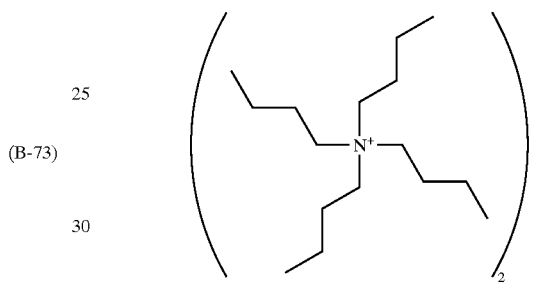
(C-1)
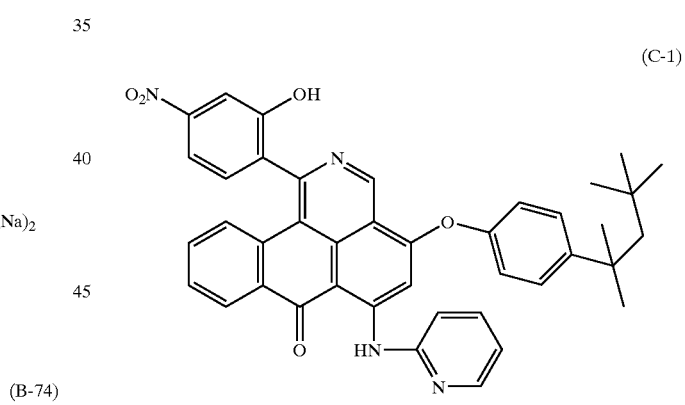
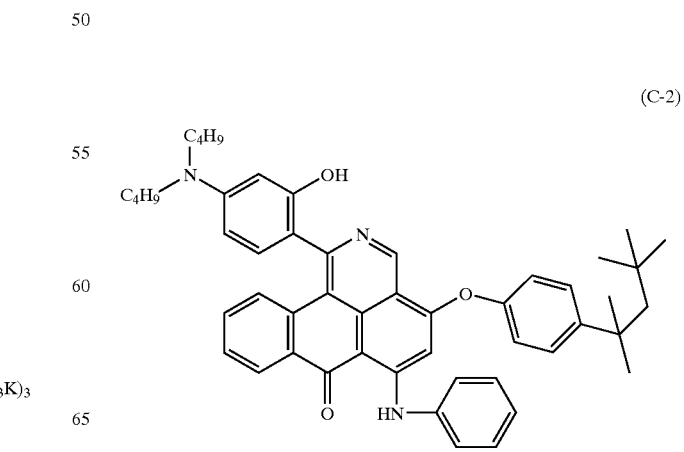
(C-2)

-continued

-continued

-continued
(D-5)
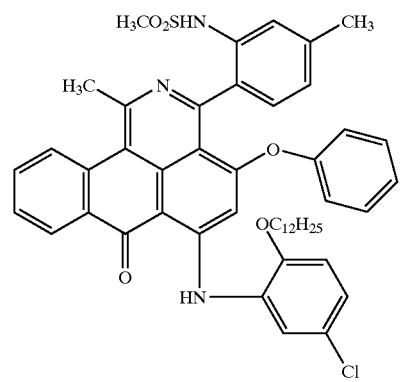
(D-6)
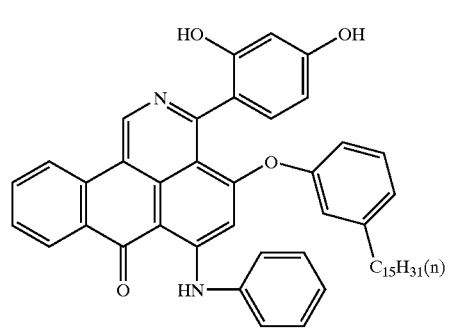
(D-7)
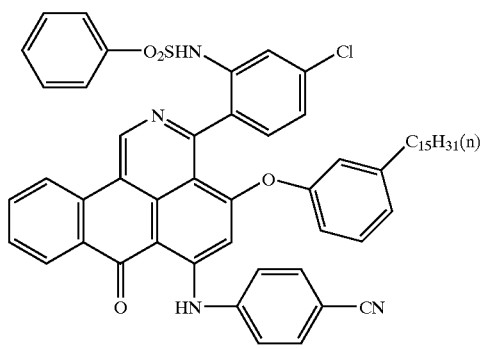
(D-8)
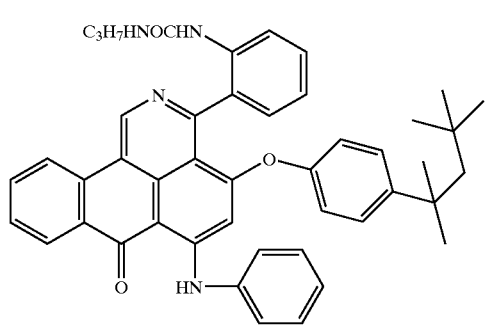
-continued
(D-9)
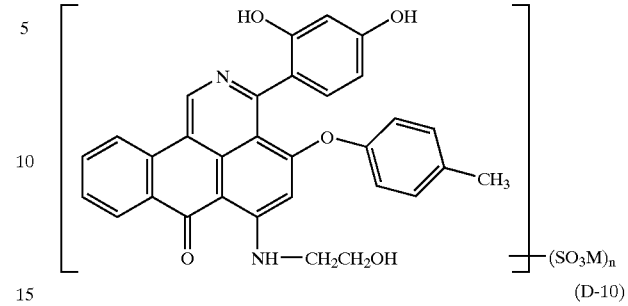
(D-10)
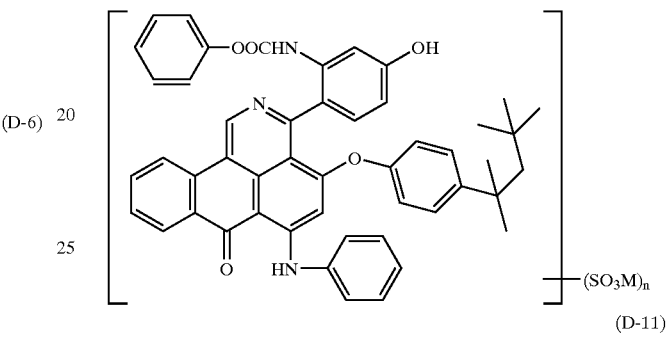
(D-11)
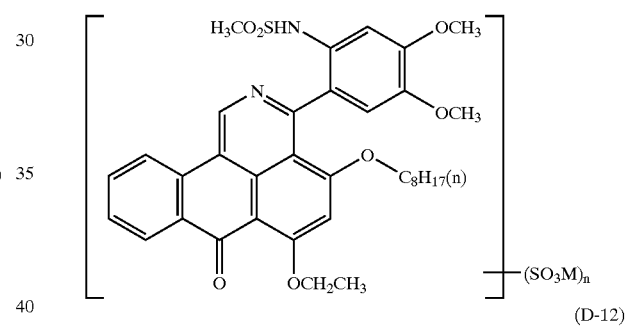
(D-12)
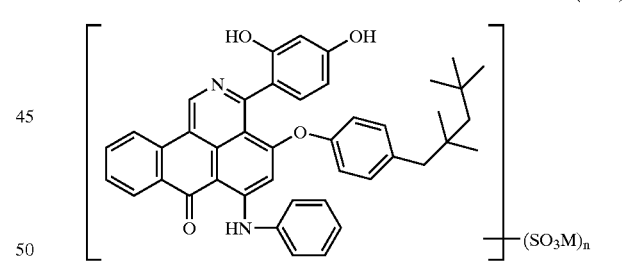
(D-13)
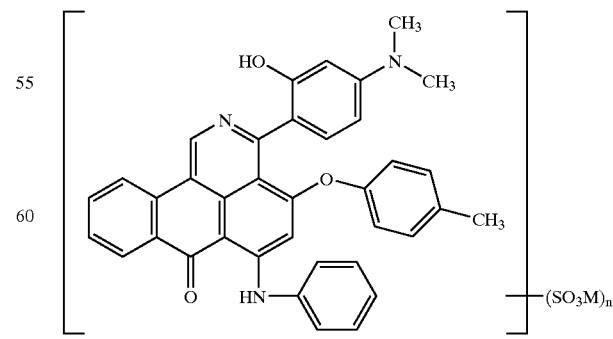

-continued
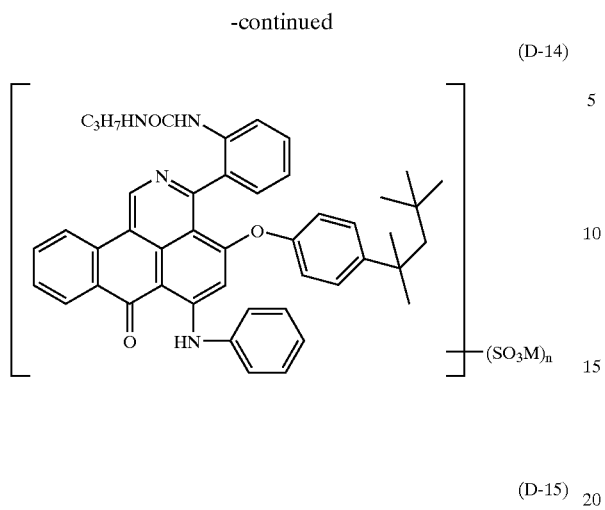
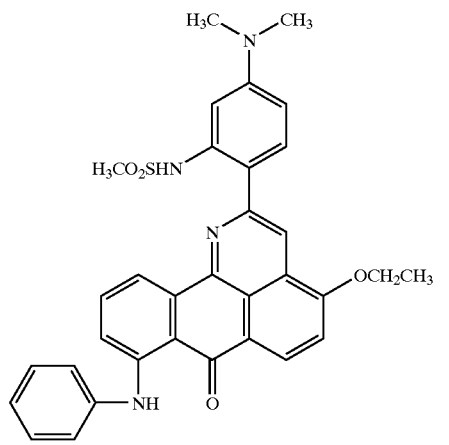
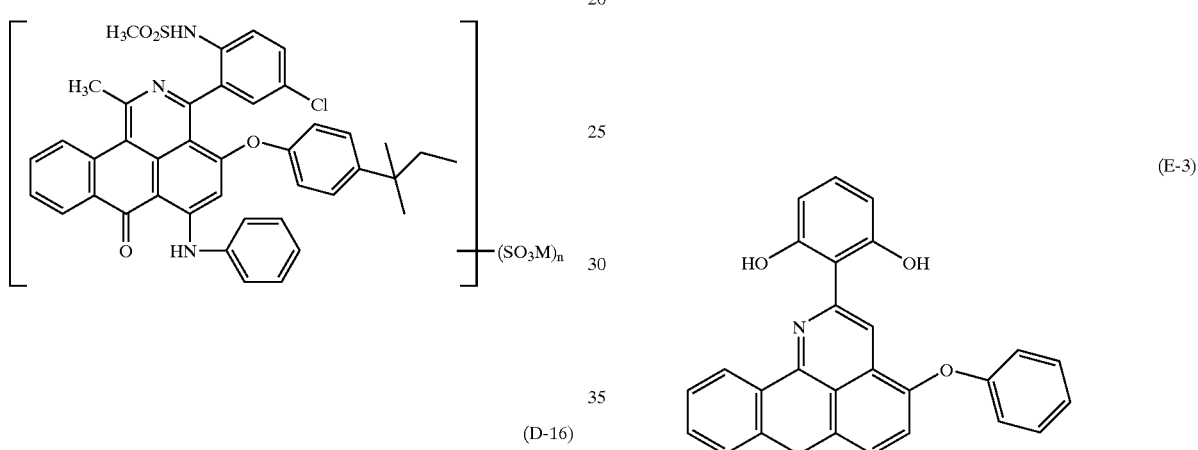
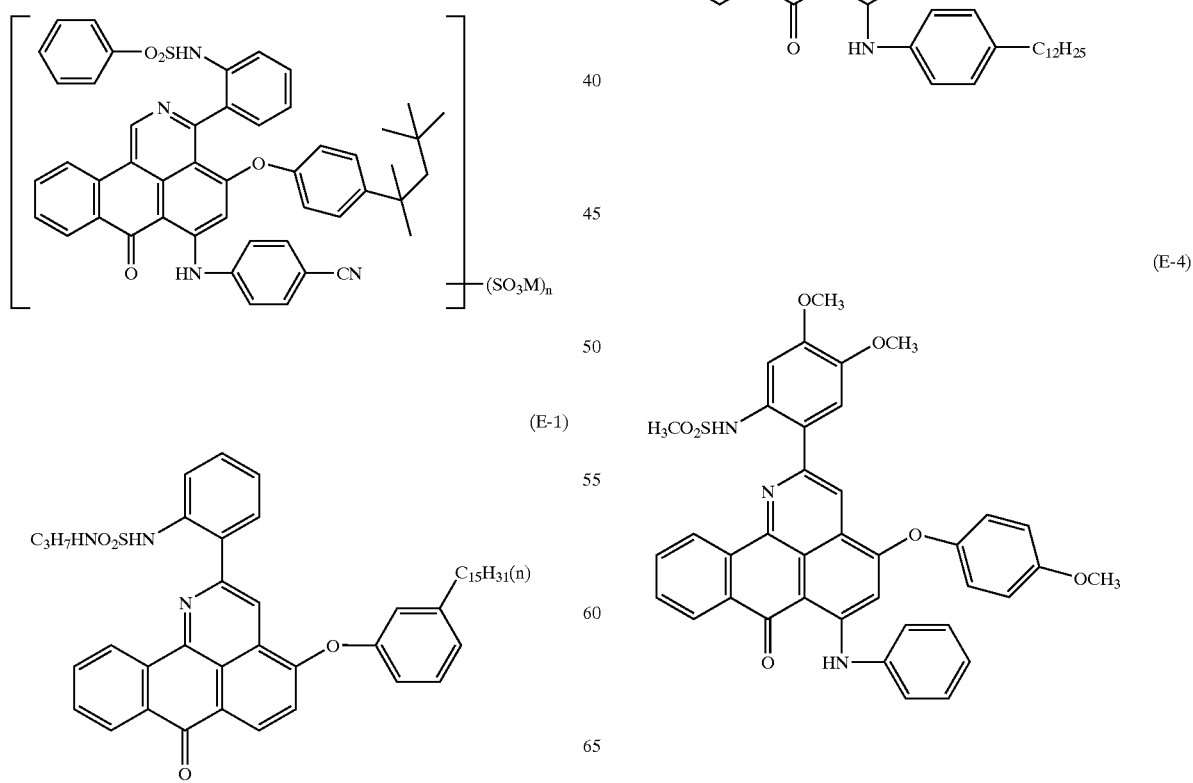

-continued
(E-5)
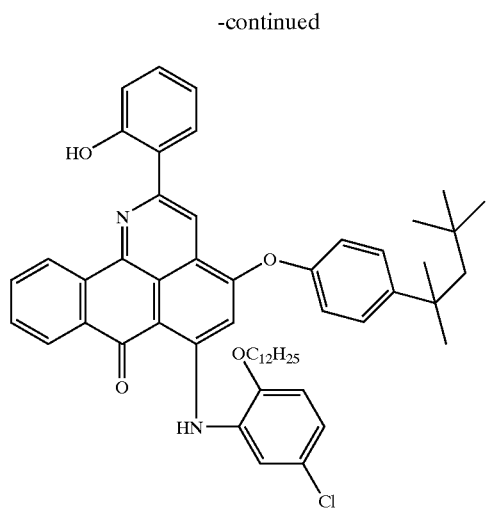
(E-6)
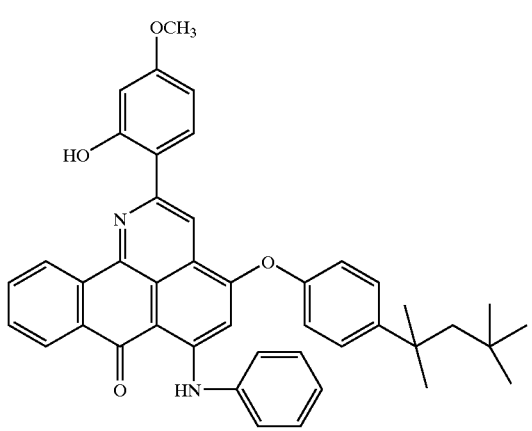
(E-7)
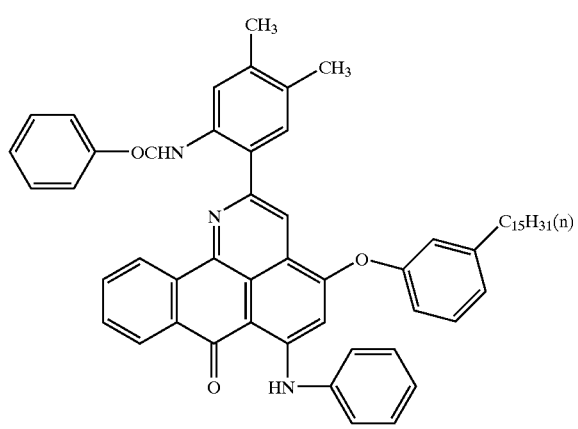
-continued
(E-8)
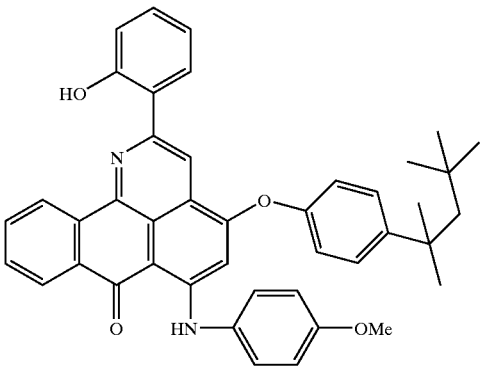
(E-9)
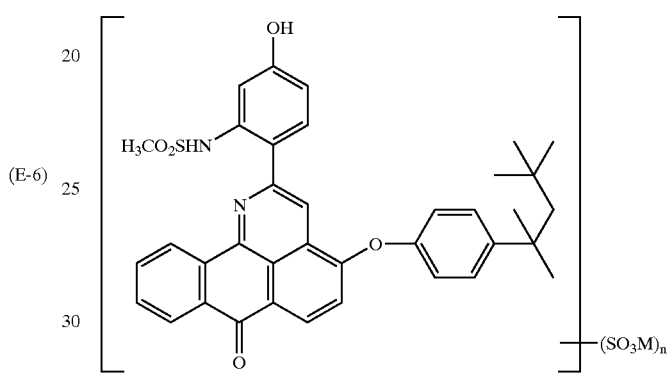
(E-10)
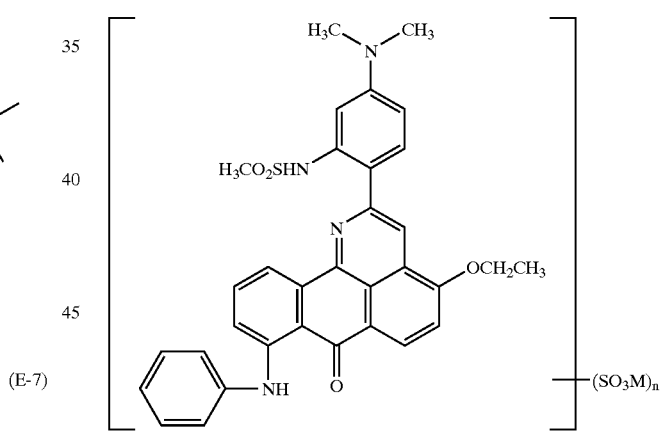
(E-11)
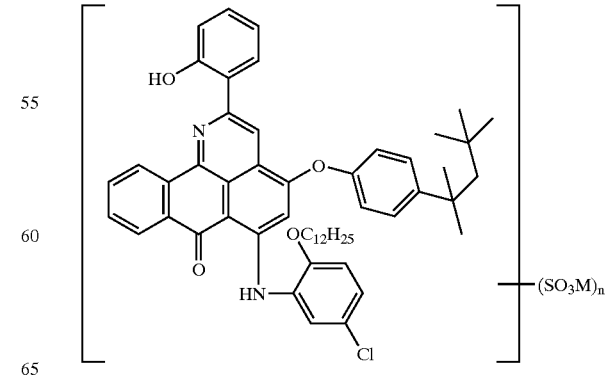

-continued
(E-12)
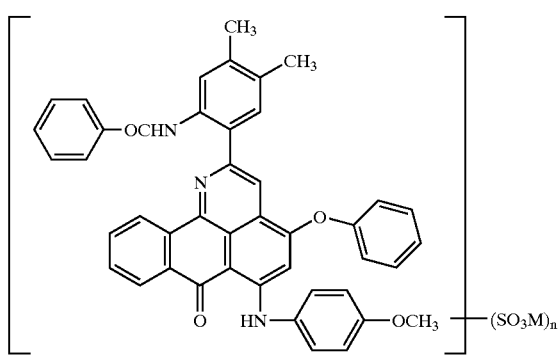
(E-13)
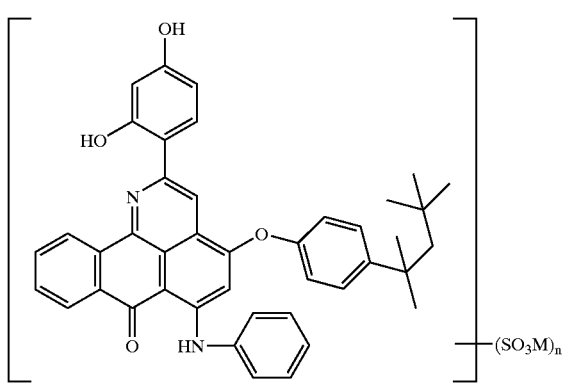
(E-14)
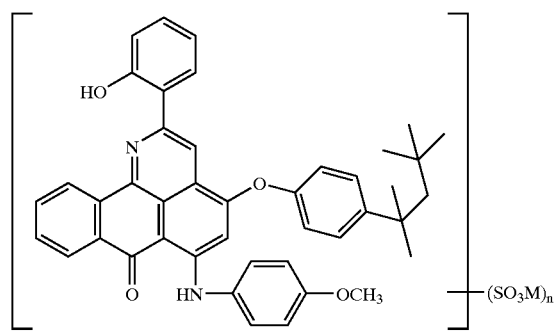
(E-15)
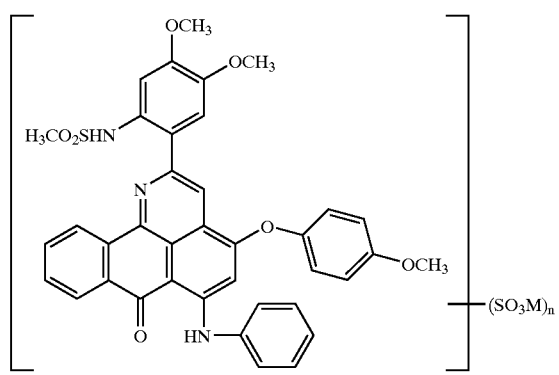
-continued
(E-16)
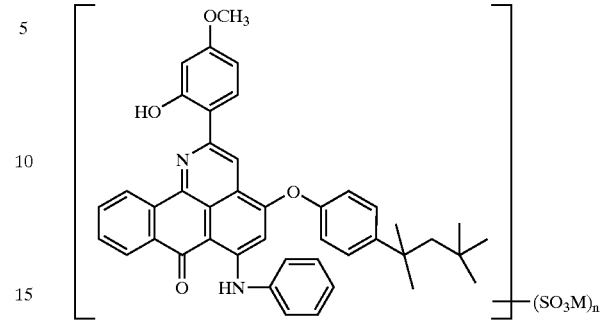
(F-1)
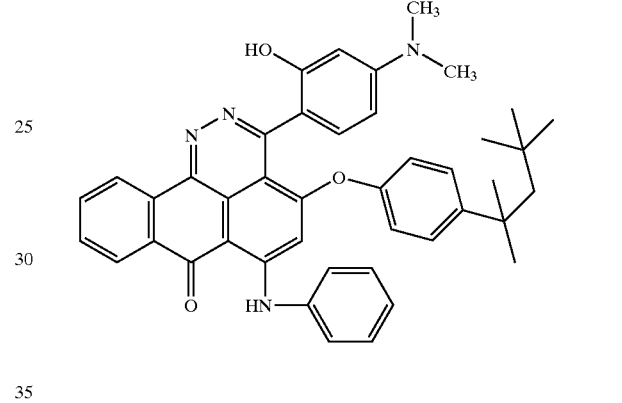
(F-2)
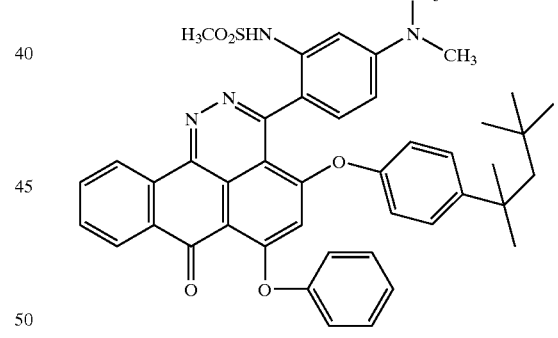
(F-3)
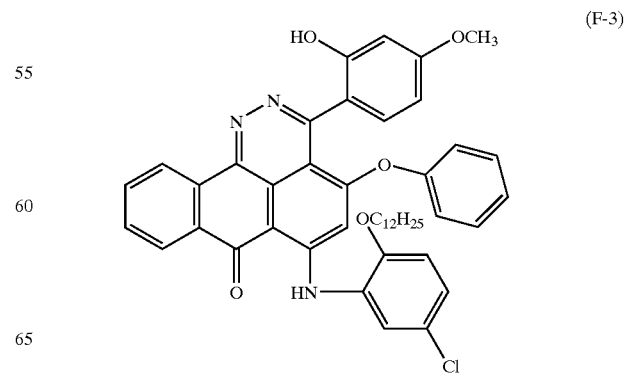

-continued
(F-4)
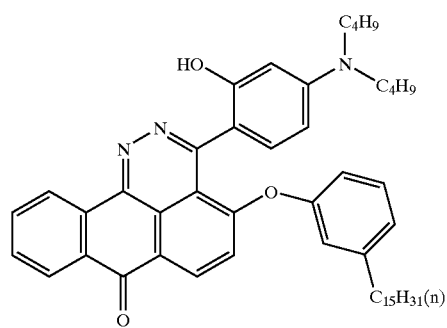
(F-8)
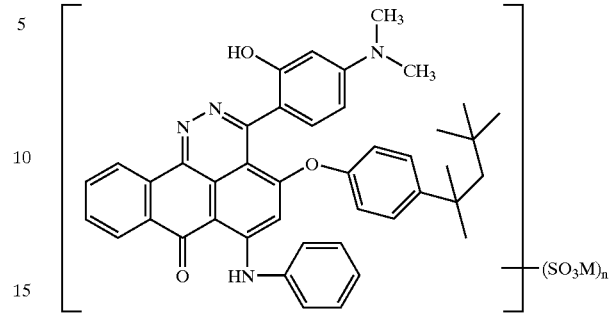
(F-5)
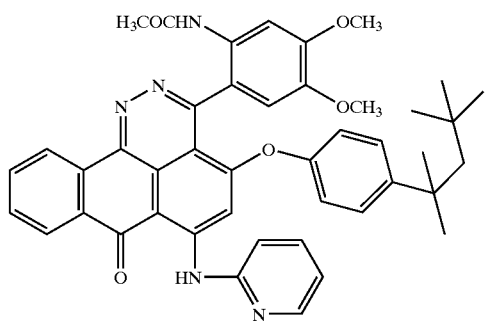
(F-9)
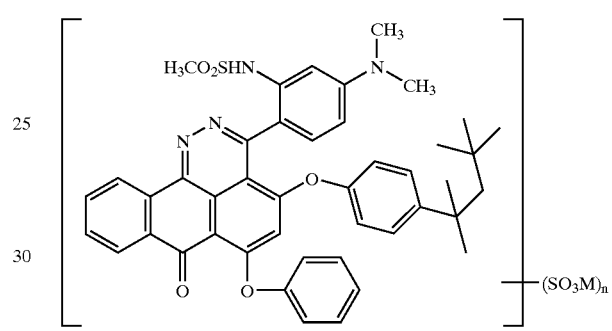
(F-6)
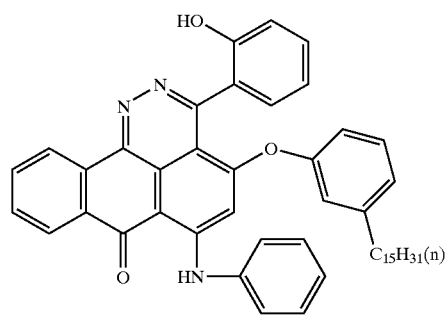
(F-10)
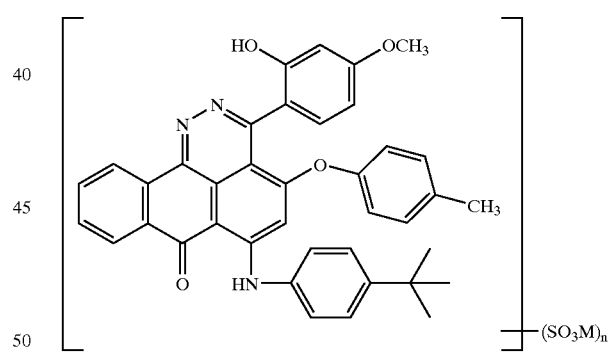
(F-7)
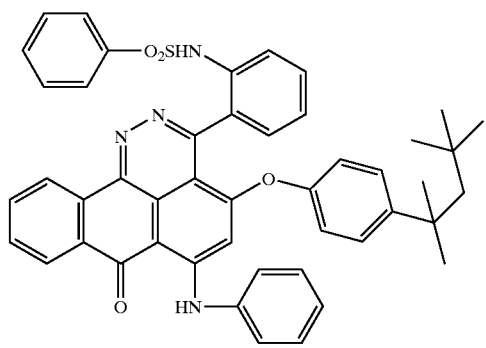
(F-11)
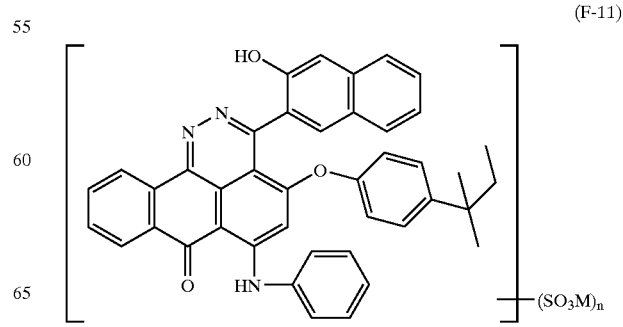

(F-12)
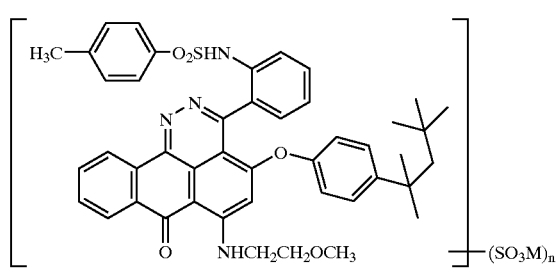
(G-1)
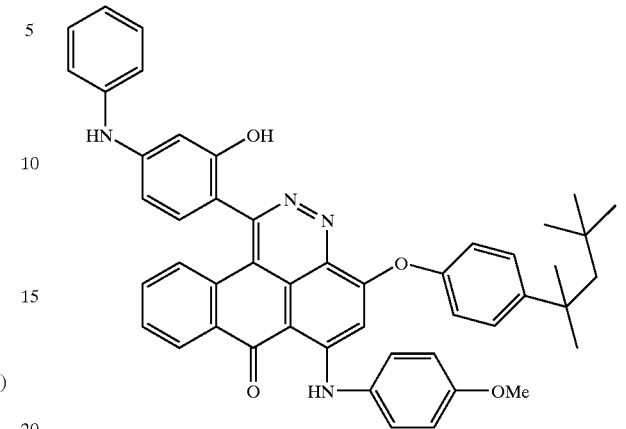
(F-13)
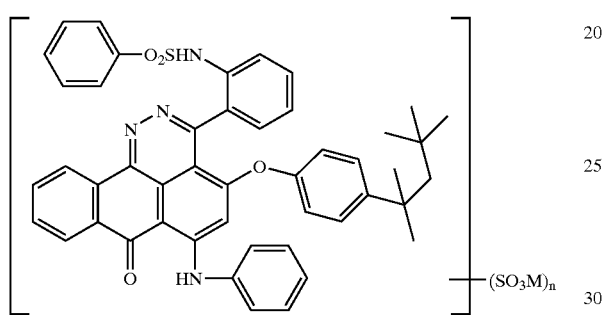
(G-2)
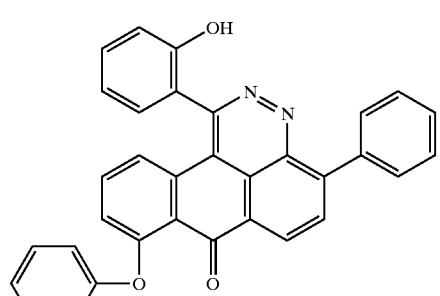
(F-14)
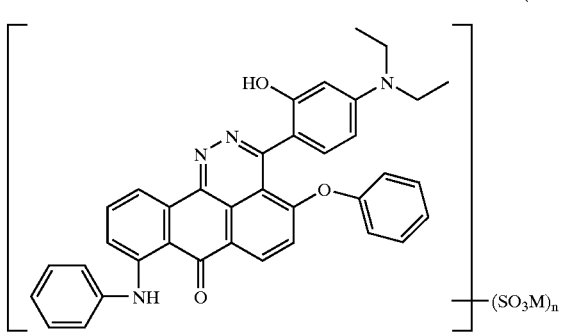
(G-3)
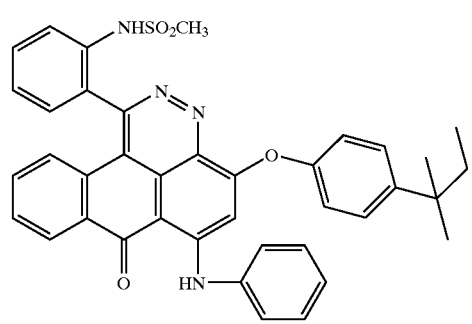
(F-15)
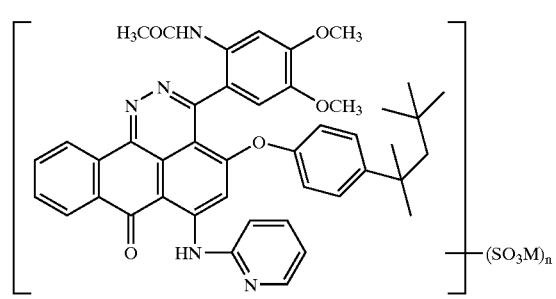
(G-4)
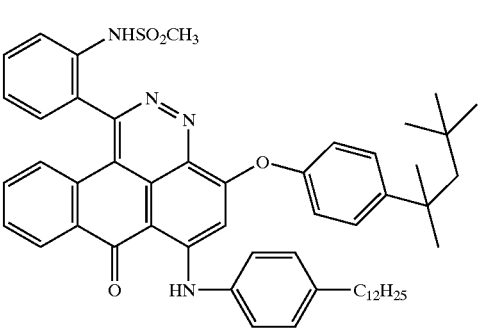

-continued
(G-5)
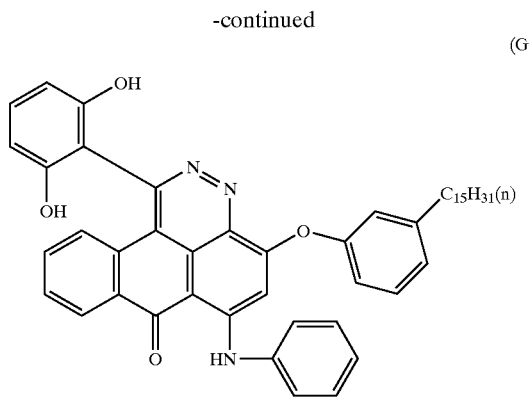
(G-6)
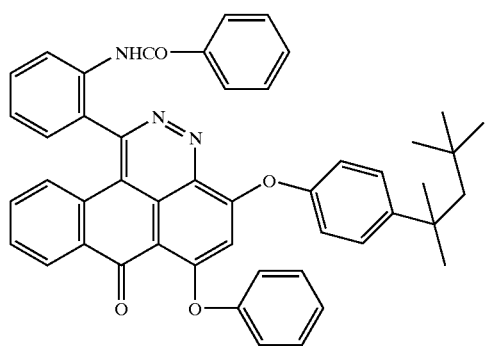
(G-7)
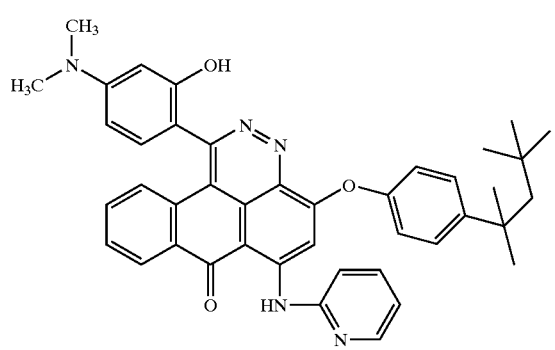
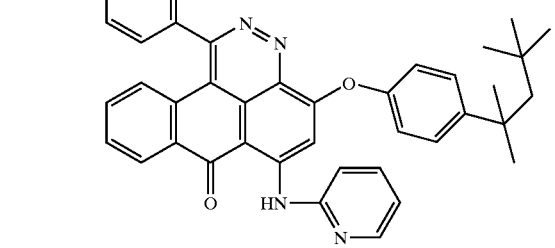
(G-8)
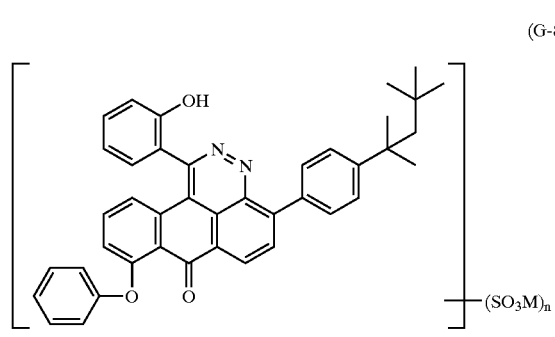
-continued
(G-9)
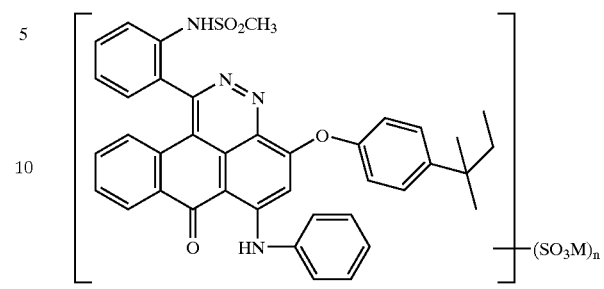
(G-10)
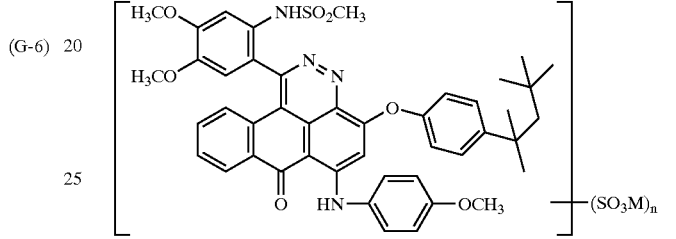
(G-11)
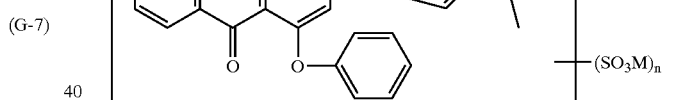
(G-12)
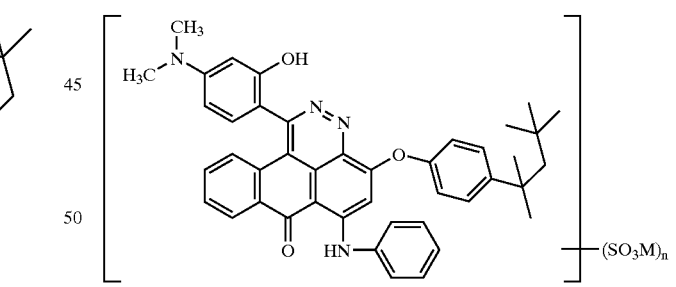
(G-13)
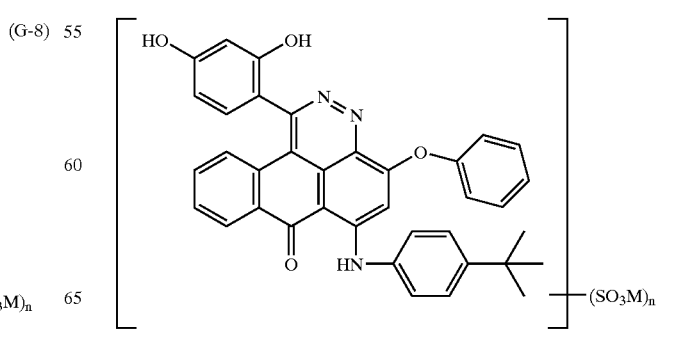

-continued

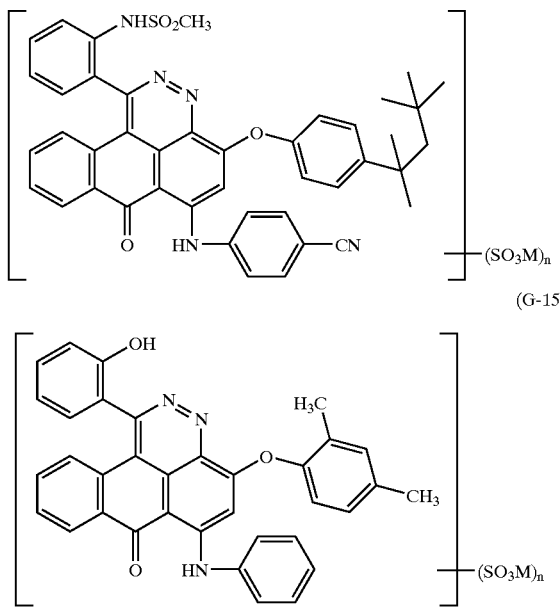

(G-14)

(G-15)

The ink jet printing ink relating to this invention contains at least one dye of the invention. Two or more dyes of the invention may be contained in combination. The ink may further contain other dyes.

A variety of solvents are usable in the ink jet printing ink of the invention, including aqueous solvents, oil solvents (or water-immiscible solvent) and solid (or phase change) solvents. Specifically, the use of aqueous solvents is preferred in this invention.

Aqueous solvents include water (preferably deionized water) and water-soluble organic solvents. Examples of water-soluble organic solvents include alcohols (e.g., methanol, ethanol, propanol, isopropanol, butanol, isobutanol, secondary butanol, tertiary butanol, benzyl alcohol), polyhydric alcohols (e.g., ethylene glycol, diethylene glycol, triethylene glycol, polyethylene glycol, propylene glycol, dipropylene glycol, polypropylene glycol, butylenes glycol, hexane-diol, pentane-diol, glycerin, hexane-triol, thioflycol), polyhydric alcohol ethers (e.g., ethylene glycol monomethyl ether, ethylene glycol monoethyl ether, ethylene glycol monobutyl ether, diethylene glycol monomethyl ether, diethylene glycol monoethyl ether, diethylene glycol monobutyl ether, propylene glycol monomethyl ether, propylene glycol monobutyl ether, ethylene glycol monomethyl ether acetate, triethylene glycol monomethyl ether, triethylene glycol monoethyl ether, ethylene glycol monophenyl ether, propylene glycol monophenyl ether), amines (e.g., ethanolamine, diethanolamine, triethanolamine, N-methyldiethanolamine, N-ethyldiethanolamine, morpholine, N-ethylmorpholine, ethylenediamine, diethylenediamine, triethylenetetramine, tetraethylenepentamine, polyethyleneimine, pentamethyldiethylenetriamine, tetramethylpropylenediamine), amides (e.g., formamide, N,N-dimethylformamide, N,N-dimethylacetoamide), heterocycles (e.g., 2-pyrrolidone, N-methyl-2-pyrrolidone, cyclohexylpyrrolidone, 2-oxazolidone, 1,3-dimethyl-2-imidazolidinone), sulfoxides (e.g., dimethylsulfoxide), sulfones (e.g., sulfolane) urea, acetonitrile, and acetone.

An aqueous solvent, in which the dye of the invention is soluble, is usable as it is. In this case, solubility of the dye in the aqueous solvent is important and the molecule of the dye of the invention preferably contains at least one sulfonic acid group or carboxyl group in its free acid form. Thus, at least one substituent included in the dye molecule preferably is a sulfonic acid group or carboxyl group, or a group having at least a sulfonic acid group or carboxyl group. It is more preferred that at least two sulfonic acid or carboxyl groups be contained in the dye molecule. Herein, the expression, at least two sulfonic acid or carboxyl groups means at least two sulfonic acid groups, at least two carboxyl groups, or at least one sulfonic group and at least one carboxyl group.

In cases where a dye of this invention is insoluble in an aqueous solvent, the dye is dispersed in the form of fine solid particles using a dispersing machine (e.g., ball mill, sand mill, atreiter, roll mill, agitator mill, Henshell mixer, colloid mill, ultrasonic homogenizer, pearl mill, jet mill, angmill, etc.) Alternatively, the dye can be dissolved in an organic solvent, followed by being dispersed in the aqueous solvent, together with a polymeric dispersing agent or surfactant. Further, a dye, which is in the form of insoluble liquid or semi-melt, is dispersed as it is, or is dissolved in an organic solvent, followed by being dispersed in an aqueous solvent together with a polymeric dispersing agent or surfactant. A dye of this invention, which is insoluble in an aqueous solvent, is preferably dispersed in the form of fine particles dispersed in the aqueous solvent. The dye is dispersed preferably to a level of an average fine particle size of 150 nm or less. The average particle size is a volume-average particle size, which can be determined in terms of a sphere of a mean circular equivalent diameter obtained from projection areas of transmission electron micrograph (TEM) of at least 100 particles. The volume-average particle size and its standard deviation are determined to calculate a coefficient of variation, which is the volume-average particle size, divided by the standard deviation. The volume-average particle size and its standard deviation can also be determined employing a dynamic light scattering method, for example, a laser particle size analysis system (available from Otsuka Denshi Co.) or Zeta-sizer (Malbahn Co.).

It is also preferred that the dye of this invention is dissolved in an organic solvent, followed by being dispersed together with an oil-soluble polymer in an aqueous solvent, in the form of fine particles dispersed in the aqueous solvent.

Specific examples of preparation of aqueous solvents used in ink jet printing inks are described in JP-A Nos. 5-148436, 5-295312, 7-97541, 7-82515 and 7-118584.

The oil-soluble polymer described above is not specifically limited and can optionally be selected according to an object, and preferred oil-soluble polymers include a vinyl polymer. Vinyl polymers usable in this invention include commonly known ones and any one of a water-insoluble type, water dispersion (self-emulsification) type and water-soluble type is usable in this invention. Of these, the water dispersion type is preferred in terms of easiness of preparing colored fine particles and dispersion stability.

A water dispersion type vinyl polymer may be any one of an ionic dissociation type, nonionic dispersing group containing type and a mixture of thereof. Examples of the ionic dissociation type vinyl polymer include a vinyl monomer containing a cationic dissociative group such as a tertiary amino group and a vinyl polymer containing an anionic dissociative group such as a sulfonic acid. Examples of the vinyl polymer containing a nonionic dispersing group include a vinyl polymer containing a nonionic dispersing group such as a polyethyleoxy-chain. Of these, an ionic dissociation type vinyl polymer containing an anionic dissociative group, a nonionic dispersing group containing type vinyl polymer and a mixture type vinyl polymer are preferable in terms of. dispersion stability of fine colored particles.

Monomers capable of forming the foregoing vinyl polymer include acrylic acid esters, methacrylic acid esters, vinyl esters, acrylamides, methacrylamides, olefins, styrenes and vinyl ethers. Specific examples of acrylic acid esters include methyl acrylate, ethyl acrylate, n-propyl acrylate, isopropyl acrylate, n-butyl acrylate, isobutyl acrylate, sec-butyl acrylate, tert-butyl acrylate, amyl acrylate, hexyl acrylate, 2-ethylhexyl acrylate, octyl acrylate, tert-octyl acrylate, 2-chloroethyl acrylate, 2-bromoethyl acrylate, 4-chlorobutyl acrylate, cyanoethyl acrylate, 2-acetoxyethyl acrylate, benzyl acrylate, methoxybenzyl acrylate, 2-chlorocyclohexyl acrylate, cyclohexyl acrylate, furfuryl acrylate, tetrahydrofurfuryl acrylate, phenyl acrylate, 5-hydroxypentyl acrylate, 2,2-dimethyl-3-hydroxypropyl acrylate, 2-methoxyethyl acrylate, 3-methoxybutyl acrylate, 2-ethoxyethyl acrylate, 2-butoxyethyl acrylate, 2-(2-methoxyethoxy)ethyl acrylate, 2-(2-butoxyethoxy)ethyl acrylate, glycidyl acrylate, 1-bromo-2-methoxyethyl acrylate, 1,1-dichloro-2-ethoxyethyl acrylate, 2,2,2-tetrafluoroethyl acrylate, and 1H,1H, 2H,2H-perfluorodecyl acrylate.

Specific examples of methacrylic acid esters include methyl methacrylate, ethyl methacrylate, n-propyl methacrylate, isopropyl methacrylate, n-butyl methacrylate, isobutyl methacrylate, sec-butyl methacrylate, tert-butyl methacrylate, amyl methacrylate, hexyl methacrylate, cyclohexyl methacrylate, benzyl methacrylate, chlorobenzyl methacrylate, octyl methacrylate, stearyl methacrylate, 2-(3-phenylpropyloxy)ethyl methacrylate, furfuryl methacrylate, tetrahydrofurfuryl methacrylate, phenyl methacrylate, cresyl methacrylate, naphthyl methacrylate, 2-hydroxyethyl methacrylate, 4-hydroxybutyl methacrylate, triethylene glycol monomethacrylate, dipropylene glycol monomethacrylate, 2-methoxyethyl methacrylate, 3-methoxybutyl methacrylate, 2-ethoxyethyl methacrylate, 2-iso-propoxyethyl methacrylate, 2-butoxyethyl methacrylate, 2-(2-methoxyethoxy) ethyl methacrylate, 2-(2-ethoxyethoxy)ethyl methacrylate, 2-acetoacetoxyethyl methacrylate, allyl methacrylate, glycidyl methacrylate, 2,2,2 -fluoroethyl methacrylate, and 1H,1H, 2H,2H-perfluorodecyl methacrylate.

Specific examples of vinyl esters include vinyl acetate, vinyl propionate, vinyl butyrate, vinyl isobutyrate, vinyl caproate, vinyl chloroacetate, vinyl methoxyacetate, vinyl phenylacetate, vinyl benzoate and vinyl salicylate.

Specific examples of acrylamides acrylamide, methacrylamide, ethylacrylamide, propylacrylamide, butylacrylamide, tert-butylacrylamide, tert-octylacrylamide, cyclohexylacrylamide, benzylacrylamide, hydroxymethylacrylamide, methoxymethylacrylamide, butoxymethylacrylamide, methoxyethylacrylamide, phenylacrylamide, dimethylacrylamide, diethylacrylamide, β-cyanoethylacrylamide, N-(2-acetoacetoxyethyl)acrylamide, and diacetoneacrylamide. Specific examples of methacrylamides include methacrylamide, methylmethacrylamide, ethylmethacrylamide, propyl-methacrylamide, butylmethacrylamide, tert-butyl-methacrylamide, cyclohexylmethacrylamide, benzyl-methacrylamide, hydroxymethylmethacrylamide, methoxyethyl-methacrylamide, phenylmethacrylamide, dimethyl-methacrylamide, β-cyanoethyl methacrylamide, and N-(2-acetoacetoxyethyl)-methacrylamide.

Specific examples of olefins include dicyclopentadiene, ethylene, propylene, 1-butene, 1-pentene, vinyl chloride, vinylidene chloride, isoprene, chloroprene, butadiene, and 2,3-dimethylbutadiene; specific examples of styrenes include styrene, methylstyrene, dimethylstyrene, trimethylstyrene, ethylstyrene, isopropylstyrene, chloromethylstyrene, methoxystyrene, acetoxystyrene, chlorostyrene, dichlorostyrene, bromostyrene and methyl vinylbenzoate.

Specific examples of vinyl ethers include methyl vinyl ether, butyl vinyl ether, hexyl vinyl ether, and methoxyethyl vinyl ether.

Other monomers include, for example, butyl crotonate, hexyl crotonate, dimethyl itaconate, dibutyl itaconate, diethyl maleate, dimethyl maleate, dibutyl maleate, diethyl fumarate, dimethyl fumarate, dibutyl fumarate, methyl vinyl ketone, phenyl vinyl ketone, methoxyethyl vinyl ketone, N-vinyloxazolidone, N-vinylpyrrolidone, vinylidene chloride, methylenemalonic nitrile, vinylidene, diphenyl-2-acryloyloxyethylphosphate, diphenyl-2-methacryloyloxyethylphosphate, dibutyl-2-acryloyloxyethylphosphate, and diocyl-2-methacryloyloxyethylphosphate.

Monomers containing a dissociative group include monomers containing an anionic dissociative group and monomers containing a cationic dissociative group. Examples of the monomers containing an anionic dissociative group include a carboxylic acid monomersulfonic acid monomer and phosphoric acid monomer. Specific examples of the carboxylic acid monomer include acrylic acid, methacrylic acid, itaconic acid, maleic acid, fumaric acid, citraconic acid, crotonic acid, itaconic acid monoalkyl esters (e.g., monomethyl itaconate, monoethyl itaconate, monobutyl itaconate), and maleic acid monolkyl esyers (e.g., monomethyl maleate, monoethyl maleate, monobutyl maleate).

Specific examples of the sulfonic acid monomer include styrenesulfonic acid, vinylsulfonic acid, acryloyloxyalkylsulfonic acids (e.g., acryloyloxymethylsulfonic acid, acryloyloxyethylsulfonic acid, acryloyloxypropylsulfonic acid), methacryloyloxyalkylsulfonic acids (e.g., methacryloyloxymethylsulfonic acid, methacryloyloxyethylsulfonic acid, methaacryloyloxypropylsulfonic acid), acrylamidoalkylsulfonic acids (e.g., 2-acrylamido-2-methylethanesulfonic acid, 2-acrylamido-2-methylpropanesulfonic acid, 2-acrylmido-2-methylbutanesulfonic acid), and methacrylamidoalkylsulfonic acids (e.g., 2-methacrylamido-2-methylethanesulfonic acid, 2-methacrylamido-2-methylpropanesulfonic acid, 2-methacrylmido-2-methylbutanesulfonic acid). Specific examples of the phosphoric acid monomer include vinylphosphonic acid and methacryloyloxyethylphosphonic acid. Of the foregoing, acrylic acid, methacrylic acid, styrenesulfonic acid, vinylsulfonic acid, acrylamidoalkylsulfonic acid, and methacrylamidoalkylsulfonic acid are preferred; and acrylic acid, methacrylic acid, styrenesulfonic acid, 2-acrylamido-2-methylpropanesulfonic acid, and 2-acrylamido-2-methylbutanesulfonic acid are more preferred.

Specific examples of the monomer containing a cationic dissociative group include tertiary amino group containing monomers such as dialkylaminoethyl methacrylate and dialkylaminoethyl acrylate.

Monomers containing a nonionic dispersing group include, for example, an ester of a polyethylene glycol monoalkyl ether and a carboxylic acid monomer, an ester of a polyethylene glycol monoalkyl ether and a sulfonic acid monomer, an ester of a polyethylene glycol monoalkyl ether and a phosphoric acid monomer, a vinyl group containing urethane formed of a polyethylene glycol monoalkyl ether and a isocyanate group containing monomer, and a macromonomer containing a polyvinyl alcohol structure. The repeating number of an ethyleneoxy portion of a polyethylene glycol monoalkyl ether is preferably 8 to 50, and more preferably 10 to 30. The carbon number of a polyethylene glycol monoalkyl ether is preferably 1 to 20, and more preferably 1 to 12. These monomers may be used singly or in combination to form a vinyl polymer and can be optimally selected depending on the objective vinyl polymer (e.g., control of Tg, improvement in solubility, and dispersion stability).

Organic solvents are employed as an oil solvent used in this invention. Examples of the oil solvent include alcohols (e.g., pentanol, heptanol, octanol, phenylethyl alcohol, phenylpropyl alcohol, furfuryl alcohol, anise alcohol), esters (e.g., ethylene glycol diacetate, ethylene glycol monomethyl ether acetate, diethylene glycol monomethyl ether acetate, propylene glycol diacetate, ethyl acetate, amyl acetate, benzyl acetate, phenylethyl acetate, phenoxyethyl acetate, ethyl phenylacetate, benzyl propionate, ethyl benzoate, butyl laurate, isopropyl myristate, trimethyl phosphate, tributyl phosphate, diethyl phthalate, dibutyl phthalate, diethyl maloate, dipropyl maloate, diethyl diethylmaloate, diethyl succinate, dibutyl adipate, di-2-methoxyethyl adipate, diethyl sebacate, diethyl maleate, dibutyl maleate, diocyl maleate, diethyl fumarate, diocyl fumarate, 3-hexenyl cinnamate), ethers (e.g., butyl phenyl ether, benzyl ethyl ether, hexyl ether), ketones (benzyl ethyl ketone, benzylacetone, diacetone alcohol, cyclohexanone), hydrocarbons (e.g., petroleum ether, petroleum benzyl, tetralin, decalin, tert-amylbenzene, dimethylnaphthalene), and amides (e.g., N,N-diethyldodecaneamide).

The foregoing oil solvents can be used to dissolve the dye relating to this invention as it is. The solvents can also be used in combination with polymeric dispersing agents or binders to disperse or dissolve the dye. Specific examples of preparation of oil solvents used in ink jet printing inks are described in JP-A Nos. 3-231975 and 5-508883.

Solid (or phase change) solvents used in this invention are phase-chageable solvents, which are solid at room temperature and melt liquid at the heating ejection of ink jet ink. Examples of phase change solvents include natural wax (e.g., beeswax, carnauba wax, rice wax, Japan wax, jojoba oil, spermacetic, candelilla wax, lanolin, montan wax, ozocerite, ceresine, paraffin wax, microcrystalline wax, petrolatum), polyethylene wax derivatives, chlorinated hydrocarbons, organic acids (e.g., palmitic acid, stearic acid, behenic acid, tiglic acid, 2-acetonaphthone-behenic acid, 12-hydroxystearic acid, dihydroxystearic acid), organic acid esters (e.g., esters of organic acids described above and alcohols such as glycerin, diethylene glycol, and ethylene glycol), alcohols (e.g., dodecanol, tetradecanol, hexadecanol, eicosanol, docosanol, tetracosanol, hexacosanol, octacosanol, dodecenol, myricyl alcohol, tetracenol, hexadecenol, eicocenol, dococenol, pinene glycol, hinokiol, butynediol, nonanediol, isophthalyl alcohol, mesicerin, tereaphthalyl alcohol, hexanediol, decanediol, dodecanediol, tetradecanediol, hexadecanediol, docosanediol, tetracosanediol, terebineol, phenylglycerin, eicosanediol, octanediol, phenylpropylene glycol, bisphenol A, paraarfacmylphenol), ketones (e.g., benzoylacetone, diacetobenzene, benzophenone, tricosanone, heptacosanone, heptatriacontanone, hentriacontanone, heptatriacontanone, stearone, laurone, dianisole), amides (e.g., oleic acid amide, lauric acid amide, stearic acid amide, ricinolic acid amide, palmitic acid amide, tetrahydrofuranic acid amide, erucic acid amide, myristic acid amide, 12-hydroxystearic acid amide, N-stearylerucic acid amide, N-oleylatearic acid amide, N,N'-ethylene-bis-oleic acid amide, N,N'-methylene-bis-stearic amide, N,N'-ethylene-bis-behenic acid amide, N,N'-xylylene-bis-stearic acid amide, N,N'-butylene-bis-stearic acid amide, N,N'-dioleyladipic acid amide, N,N'-distearyladipic acid amide, N,N'-dioleylsebacic acid amide, N,N'-distearylsebacic acid amide, N,N'-distearylterephthalic acid amide, N,N7-distearylisophthalic acid amide, phenacetin, toluamide, acetoamide, oleic acid reaction product, tetraamide of a dimmer acid, a diamine and a fatty acid, such as oleic acid dimmer/ethylenediamine/stearic acid (molar ratio, 1:2:2)), sulfonamides (e.g., p-toluenesulfonamide, ethylbenzenesulfonamide, butylbenzenesulfonamide), silicones (e.g., Silicone SH6018, available from Toray Silicone, Silicone KR215, 216, 220,available Shinetu Silkicone Co., Ltd.), chromans (e.g., Eschron G-90, available from Shi-Nittestu Kagaku Co., Ltd.), cholesterol fatty acid esters (e.g., stearic acid cholesterol, palmitic acid cholesterol, myristic acid cholesterol, behenic acid cholesterol, lauric acid cholesterol, melissic acid cholesterol), and saccharide fatty acid esters (e.g., stearic acid saccharide, palmitic acid saccharide, behenic acid saccharide, lauric acid saccharide, melissic acid saccharide, stearic acid lactose, palmitic acid lactose, myristic acid lactose, behenic acid lactose, melissic acid lactose). The phase-changing temperature of from solid to liquid of a solid (or phase change) solvent is preferably 60 to 200° C., and more preferably 80 to 150° C. The dye of this invention can be dissolved in heated melt of the solid (or phase change) solvent. The solid (or phase change) solvent can also be used in combination with polymeric dispersing agents or binders to disperse or dissolve the dye. Specific examples of preparation of solid solvents used in ink jet printing inks are described in JP-A Nos. 5-186723 and 7-70490.

An ink jet ink according to this invention in which the dye of this invention is dissolved or dispersed using aqueous solvents, oil solvent or solid solvents, exhibits preferably a viscosity at ejection of not more than 40 cps, and more preferably not more than 30 cps. The ink exhibits preferably a surface tension at ejection of $2 \times 10^{-4}$ to $1 \times 10^{-3}$ N/cm, and more preferably $3 \times 10^{-4}$ to $8 \times 10^{-4}$ N/cm.

The dye of this invention is contained in the ink preferably at 0.1 to 25% by weight, and more preferably 0.5 to 10% by weight, based on the ink.

A polymeric dispersing agent used in this invention is preferably a polymeric compound having a molecular weight of 1,000 to 1,000,000, which is contained in the ink, preferably at 0.1 to 50% by weight, based on the ink.

The ink jet ink of this invention may further be added with additives such as a viscosity adjusting agent, surface tension adjusting agent, resistivity adjusting agent, film forming agent, dispersing agent, surfactant, UV absorber, antioxidant, anti-discoloring agent, anti-fungal agent, and rust inhibitor to enhance discharge stability, suitability for a printing head or ink cartridge, image lasting quality and other performances.

The ink jet ink of this invention is not specifically limited with respect to the used ink jet printing system and is preferable for use in on-demand type ink jet printers. Examples of on-demand type systems include an electromechanical conversion system (e.g., single cavity type, double cavity type, vendor type, piston type, share-mode type, shared wall type), electrothermal conversion system (e.g., thermal ink jet type, bubble jet (R) type), electrostatic attraction system (e.g., field-control type, slit jet type), discharge system (e.g., spark jet type).

EXAMPLES

The present invention is further described based on examples but embodiments of the invention are by no means limited to these.

Example 1

Synthesis of Compound (i) Synthesis of Compound A-26

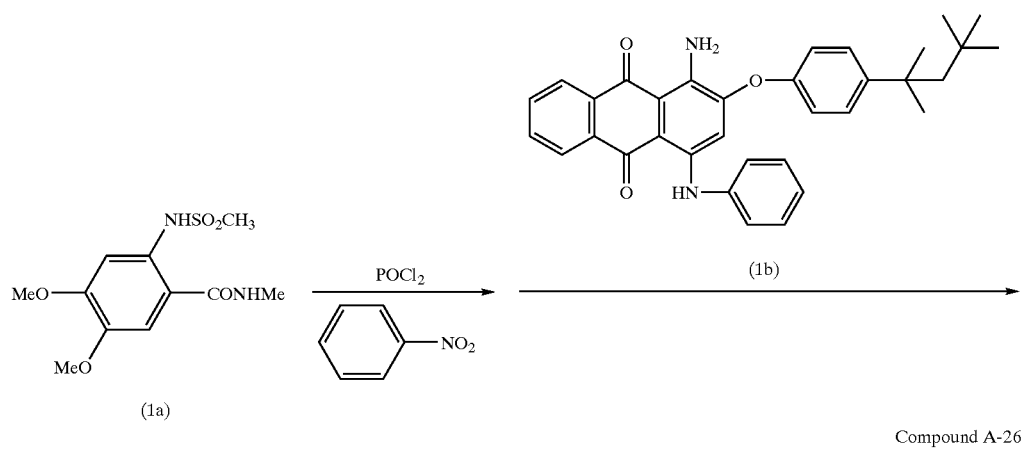

Compound A-26

To 75 ml of nitrobenzene was added 9.5 g (21.2 mmol) of compound (1a) and dissolved with heating at 90° C. Further thereto, 3.6 g (23.6 mmol) of phosphorus oxychloride was gradually added and stirred for 2 hr. Thereafter, 10 g (19.3 mmol) of compound (1b) was added and after the temperature was raised to 180° C., stirring continued for 2 hr. After completion of reaction, nitrobenzene was distilled under reduced pressure and remained oily material was subjected to chromatography to obtain red crystals of 3.4 g (yield: 23.3%).

The structure was identified by H-NMR and mass spectrum.

1H-NMR (CDCl$_3$), δ values, TMS standard: 0.67 (9H,s); 1.29 (6H, s); 1.72 (2H, s); 2.87 (3H, s); 3.96 (3H, s); 4.03 (3H, s); 6.92 (1H, s); 7.17–7.41 (10H, s); 7.82–7.88 (2H, m); 8.37 (1H, s); 8.59 (1H,d); 8.98 (1H, d).

(ii) Synthesis of Compound A-51

A mixture of 4.5 g of concentrated sulfuric acid and 4.5 g of fuming sulfuric acid was prepared under ice cooling and further thereto, 1.5 g of the compound (A-26), as synthesized above was added and allowed to react for a period of 2.5 hr. After completion of reaction, the reaction mixture was gradually poured to 25 of ice water and 1.5 g of common salt was added thereto and stirred for 30 min. The produced precipitate was filter off and the filtered powder was dissolved in 30 ml of water. The solution was again filter out to remove impurities and then, 2.4 g of common salt was again added to the filtrate and stirred for 1 hr. The produced precipitate was filtered off to obtain 1.3 g of a sodium salt of compound (A-51). The thus obtained sodium salt was identified by H-NMR to be a mixture of compounds differing in the number of sulfonic acid groups.

(iii) Synthesis of Compound B-1

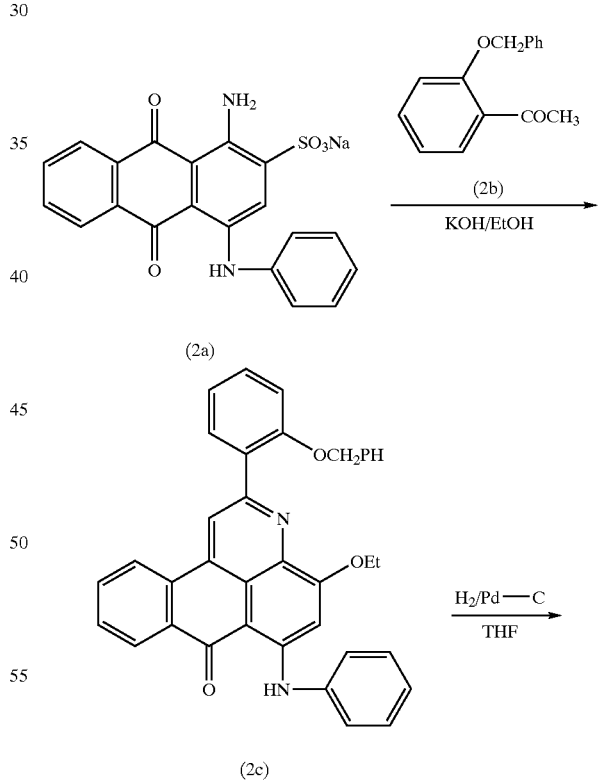

Compound B-1

Potassium hydroxide was dissolved in 30 ml of ethanol and 10 g (24.0 mmol) of compound (2a) was added thereto. Further thereto, 5.7 g (25.2 mmol) of compound (2b) was added and refluxed for 2 hr. After completion of reaction, the reaction mixture was allowed to stand to cool and the produced precipitate was filtered off. The precipitated was dissolved in 300 ml of THF and after filtering out to remove impurities, THF was distilled under reduced pressure and the remained precipitate was washed by suspending in toluene to obtain an intermediate (2c) of 4.3 g (yield: 32.7%).

The intermediate (2c) of 4.3 g was dissolved in 300 ml of THF and adding palladium-carbon thereto, hydrogenation was conducted at atmospheric pressure. After a given amount of hydrogen was absorbed and compound (2c) in the reaction mixture was confirmed disappear through TLC (thin layer chromatography), a catalyst was filtered out and solvent was distilled under reduced pressure. The obtained residue was washed by suspending in toluene to obtain 3.2 g of a red crystalline product (yield: 89.8%). The structure was identified by H-NMR and mass spectrum.

(iv) Synthesis of Compound B-21

Concentrated sulfuric acid of 4.5 g and 4.5 g of fuming sulfuric acid were mixed under ice cooling and thereto, 1.5 g of the compound (B-1), as synthesized above was added and allowed to react for a period of 2.5 hr. After completion of reaction, the reaction mixture was gradually poured to 25 of ice water and 1.5 g of common salt was added thereto and stirred for 30 min. The produced precipitate was filter off and the filtered powder was dissolved in 30 ml of water. The solution was again filter out to remove impurities and then, 2.4 g of common salt was again added to the filtrate and stirred for 1 hr. The produced precipitate was filtered off to obtain 1.1 g of a sodium salt compound (B-21). The thus obtained sodium salt was confirmed by H-NMR to be a mixture of compounds differing in the number of sulfonic acid groups.

(v) Synthesis of Compound (A-60)

To 16 ml of nitrobenzene was added 1.3 g (4.71 mmol) of compound (5a) and dissolved with heating at 90° C. Thereto, 0.96 g (6.29 mmol) of phosphorus oxychloride was gradually added and stirred for 2 hr. Then, 2.0 g (3.9 mmol) of compound (5b) was added, the temperature was raised to 130° C. and stirring continued for 1 hr. Thereafter, the reaction mixture was allowed to stand to cool until reached 70° C., 0.48 g (3.14 mmol) of phosphorus oxychloride was gradually added, the temperature was again raised to 130° C. and stirring further continued for 1 hr. After completion of reaction, 50 ml of n-hexane was added to the reaction mixture and decanted to obtain 4 g of a yellowish orange-colored residue. The residue was subjected to column chromatography to obtain a yellow crystalline residue. The thus obtained residue was identified by NMR and mass spectrum to be an intended compound.

(vi) Synthesis of Compound A-80

Concentrated sulfuric acid of 5.2 g and 5.2 g of fuming sulfuric acid were mixed under ice cooling and thereto, 1.5 g of the compound (A-64), as synthesized above was added and allowed to react for a period of 3 hr. After completion of reaction, the reaction mixture was gradually poured to 25 of ice water and 1.5 g of common salt was added thereto and stirred for 30 min. The produced precipitate was filter off and the filtered powder was dissolved in 30 ml of water. The solution was again filter out to remove impurities and then, 2.5 g of common salt was again added to the filtrate and stirred for 1 hr. The produced precipitate was filtered off to obtain 1.27 g of a sodium salt of compound (B-21). The thus obtained sodium salt was confirmed by H-NMR to be a mixture of compounds differing in the number of sulfonic acid groups.

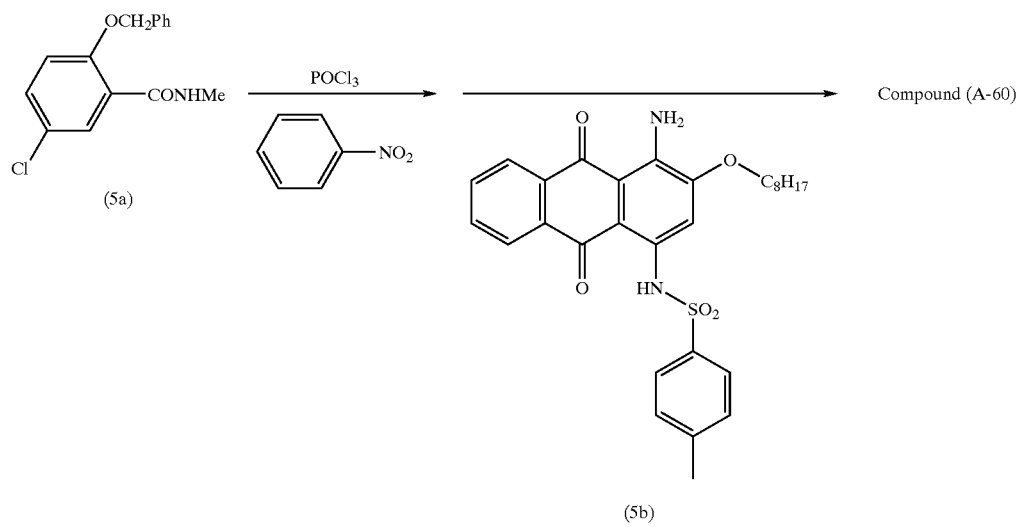

(vii) Synthesis of Compound (B-42)

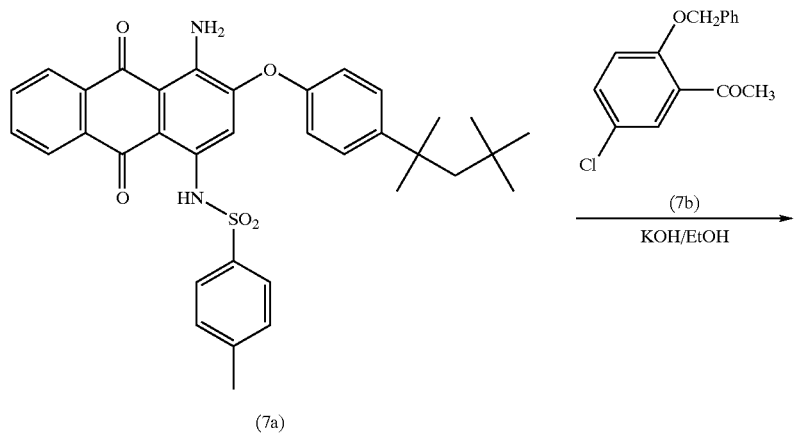

(7a)

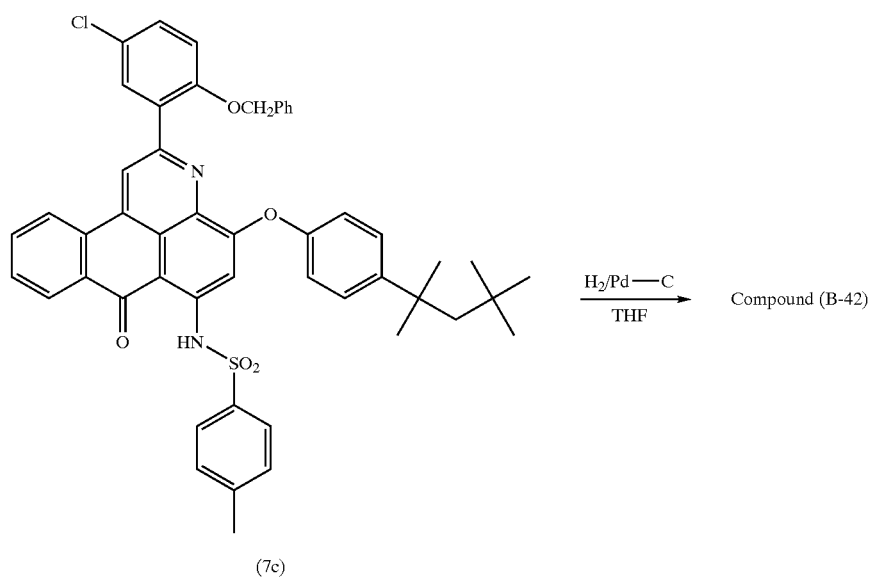

(7c)

Potassium hydroxide of 2 g was dissolved in 35 ml of ethanol and 8 g (13.4 mmol) of compound (7a) was added thereto. Further thereto, 3.8 g (14.74 mmol) of compound (7b) was added and refluxed for 2 hr. After completion of reaction, the reaction mixture was allowed to stand to cool and the produced precipitate was filtered off. The precipitated was dissolved in 250 ml of THF and after filtering out to remove impurities, THF was distilled under reduced pressure and the remained precipitate was washed by suspending in toluene to obtain an intermediate (7c) of 5.7 g (yield: 52.3%).

The intermediate (7c) of 5.7 g was dissolved in 220 ml of THF and adding palladium-carbon thereto, hydrogenation was conducted at atmospheric pressure. After a given amount of hydrogen was absorbed and compound (7c) in the reaction mixture was confirmed to disappear through TLC, a catalyst was filtered out and solvent was distilled under reduced pressure. The obtained residue was washed by suspending in toluene to obtain 4.7 g of a red crystalline product (yield: 92.3%). The structure was identified by H-NMR and mass spectrum.

There are shown below comparative compounds used for preparation of comparative inks used in Example 2 through 4 described later.
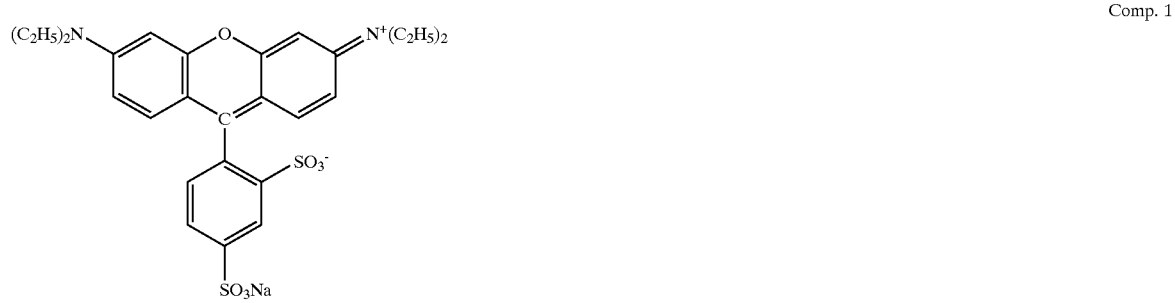
Comp. 1
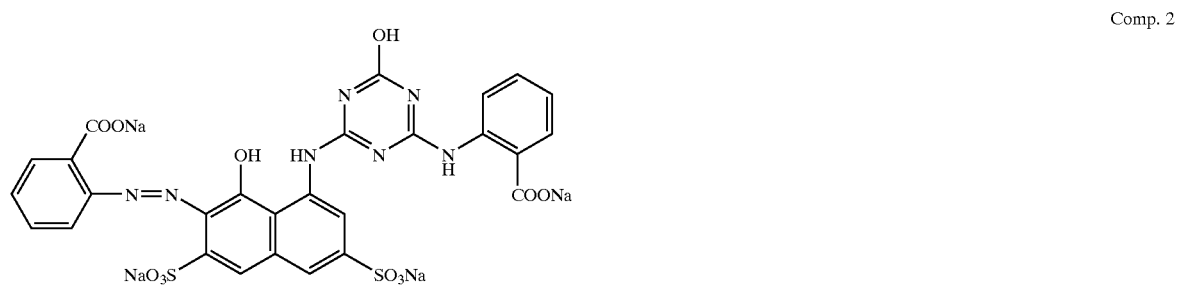
Comp. 2
Comp. 3        Comp. 4
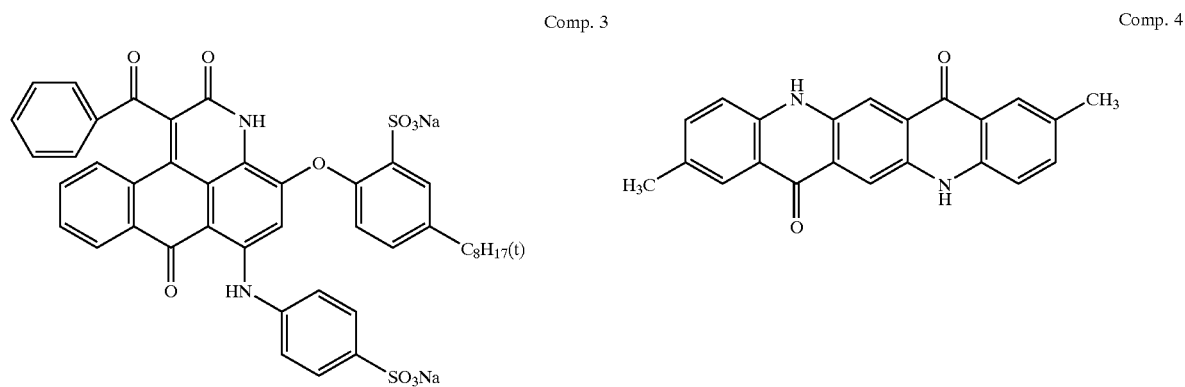
Comp. 5        Comp. 6
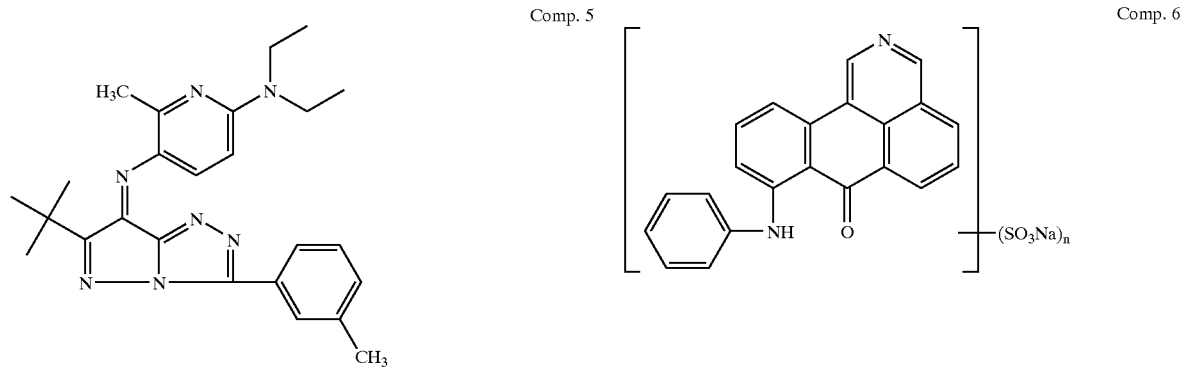

-continued
Comp. 7
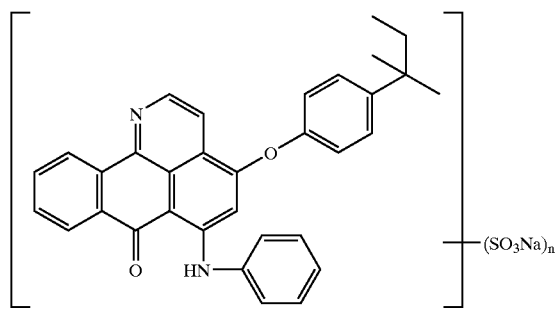
Comp. 8
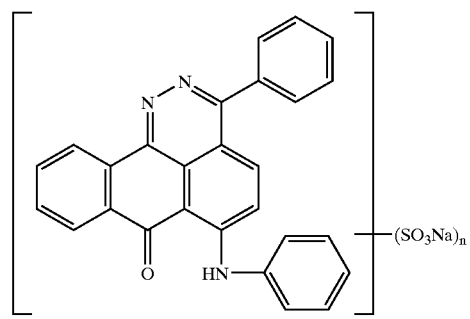
Comp. 9
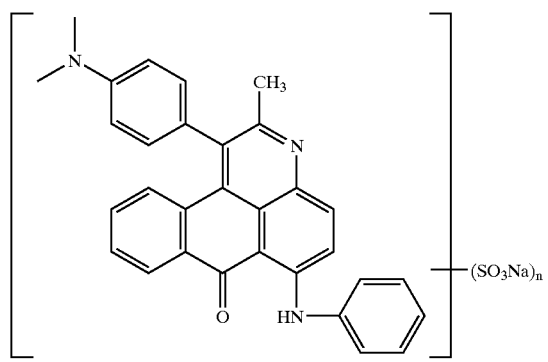
Comp. 10
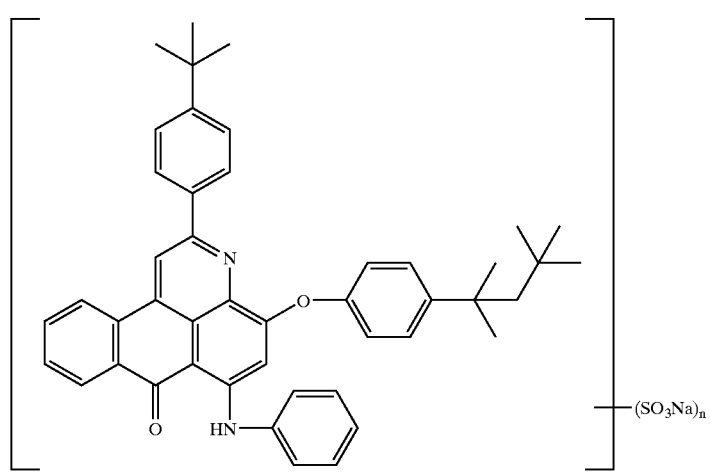
Comp. 11
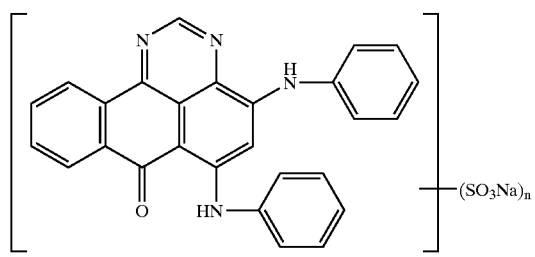

-continued
Comp. 12
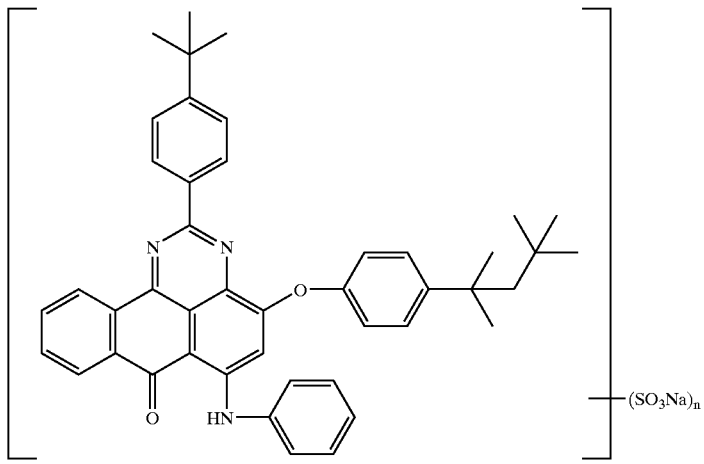
Comp. 13
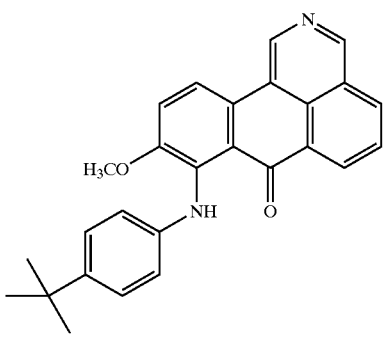
Comp. 14
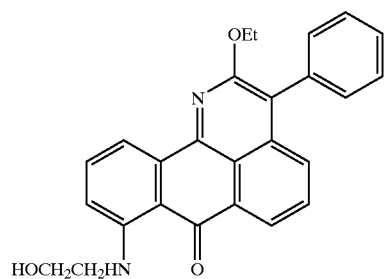
Comp. 15
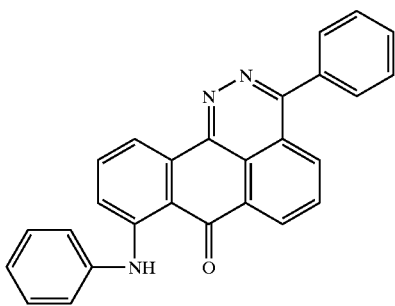
Comp. 16
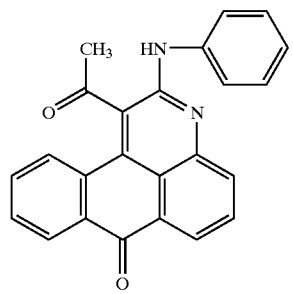
Comp. 17
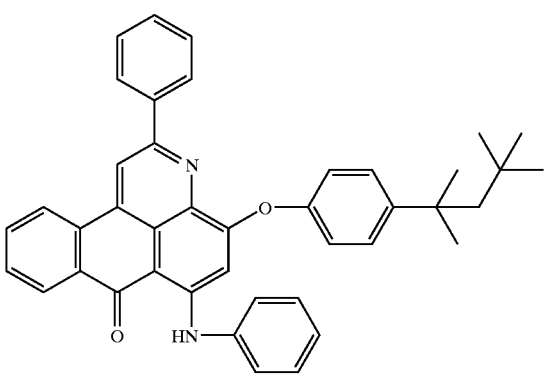
Comp. 18
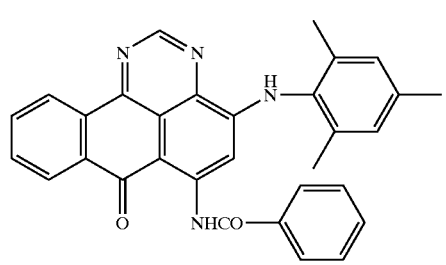

-continued
Comp. 19
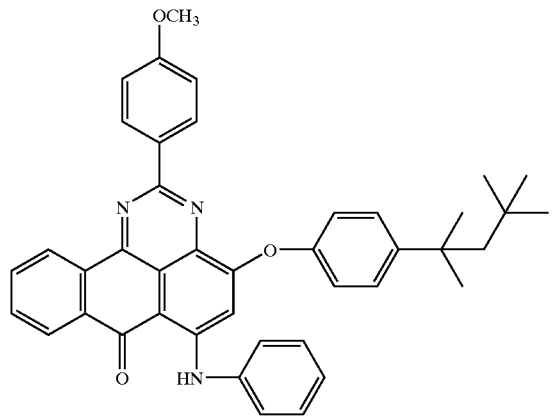
Comp. 20
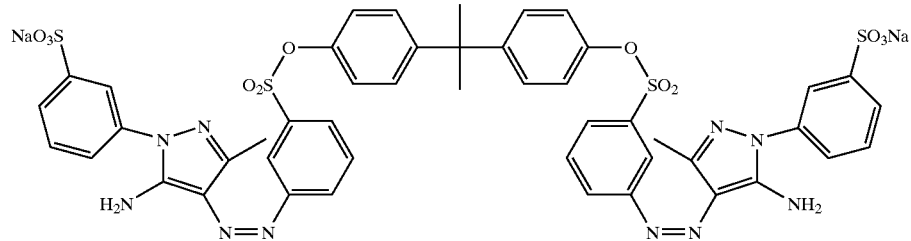
Comp. 21
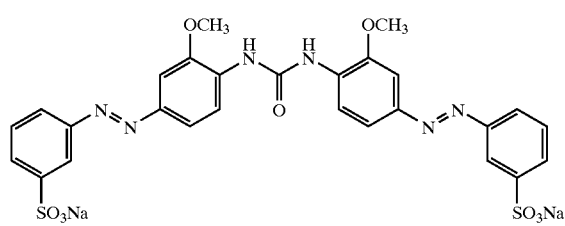
Comp. 22
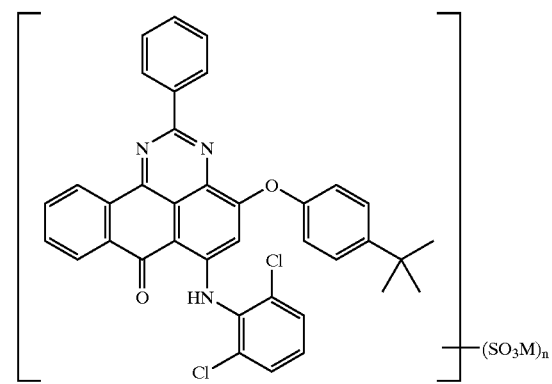
Comp. 23
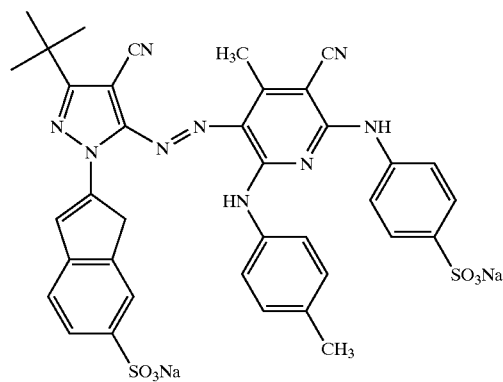
Comp. 24
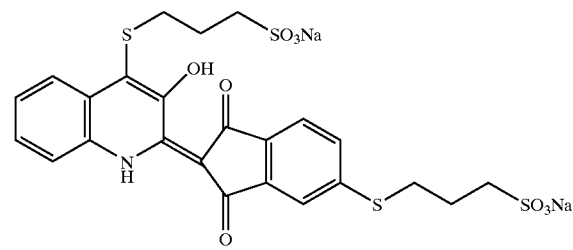

-continued

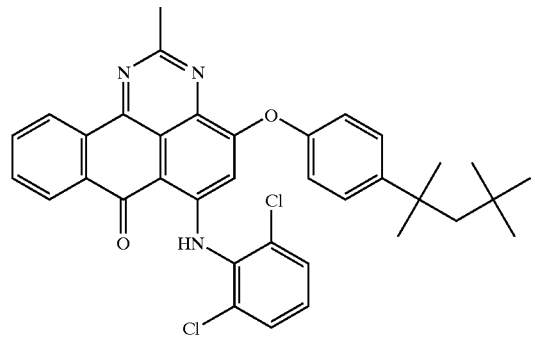
Comp. 25

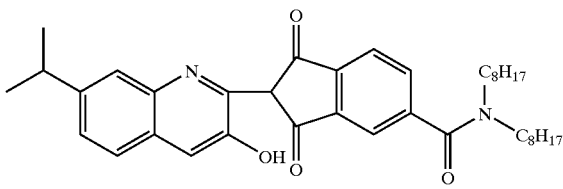
Comp. 26

Example 2

Preparation of Water-based Ink

Dyes shown in Table 1 were each weighed out so that the dye content of the ink was made to 2% by weight. The respective dyes were dissolved so as to prepare a solution comprised of ethylene glycol (15%), glycerin (15%), Surfinol 465 (available from Nisshin Kagaku Kogyo Co., Ltd., 0.3%) and water. The thus prepared solutions were each filtered out through a membrane filter of 2 μm to remove dusts and coarse particles to obtain inks for ink jet printing, Nos. 1 through 22.

Preparation of Print Sample and Evaluation

Using the foregoing inks in a commercially available ink jet printer (PM-800, available from Seiko Epson Corp.), ink jet printing was performed onto Konica Photo Jet Paper (Photolike QP, glossy paper, available from Konica Corp.). The obtained images were evaluated with respect to light stability, according to the following procedure.

Light Stability

Using a xenon weather-meter (produced by Suga Shikenki Co., Ltd.), print samples were exposed xenon light (70,000 lux) for 48 hr. and lowering percentage in reflection density at the absorption maximum in the visible region from an unexposed sample, according to the following equation:

Light stability (%)=(density at absorption maximum of exposed sample)/(density at absorption maximum of unexplored sample)×100

Results thereof shown in Table 1.

TABLE 1

| Ink No. | Dye | Light Stability | Remark |
|---|---|---|---|
| 1 | Comp. 1 | 10 | Comp. |
| 2 | Comp. 2 | 41 | Comp. |
| 3 | Comp. 3 | 55 | Comp. |
| 4 | Comp. 6 | 66 | Comp. |
| 5 | Comp. 7 | 68 | Comp. |
| 6 | Comp. 8 | 64 | Comp. |
| 7 | Comp. 9 | 66 | Comp. |
| 8 | Comp. 10 | 75 | Comp. |
| 9 | Comp. 11 | 67 | Comp. |
| 10 | Comp. 12 | 77 | Comp. |
| 11 | A-29 | 91 | Inv. |
| 12 | A-30 | 92 | Inv. |
| 13 | A-34 | 86 | Inv. |

TABLE 1-continued

| Ink No. | Dye | Light Stability | Remark |
|---|---|---|---|
| 14 | A-51 | 91 | Inv. |
| 15 | B-21 | 88 | Inv. |
| 16 | B-28 | 88 | Inv. |
| 17 | B-38 | 85 | Inv. |
| 18 | C-10 | 82 | Inv. |
| 19 | D-10 | 81 | Inv. |
| 20 | E-10 | 83 | Inv. |
| 21 | F-8 | 83 | Inv. |
| 22 | G-11 | 80 | Inv. |

As can be seen from Table 1, it was proved that inks according to this invention exhibited superior light stability, compared to comparative inks.

Example 3

Preparation of Fine Particle Dispersion

To a mixture of 10 g of a dye described in Table 2, 20 g of methyl ethyl ketone, 5 g of glycerin, 6 g of neutralized resin of styrene/acrylic acid/2-hydroxyethy methacrylate (80/5/15) and 40 g of deionized water was added 250 g of zirconia beads of an average particle size of 0.5 mm and dispersed for 4 hr., using media dispersing machine (System Zeta, available from Ashizawa Co., Ltd.). After completion of dispersing, zirconia beads were filtered out to obtain a dye dispersion. The dye dispersion was diluted with 40 ml water and methyl ethyl ketone was distilled under reduced pressure to obtain a dispersion of fine dye particles.

Preparation of Water-based Ink

Dyes shown in Table 2 were each weighed out so that the dye content of the ink was made to 3% by weight. The respective dyes were dissolved to prepare a solution comprised of ethylene glycol (15 wt %), glycerin (15 wt %), triethylene glycol monobutyl ether (3 wt %), Surfinol 465 (0.3%) and water. The thus prepared solutions were each filtered out through a membrane filter of 2 μm to remove dusts and coarse particles to obtain inks for ink jet printing, Nos. 23 through 33.

Preparation of Print Sample and Evaluation

The thus prepared inks were evaluated with respect to light stability of the print samples, similarly to Example 1. The inks were also aged for 7 days at 60° C. and evaluated with respect to variation of dye particle size and filterability of the aged ink, according to the procedure described below. The dye particle size refers to an average particle size, which was determined using Zeta Sizer 1000, available from Malbahn Co.

Particle Size Variation

The respective inks were aged for 7 days at 60° C. and evaluated with respect to variation ratio of dye particle size between before and after being aged, based on the following criteria:

A: less than 5%;

B: not less than 5% and less than 10%;

C: more than 10%; in which A and B are acceptable levels in practice.

Filterability

After being aged for 7 days at 60° C., 5 ml of the aged ink was filtered through cellulose acetate membrane filter of 0.8 μm, filterability was evaluated based on the following criteria:

A: the whole amount was filter;

B: at least a half amount was filtered;

C: more than a half amount was not filtered;

in which A and B are acceptable levels in practice.

Results are shown in Table 2.

TABLE 2

| Ink No. | Dye | Light Stability | Particle Size Variation | Filter-ability | Remark |
|---|---|---|---|---|---|
| 23 | Comp. 4 | 59 | B | B | Comp. |
| 24 | Comp. 5 | 61 | C | B | Comp. |
| 25 | Comp. 17 | 71 | B | A | Comp. |
| 26 | Comp. 18 | 67 | B | A | Comp. |
| 27 | A-26 | 83 | B | A | Inv. |
| 28 | B-1 | 81 | B | A | Inv. |
| 29 | C-2 | 78 | B | A | Inv. |
| 30 | D-5 | 77 | B | A | Inv. |
| 31 | E-7 | 75 | B | A | Inv. |
| 32 | F-6 | 78 | B | A | Inv. |
| 33 | G-7 | 77 | B | A | Inv. |

As can be seen from Table 2, it was proved that inks according to this invention exhibited superior storage stability, compared to comparative inks.

Example 4

Preparation of Fine Particle Dispersion

A 5 g dye shown in Table 3, 5 f g of polyvinyl butyral (BL-S, available from Sekisui Kagaku Co., mean polymerization degree of 350) and 50 g of ethyl acetate were put into a separable flask and after replacing the atmosphere inside the flask by $N_2$, the foregoing dye and polymer were completely dissolved. Then, 100 g of an aqueous solution containing 2 g of sodium laurylsulfate was dropwise added and emulsified using a ultrasonic homogenizer (UH-150 Type, available from S.T.M. Co.) over a period of 300 sec. Thereafter, ethyl acetate was distilled under reduced pressure to obtain a dispersion of fine colored particles impregnated with a dye. To the dispersion, 0.15 g of potassium persulfate was added and dissolved. After heating the solution to 70° C. by a heater, a mixture solution of 2 g of styrene and 1 g of 2-hydroxyethyl methacrylate was dropwise added and allowed to react for 7 hr. to obtain fine core/shell type colored particles.

Preparation of Water-based Ink

Dyes shown in Table 3 were each weighed out so that the dye content of the ink was made to 3% by weight. The respective dyes were dissolved to prepare a solution composed of ethylene glycol (15 wt %), glycerin (15 wt %), triethylene glycol monobyrly ether (3 wt %) Srufinol 465 (0.3%) and water. The thus prepared solutions were each filtered out through a membrane filter of 2 μm to remove dusts and coarse particles to obtain inks for jet printing, Nos. 34 through 53.

Preparation of Print Sample and Evaluation

Similarly to Examples 3, the thus prepared inks were aged for 7 days at 60° C. evaluated with respect to light stability, variations of dye particle size and filterability of the aged ink. Results are shown in Table 3.

TABLE 3

| Ink No. | Dye | Light Stability | Particle Size Variation | Filter-ability | Remark |
|---|---|---|---|---|---|
| 34 | Comp. 5 | 62 | C | B | Comp. |
| 35 | Comp. 13 | 64 | B | A | Comp. |
| 36 | Comp. 14 | 69 | B | A | Comp. |
| 37 | Comp. 15 | 66 | B | A | Comp. |
| 38 | Comp. 16 | 68 | B | A | Comp. |
| 39 | Comp. 17 | 71 | B | A | Comp. |
| 40 | Comp. 18 | 69 | B | A | Comp. |
| 41 | Comp. 19 | 73 | B | A | Comp. |
| 42 | A-2 | 89 | B | A | Inv. |
| 43 | A-3 | 90 | B | A | Inv. |
| 44 | A-20 | 89 | B | A | Inv. |
| 45 | A-26 | 85 | B | A | Inv. |
| 46 | B-1 | 85 | B | A | Inv. |
| 47 | B-2 | 87 | B | A | Inv. |
| 48 | B-15 | 83 | B | A | Inv. |
| 49 | C-2 | 80 | B | A | Inv. |
| 50 | D-5 | 80 | B | A | Inv. |
| 51 | E-7 | 76 | B | A | Inv. |
| 52 | F-6 | 78 | B | A | Inv. |
| 53 | G-7 | 78 | B | A | Inv. |

As can be seen from Table 3, it was proved that the use of the dyes according to this invention led to an ink exhibiting superior light stability and storage stability, as compared to comparative inks.

Example 5

Preparation of Water-based Ink

Dyes shown in Table 4 were each weighed out so that the dye content of the ink was made to 2% by weight. The respective dyes were dissolved to prepare a solution composed of ethylene glycol (15 wt %), glycerin (15 wt %), Surfinol 465 (0.3%) and water. The thus prepared solutions were each filtered out through a membrane filter of 2 μm to remove dusts and coarse particles to obtain inks for ink jet printing, Nos. 61 through 82.

Similarly to Example 2, print samples were prepared and evaluated with light stability of printed images. Thus, using a xenon weather-meter (produced by Suga Shikenki Co., Ltd.), print samples were exposed xenon light (70,000 lux) for 7 days and lowering percentage in reflection density at the absorption maximum in the visible region from an unexposed sample, according to the following equation:

Light stability (%)=(density at absorption maximum of exposed sample)/(density at absorption maximum of unexposed sample)×100

Results thereof are shown in Table 4.

TABLE 4

| Ink No. | Dye | M | n | Light Stability | Remark |
|---|---|---|---|---|---|
| 61 | Comp. 20 | — | — | 12 | Comp. |
| 62 | Comp. 21 | — | — | 48 | Comp. |
| 63 | Comp. 22 | Na | 2 | 62 | Comp. |
| 64 | Comp. 23 | — | — | 73 | Comp. |
| 65 | Comp. 24 | — | — | 46 | Comp. |
| 66 | A-71 | Na | 2 | 92 | Inv. |
| 67 | A-72 | Na | 3 | 91 | Inv. |
| 68 | A-76 | Na | 2 | 96 | Inv. |
| 69 | A-78 | Na | 4 | 93 | Inv. |
| 70 | A-80 | — | — | 92 | Inv. |
| 71 | A-82 | K | 2 | 95 | Inv. |
| 72 | A-84 | Li | 1 | 93 | Inv. |
| 73 | A-88 | — | — | 94 | Inv. |
| 74 | A-92 | — | — | 93 | Inv. |
| 75 | A-94 | — | — | 94 | Inv. |
| 76 | B-58 | K | 3 | 92 | Inv. |
| 77 | B-59 | (N-Bu$_4$) | 3 | 93 | Inv. |
| 78 | B-61 | Na | 1 | 94 | Inv. |
| 79 | B-62 | Na | 2 | 93 | Inv. |
| 80 | B-63 | Li | 2 | 92 | Inv. |
| 81 | B-66 | Na | 3 | 94 | Inv. |
| 82 | B-68 | Na | 2 | 93 | Inv. |

As seen be seen from Table 4, it was proved that the use of the dyes according to this invention led to an ink exhibiting superior light stability, compared to comparative inks.

Example 6

Preparation of Fine Particle Dispersion

To a mixture of 10 g of a dye described in Table 5, 20 g of methyl ethyl ketone, 5 g of glycerin, 6 g of neutralized resin of styrene/acrylic acid/2-hydroxyethy methacrylate (80/5/15) and 40 g of deionized water was added 250 g of zirconia beads of an average particle size of 0.5 mm and dispersed for 4 hr. using media dispersing machine (System Zeta, available from Ashizawa Co., Ltd.). After completion of dispersing, zirconia beads were filtered out to obtain dye dispersion. The dye dispersion was diluted with 40 ml water and methyl ethyl ketone was distilled under reduced pressure to obtain a dispersion of fine dye particles.

Preparation of Water-based Ink

Dyes shown in Table 5 were each weighed out so that the dye content of the ink was made to 3% by weight. The respective dyes were dissolved to prepare a solution comprised of ethylene glycol (15 wt %), glycerin (15 wt %), triethylene glycol monobutyl ether (3 wt %), Surfinol 465 (0.3%) and water. The thus prepared solutions were each filtered out through a membrane filter of 2 um to remove dusts and coarse particles to obtain inks for ink jet printing, Nos. 83 through 92.

Preparation of Print Sample and Evaluation

The thus prepared inks were evaluated with respect to light stability of the print samples similarly to Example 5. The inks were also aged for 7 days at 60° C. and evaluated with respect to variation of dye particle size and filterability of the aged ink, similarly to Example 3. Results shown in Table 5.

TABLE 5

| Ink No. | Dye | Light Stability | Particle Size Variation | Filterability | Remark |
|---|---|---|---|---|---|
| 83 | Comp. 25 | 59 | B | A | Comp. |
| 84 | Comp. 26 | 42 | C | B | Comp. |
| 85 | A-56 | 93 | B | A | Inv. |
| 86 | A-58 | 94 | B | A | Inv. |
| 87 | A-60 | 95 | B | A | Inv. |
| 88 | A-64 | 92 | B | A | Inv. |
| 89 | B-42 | 94 | B | A | Inv. |
| 90 | B-46 | 93 | B | A | Inv. |
| 91 | B-52 | 94 | B | A | Inv. |
| 92 | B-55 | 93 | B | A | Inv. |

As can be seen from Table 5, it was proved that the use of the dyes according to this invention led to an ink exhibiting superior storage stability, compared to comparative ink.

Example 7

Preparation of Fine Particle Dispersion

A 5 g dye shown in Table 6, 5 f g of polyvinyl butyral (BL-S, available from Sekisui Kagaku Co., mean polymerization degree of 350) and 50 g of ethyl acetate were put into a separable flask and after replacing the atmosphere inside the flask by $N_2$, the foregoing dye and polymer were completely dissolved. Then, 100 g of an aqueous solution containing 2 g of sodium laurylsulfate was dropwise added and emulsified using a ultrasonic homogenizer (UH-150 Type, available from S.T.M. Co.) over a period of 300 sec. Thereafter, ethyl acetate was distilled under reduced pressure to obtain a dispersion of fine colored particles impregnated with a dye. To the dispersion, 0.15 g of potassium persulfate was added and dissolved. After heating the solution to 70° C. by a heater, a mixture solution of 2 g of styrene and 1 g of 2-hydroxyethyl methacrylate was dropwise added and allowed to react for 7 hr. to obtain fine core/shell type colored particles.

Preparation of Water-based Ink

Dyes shown in Table 3 were each weighed out so that the dye content of the ink was made to 3% by weight. The respective dyes were dissolved to prepare a solution composed of ethylene glycol (15 wt %), glycerin (15 wt %), triethylene glycol monobutyl ether (3 wt %) Surfinol 465 (0.3%) and water. The thus prepared solutions were each filtered out through a membrane filter of 2 μm to remove dusts and coarse particles to obtain inks for in jet printing, Nos. 93 through 106.

Preparation of Print Sample and Evaluation

The inks were aged for 7 days at 60° C. and evaluated with respect to variation of dye particle size and filterability of the aged ink, similarly to Example 3. Results are shown in table 5. The inks were also evaluated with respect to light stability of the print samples similarly to Example 5. Results are shown in Table 6.

TABLE 6

| Ink No. | Dye | Light Stability | Particle Size Variation | Filter-ability | Remark |
|---|---|---|---|---|---|
| 93 | Comp. 25 | 61 | B | A | Comp. |
| 94 | Comp. 26 | 48 | C | B | Comp. |
| 95 | A-55 | 92 | B | A | Inv. |
| 96 | A-57 | 91 | B | A | Inv. |
| 97 | A-58 | 90 | B | A | Inv. |
| 98 | A-60 | 96 | B | A | Inv. |
| 99 | A-61 | 93 | B | A | Inv. |
| 100 | A-66 | 95 | B | A | Inv. |
| 101 | A-69 | 92 | B | A | Inv. |
| 102 | B-41 | 91 | B | A | Inv. |
| 103 | B-45 | 94 | B | A | Inv. |
| 104 | B-47 | 93 | B | A | Inv. |
| 105 | B-51 | 95 | B | A | Inv. |
| 106 | B-56 | 94 | B | A | Inv. |

As can be seen from Table 6, it was proved that the use of the dyes according to this invention led to inks exhibiting superior storage stability and light stability, compared to comparative inks.

The invention claimed is:

1. A dye represented by the following formula (1):

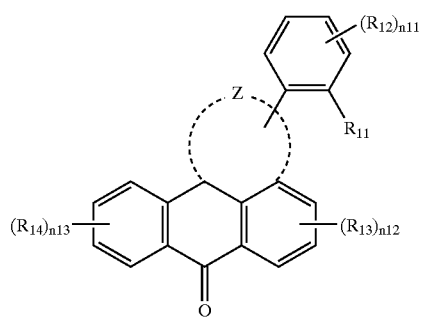

formula (1)

wherein Z is an atomic group necessary to form a 6-membered nitrogen containing aromatic ring; $R_{11}$ is a hydrogen bonding group selected from the group consisting of —OH, —NHCOR$_4$ —NHCOOR$_4$, —NHCONHR$_4$, —NHSO$_2$R$_4$ and —NHSO$_2$NHR$_4$, in which R$_4$ is a substituent; $R_{12}$, $R_{13}$ and $R_{14}$ are independently a hydrogen atom or a substituent; n11 and n13 are each an integer of 1 to 4; n12 is an integer of 1 to 3.

2. The dye of claim 1, wherein the dye represented by formula (1) is a dye represented by the following formula (2), (3), (4), (5), (6) or (7):

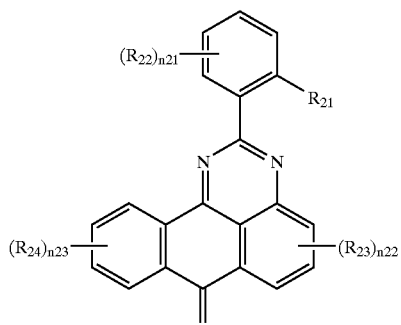

formula (2)

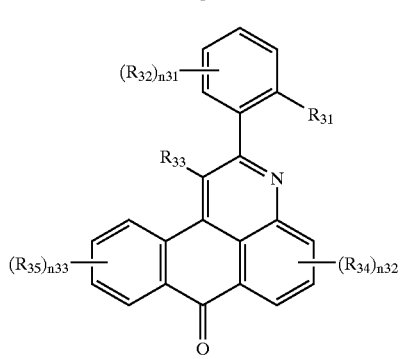

formula (3)

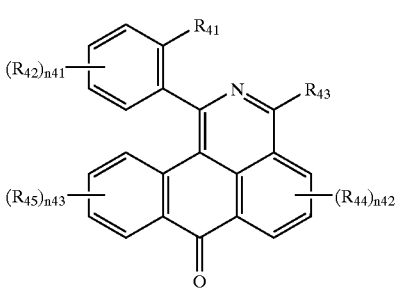

(formula (4)

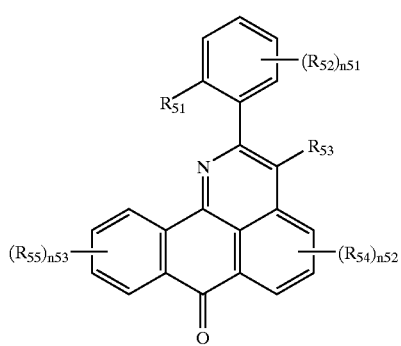

formula (5)

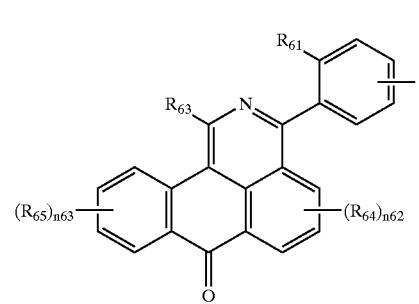

formula (6)

-continued formula (7)

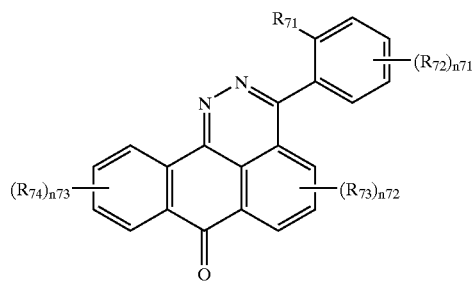

wherein $R_{21}$, $R_{31}$, $R_{41}$, $R_{51}$, $R_{61}$ and $R_{71}$, are each a hydrogen bonding atom; $R_{22}$, $R_{23}$, $R_{24}$, $R_{32}$, $R_{33}$, $R_{34}$, $R_{35}$, $R_{42}$, $R_{43}$, $R_{44}$, $R_{45}$, $R_{52}$, $R_{53}$, $R_{54}$, $R_{55}$, $R_{62}$, $R_{63}$, $R_{64}$, $R_{65}$, $R_{72}$, $R_{73}$, and $R_{74}$ are independently a substituent; n21, n23, n31, n33, n41, n43, n51, n53, n61, n63, n71 and n73 are each an integer of 1 to 4; n22, n32, n42, n52, n62 and n72 each an integer of 1 to 3.

3. The dye of claim 2, wherein the dye represented by formula (1) is a dye represented by formula (2) or (3).

4. The dye of claim 3, wherein the dye represented by formula (2) is a dye represented by the following formulas (8) or (9), and the dye represented by formula (3) is a dye represented by the following formulas (10) or (11):

formula (8)

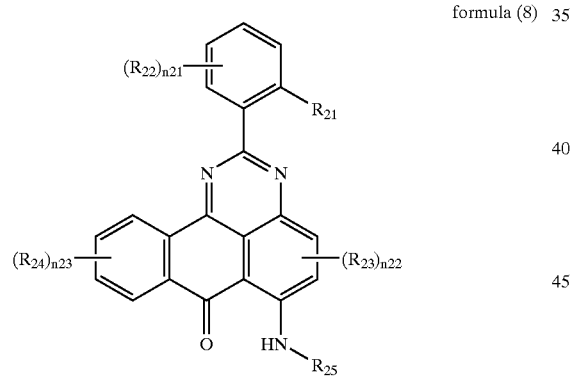

formula (9)

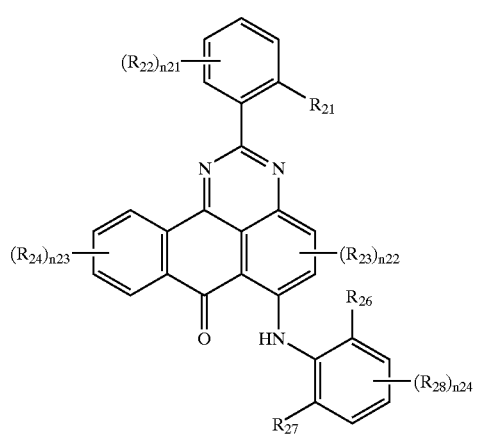

formula (10)

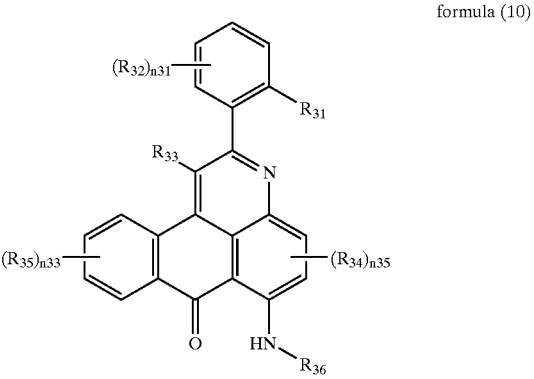

formula (11)

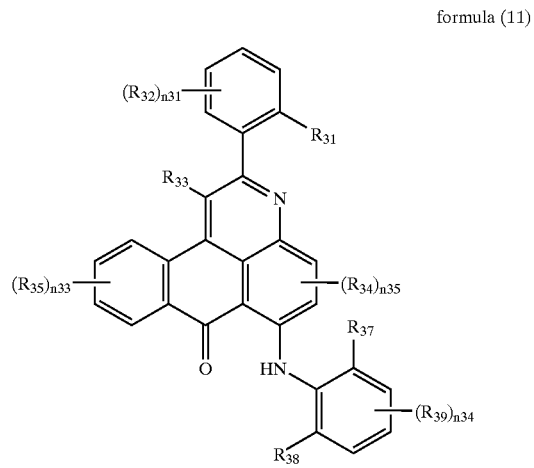

wherein $R_{21}$ and $R_{31}$ are independently a hydrogen bonding group; $R_{22}$, $R_{23}$, $R_{24}$, $R_{28}$, $R_{32}$, $R_{33}$, $R_{34}$, $R_{35}$ and $R_{39}$ are independently a hydrogen atom or a substituent; $R_{26}$, $R_{27}$, $R_{37}$ and $R_{38}$ are independently a substituent; n21, n23, n31, and n33 are each an integer of 1 to 4; n24 and n34 are each an integer of 1 to 3; n25 and n35 are each an integer of 1 or 2; $R_{25}$ and $R_{36}$ are independently a group having a Hammett substituent constant ($\sigma p$) of 0.3 to 1.0.

5. The dye of claim 3, wherein the dye represented by formula (2) is a dye represented by the following formula (12), and the dye represented by formula (3) is a dye represented by the following formula (13):

formula (12)

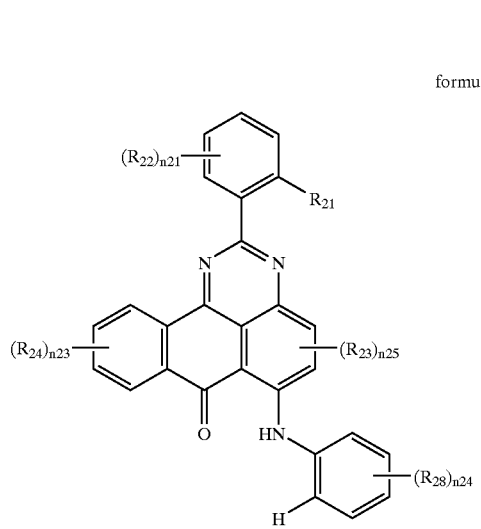

formula (1)

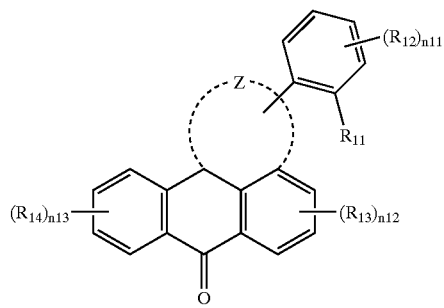

wherein Z is an atomic group necessary to form a 6-membered nitrogen containing aromatic ring; $R_{11}$ is a hydrogen bonding group; selected from the group consisting of —OH, —NHCOR$_4$ —NHCOOR$_4$, —NHCONHR$_4$, —NHSO$_2$R$_4$ and —NHSO$_2$NHR$_4$, in which R$_4$ is a substituent; $R_{12}$, $R_{13}$ and $R_{14}$ are independently a hydrogen atom or a substituent; n11 and n13 are each an integer of 1 to 4; n12 is an integer of 1 to 3.

7. The ink of claim 6, wherein the dye represented by formula (1) is a dye represented by the following formula (2), (3), (4), (5), (6) or (7):

formula (13)

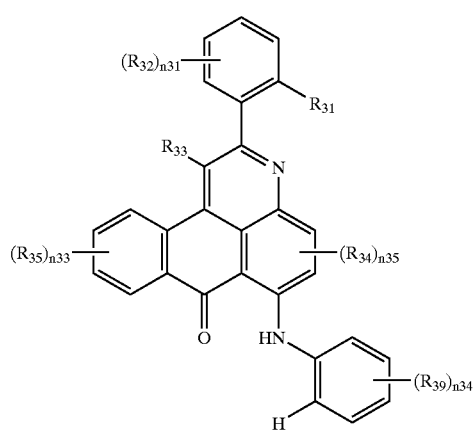

formula (2)

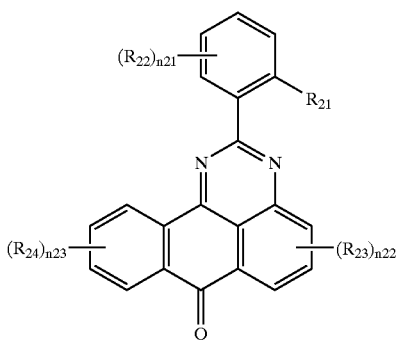

wherein $R_{21}$, and $R_{31}$ are independently a hydrogen bonding group; $R_{22}$, $R_{23}$, $R_{24}$, $R_{28}$, $R_{32}$, $R_{33}$, $R_{34}$, $R_{35}$ and $R_{39}$ are independently a hydrogen atom or a substituent; n21, n23, n24, n31, n33, and n34 are each an integer of 1 to 4; n25 and n35 is an integer of 1 or 2.

6. An ink for ink jet printing comprising a dye represented by the following formula (1) and a solvent:

formula (3)

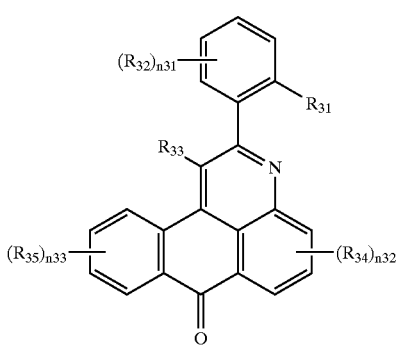

115

-continued

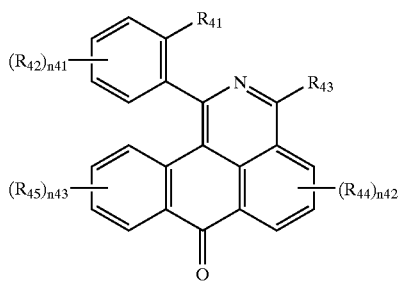

formula (4)

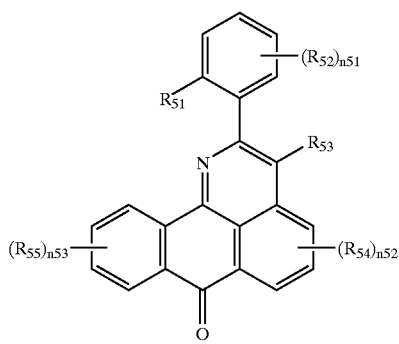

formula (5)

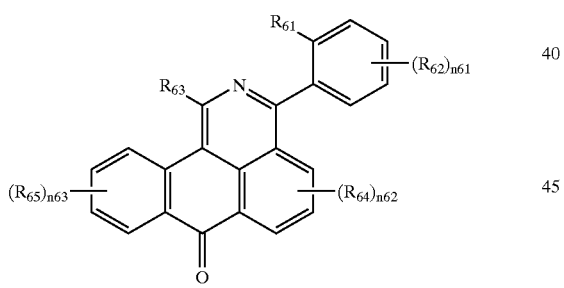

formula (6)

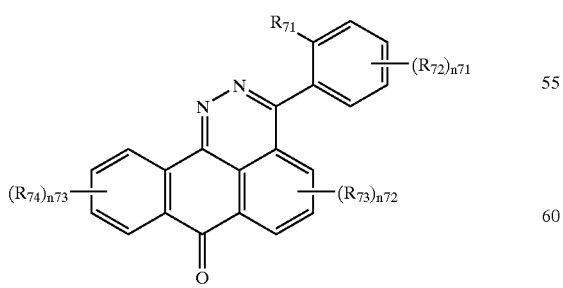

formula (7)

wherein $R_{21}$, $R_{31}$, $R_{41}$, $R_{51}$, $R_{61}$ and $R_{71}$ are each a hydrogen bonding atom; $R_{22}$, $R_{23}$, $R_{24}$, $R_{32}$, $R_{33}$, $R_{34}$, $R_{35}$, $R_{42}$, $R_{43}$, $R_{44}$, $R_{45}$, $R_{52}$, $R_{53}$, $R_{54}$, $R_{55}$, $R_{62}$, $R_{63}$, $R_{64}$, $R_{65}$, $R_{72}$, $R_{73}$, and $R_{74}$ are independently a hydrogen atom or a substituent; n21, n23, n31, n33, n41, n43, n51, n53, n61, n63, n71 and n73 are each an integer of 1 to 4, n22, n32, n42, n52, n62 and n72 are each an integer of 1 to 3.

8. The ink of claim 7, wherein the dye represented by formula (1) is a dye represented by formula (2) or (3).

9. The ink of claim 8, wherein the dye represented by formula (2) is a dye represented by the following formulas (8) or (9), and the dye represented by formula (3) is a dye represented by the following formulas (10) or (11):

formula (8)

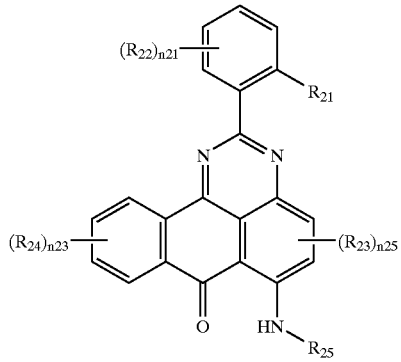

formula (9)

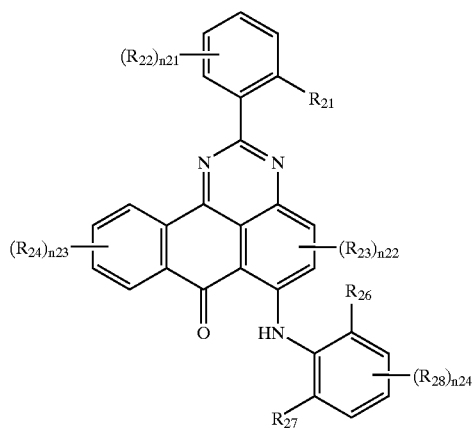

formula (10)

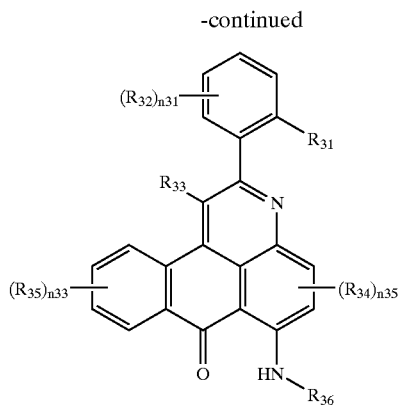

formula (11)

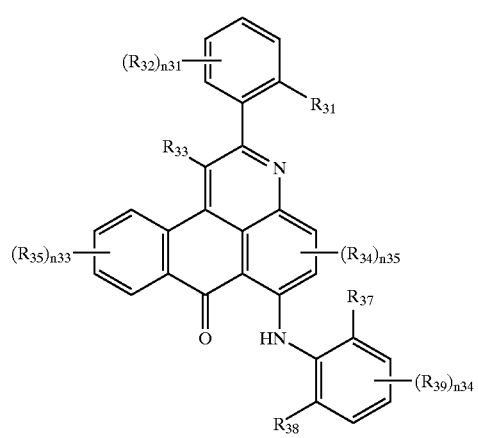

formula (12)

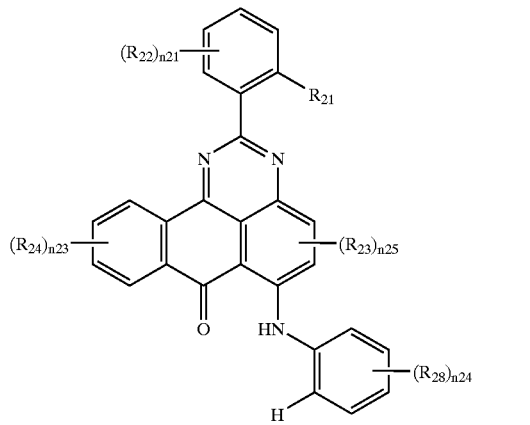

formula (13)

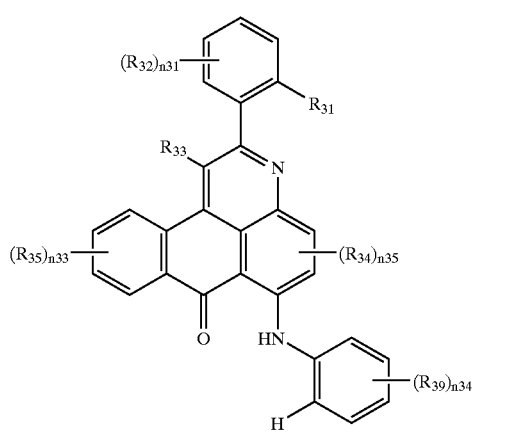

wherein $R_{21}$ and $R_{31}$ are independently a hydrogen bonding group; $R_{22}$, $R_{23}$, $R_{24}$, $R_{28}$, $R_{32}$, $R_{33}$, $R_{34}$, $R_{35}$ and $R_{39}$ are independently a hydrogen atom or a substituent; $R_{26}$, $R_{27}$, $R_{37}$ and $R_{38}$ are independently a substituent; n21, n23, n31, and n33 are each an integer of 1 to 4; n24 and n34 are each an integer of 1 to 3; n25 and n35 are each an integer of 1 or 2; $R_{25}$ and $R_{36}$ are independently a group having a Hammett substituent constant (σp) of 0.3 to 1.0.

10. The ink of claim 8, wherein the dye represented by formula (2) is a dye represented by the following formula (12), and the dye represented by formula (3) is a dye represented by the following formula (13):

wherein $R_{21}$ and $R_{31}$ are independently a hydrogen bonding group; $R_{22}$, $R_{23}$, $R_{24}$, $R_{28}$, $R_{32}$, $R_{33}$, $R_{34}$, $R_{35}$ and $R_{39}$ are independently a hydrogen atom or a substituent; n21, n23, n24, n31, n33, and n34 are each an integer of 1 to 4; n25 and n35 is an integer of 1 or 2.

11. The ink of claim 6, wherein in the compound represented by formula (1), the molecule contains at least one sulfonic acid group or at least one carboxyl group.

12. The ink of claim 6, wherein the ink comprises the dye in the form of fine particle dispersion.

13. The ink of claim 6, wherein the ink comprises the dye together with an oil-soluble polymer in the form of fine particle dispersion.

* * * * *